(12) United States Patent
Kwon et al.

(10) Patent No.: US 10,919,972 B2
(45) Date of Patent: Feb. 16, 2021

(54) ANTI-HUMAN 4-1BB ANTIBODIES AND USES THEREOF

(71) Applicant: Eutilex Co., Ltd., Seoul (KR)

(72) Inventors: Byoung S. Kwon, Gwangmyeong-si (KR); Seoung-Joo Lee, Anyang-si (KR); Young Ho Kim, Goyang-si (KR); Ho-Sik Oh, Goyang-si (KR); Joong Won Lee, Goyang-si (KR)

(73) Assignee: Eutilex Co., Ltd., Seoul (KR)

( * ) Notice: Subject to any disclaimer, the term of this patent is extended or adjusted under 35 U.S.C. 154(b) by 80 days.

(21) Appl. No.: 16/191,381

(22) Filed: Nov. 14, 2018

(65) Prior Publication Data

US 2019/0071510 A1  Mar. 7, 2019

Related U.S. Application Data

(62) Division of application No. 15/863,526, filed on Jan. 5, 2018, now Pat. No. 10,174,122.

(60) Provisional application No. 62/443,281, filed on Jan. 6, 2017.

(51) Int. Cl.
| | | |
|---|---|---|
| *A61K 35/00* | (2006.01) | |
| *C07K 16/28* | (2006.01) | |
| *A61P 37/04* | (2006.01) | |
| *A61P 35/00* | (2006.01) | |
| *A61K 39/395* | (2006.01) | |
| *A61K 45/06* | (2006.01) | |
| *A61K 39/00* | (2006.01) | |

(52) U.S. Cl.
CPC ........ *C07K 16/2878* (2013.01); *A61K 39/395* (2013.01); *A61K 39/39558* (2013.01); *A61K 45/06* (2013.01); *A61P 35/00* (2018.01); *A61P 37/04* (2018.01); *C07K 16/28* (2013.01); *C07K 16/2818* (2013.01); *A61K 2039/505* (2013.01); *A61K 2039/507* (2013.01); *C07K 2317/24* (2013.01); *C07K 2317/34* (2013.01); *C07K 2317/51* (2013.01); *C07K 2317/515* (2013.01); *C07K 2317/565* (2013.01); *C07K 2317/567* (2013.01); *C07K 2317/75* (2013.01); *C07K 2317/76* (2013.01); *C07K 2317/92* (2013.01)

(58) Field of Classification Search
CPC combination set(s) only.
See application file for complete search history.

(56) References Cited

U.S. PATENT DOCUMENTS

| | | | |
|---|---|---|---|
| 6,458,934 B1 | 10/2002 | Hong et al. | |
| 6,905,684 B1 | 6/2005 | Kwon | |
| 7,932,045 B2 | 4/2011 | Kwon | |
| 2004/0224402 A1 | 11/2004 | Bonyhadi et al. | |
| 2006/0106196 A1 | 5/2006 | Gaudernack | |
| 2008/0261307 A1 | 10/2008 | Kwon et al. | |
| 2010/0158931 A1 | 6/2010 | Weinschenk | |
| 2014/0377255 A1 | 12/2014 | Ahrens et al. | |
| 2015/0259646 A1 | 9/2015 | Kwon et al. | |
| 2016/0244528 A1 | 8/2016 | Gray | |

FOREIGN PATENT DOCUMENTS

| | | |
|---|---|---|
| CA | 2420949 | 2/2002 |
| CN | 1357009 | 7/2002 |
| CN | 1867585 | 11/2006 |
| JP | H10-507627 | 7/1998 |
| JP | 2002-531383 | 9/2002 |
| JP | 2009-536036 | 10/2009 |
| JP | 2007-532095 | 11/2019 |
| KR | 2004/0083918 | 10/2004 |
| KR | 100468321 | 1/2005 |
| KR | 100500283 | 7/2005 |
| KR | 2008/0084308 | 8/2008 |
| KR | 10-0882445 | 2/2009 |
| KR | 100882445 | 2/2009 |
| KR | 2010/0011821 | 2/2010 |
| KR | 2010-0043130 | 4/2010 |
| KR | 10-1103603 | 1/2012 |
| KR | 101503341 | 3/2015 |
| KR | 10-2016-0165224 | 12/2016 |
| RU | 2551963 | 10/2015 |
| WO | WO 96/06929 | 3/1996 |
| WO | WO 2001/036452 | 5/2001 |
| WO | WO 01/042270 | 6/2001 |
| WO | WO 02/072013 | 9/2002 |
| WO | WO 03/049755 | 6/2003 |
| WO | WO 2004/016734 | 2/2004 |

(Continued)

OTHER PUBLICATIONS

Barbas et al., Combinatorial Immunoglobulin Libraries on the Surface of Phage (Phabs): Rapid Selection of Antigen-Specific Fabs, Methods: A Companion to Methods in Enzymology, 2(2): 119-124 (1991).

(Continued)

*Primary Examiner* — Lei Yao

(74) *Attorney, Agent, or Firm* — Fish & Richardson P.C.

(57) ABSTRACT

Provided are anti-human 4-1BB antibodies and fragments thereof with one or more structural features that are not found in a reference anti-human 4-1BB antibody, where said features may improve certain characteristics of the antibody relative to a reference antibody. Various in vitro and in vivo methods and reagents related to anti-human 4-1BB antibodies described herein are also provided. Methods include, for example, inducing T-cell proliferation, inducing T cell secretion of IFNγ, as well as detection, prevention, and/or therapeutic treatment of cancer using an anti-human 4-1BB antibody or fragment thereof.

2 Claims, 17 Drawing Sheets

Specification includes a Sequence Listing.

(56) References Cited

FOREIGN PATENT DOCUMENTS

| | | |
|---|---|---|
| WO | WO 2005/035584 | 4/2005 |
| WO | WO 2006/126835 | 11/2006 |
| WO | WO 2007/131210 | 11/2007 |
| WO | WO 2012/032433 | 3/2012 |
| WO | WO 2016/029073 | 2/2015 |
| WO | WO 2015/119923 | 8/2015 |
| WO | WO 2015/179236 | 11/2015 |
| WO | WO 2016/134358 | 8/2016 |
| WO | WO 2016/205277 | 12/2016 |
| WO | WO 2017/205745 | 11/2017 |
| WO | WO 2018/127787 | 7/2018 |

OTHER PUBLICATIONS

Bartkowiak, T. and M. Curran, 4-1 BB Agonists: Multi-Potent Potentiators of Tumor Immunity, Frontiers in Oncology, 5(117): 1-16 (2015).

Bhasin & Raghava, "Prediction of CTL Epitopes Using QM, SVM and ANN Techniques," Vaccine, 2004, 22:3195-3201.

Call et al, "Isolation and Characterization of a Zinc Finger Polypeptide Gene at the Human Chromosome 11 Wilms' Tumor Locus," Cell, 1990, 60:3:509-520.

Cheever et al, "The Prioritization of Cancer Antigens: A National Cancer Institute Pilot Project for the Acceleration of Translational Research," Clinical Cancer Research, 2009, 15:5323-5337.

Chen et al., Combination of 4-1 BB Agonist and PD-1 Antagonist Promotes Antitumor Effector/Memory CDS T Cells in a Poorly Immunogenic Tumor Model, Cancer Immunology Research, 3(2): 149-160 (2015).

Choi et al, "4-1 BB-based isolation and expansion of CDS+ T cells specific for self-tumor and non-self-tumor antigens for adoptive T-cell therapy," J Immunother, 2014, 37:4:225-236.

Croft, M., The role of TNF superfamily members in T-cell function and diseases, Nat. Rev. Immunol., 9(4): 271-85 (2009).

Decoster et al, Vaccination therapy for non-small-cell lung cancer: review of agents in phase III development, Annals of Oncoloqy, 2012, 23:5:1387-1393.

Fisher et al, "Targeting of 4-1 BB by monoclonal antibody PF-05082566 enhances Tcell function and promotes anti-tumor activity," Cancer Immunology, Immunotherapy, 61(10): 1721-1733 (2012).

Garn I-Wagner et al., 4-1 BB Is Expressed on CD45RAhiROhi Transitional T Cell in Humans, Cellular Immunology, 169: 91-98 (1996).

GenBank Accession No. AA061088.1, "Stratagene mouse testis (#937308) Mus musculus cDNA clone IMAGE: 514818 5-,mRNA sequence," Sep. 23, 1996, 1 page.

Gnjatic et al, "NY-ESO-1: review of an immunogenic tumor antigen," Adv. Cancer Res., 2006, 95:1-30.

Hinrichs & Restifo, Reassessing target antigens for adoptive T cell therapy Nature Biotechnol., Nov. 13, 2013, 31:999-1008.

Hochst and Diehl, "Antigen shedding into the circulation contributes to tumor immune escape," Oncoimmunology, 2012, 1:9:1620-1622.

International Search Report for PCT/IB2018/000043, ISA/AU, 5 pages (dated May 16, 2018).

International Search Report for PCT/KR2015/0002356, ISNKR, 5 pages (dated Jul. 10, 2015). English Translation.

Jager et al, "Simultaneous Humoral and Cellular Immune Response against Cancer-Testis Antigen NY-ESO-1: Definition of Human Histocompatibility Leukocyte Antigen (HLA)-A2-binding Peptide. Epitopes," Journal of Experimental Medicine, Jan. 19, 1998, 187:2:265-270.

Kim et al, Combination Therapy with Cisplatin and Anti-4-1 BB: Synergistic Anticancer Effects and Amelioration of Cisplatin-Induced Nephrotoxicity, Cancer Res., 68: 7264-7269 (2008).

Kim et al., Human 4-1 BB regulates CD28 co-stimulation to promote Thi cell responses, Eur. J. Immunol., 28: 881-890 (1998).

Kim et al., Neutralizing human monoclonal antibodies to hepatitis A virus recovered by phage display, Virology, 318: 598-607 (2004).

Kim et al., Selection of an affinity-matured antibody against a defined epitope by phage display of an immune antibody library, Journal of Immunological Methods, 329: 176-183 (2008).

Kim et al., "Specific association of human telomerase activity with immortal cells and cancer," Science, 1994, 266:5193:2011-2015.

Kwon et al., cDNA sequences of two inducible T-cell genes, Proc. Natl. Acad. Sci. USA, 86: 1963-1967 (1989).

Kwon et al., Isolation and initial characterization of multiple species of T-lymphocyte subset cDNA clones, Proc. Natl. Acad. Sci. USA, 84: 2896-2900 (1987).

Larsen et al., "Large-scale validation of methods for cytotoxic T-lymphocyte epitope prediction," BMC Bioinformatics, 2007, 8:424.

Lee et al., Molecular cloning of agonistic and antagonistic monoclonal antibodies against human 4-1 BB, Eur. J. Immunogenetics, 29: 449-452 (2002).

Lynch, D.H., The promise of 4-1 BB (CD137)-mediated immunomodulation and the immunotherapy of cancer, Immunol. Rev., 222:277-86 (2008).

Nakahara et al, "Expression of the Wilms' tumor gene product WT1 in glioblastomas and medulloblastomas," Brain Tumor Pathology, 2004, 21:113-116.

Ramarkrishnan et al, "Expression Profile of the Putative Catalytic Subunit of the Telomerase Gene," Cancer Research, 1998, 58:622-625.

Rammensee et al, "SYFPEITHI: database for MHC ligands and peptide motifs," Immunogenetics, 1999, 50:213-219.

Richards et al, "Glucocorticoids drive human CDb+ T cell differentiation towards a phenotype with high IL-10 and reduced IL-4, IL-5 and IL-13 production," Eur. J. Immunol., 2000, 30:2344-2354.

Richards et al, "Glucocorticoids drive human CD8 T cell differentiation towards a phenotype with high IL-10 and reduced IL-4, IL-5 and IL-13 production," Eur J Immunol., Aug. 2000, 30:2344-2354.

Scanlan et al, "Cancer/testis antigens: an expanding family of targets for cancer immunotherapy," Immunol. Rev., 2002, 188:22-32.

Shindo, Y. et al., Combination Immunotherapy with 4-1 BB Activation and PD-1 Blockade Enhances Antitumor Efficacy in a Mouse Model of Subcutaneous Tumor, Anticancer Research, 35: 129-136 (2015).

Son et al., Humanization of agonistic anti-human 4-1 BB monoclonal antibody using a phagedisplayed combinatorial library, Journal of Immunological Methods, 286: 187-201 (2004).

Taylor, S.F. and Bender, B.S., Beta 2-microglobulin-deficient mice demonstrate class II MHC restricted anti-viral CD4+ but not CDS+ CTL against influenza-sensitized autologous splenocytes, Immunol. Lett., 46(1-2): 67-73 (1995).

The abstract of Doering et al (Journal of Innnnunotherapy, 2011, vol. 34, No. 9, pp. 689-690) (Year: 2011).

The abstract of Nakamura et al (Blood, 2011, vol. 118, No. 21, pp. 435-436) (Year: 2011).

Tsuboi et al, "Enhanced induction of human WT1-specific cytotoxic T lymphocytes with a 9-mer WT1 peptide modified at HLA-A*2402-binding residues," Cancer Immunol Immunother, Oct. 18, 2002, 51:614-620.

Vinay, D. S. et al, Dual immunoregulatory pathways of 4-1 BB signaling, J. Mol. Med. ( Berl), 84(9): 726-36 (2006).

Vinay, D.S. and Kwon, B.S., 4-1 BB (CD137), an inducible costimulatory receptor, as a specific target for cancer therapy, BMB Rep. 4 7(3): 222-9 (2014).

Walter et al, "Multipeptide immune response to cancer vaccine IMA901 after single-dose cyclophosphamide associates with longer patient survival," Nature Med., Aug. 2012, 18:1254-1261.

Wölfl et al., "Use of CD137 to Study the Full Repertoire of CD8+ T Cells Without the Need to Know Epitope Specificities," Cytometry A, Nov. 2008, 73:1043-1049.

Written Opinion for PCT/IB2018/000043, ISA/AU, 5 pages (dated May 16, 2018).

Written Opinion for PCT/KR2015/000235, ISA/KR, 14 pages (dated Apr. 3, 2015). English Translation.

Yee, "Adoptive T Cell Therapy for Cancer: Boutique Therapy or Treatment Modality?," Clin. Cancer Res., 2013, 19(17):4550-4553.

(56) References Cited

OTHER PUBLICATIONS

Zhou et al., Characterization of human homologue of 4-1 BB and its ligand, Immunology Letters, 45: 67-73 (1995).
Australian Office Action in Application No. 2019204847, dated May 7, 2020, 4 pages.
Chinese Office Action in Application No. 201880005123, dated Jan. 16, 2020, 12 pages, English Translation.
Ho et al (Journal of Immunological Methods, vol. 310, pp. 40-52, 2006.
Hong et al., "A Humanized Anti-4-1BB Monoclonal Antibody Suppresses Antigen-Induced Humoral Immune Response in Nonhuman Primates", Journal Immunotherapy, vol. 23, No. 6, pp. 613-621, 2000.
Lee et al., "Administration of agonistic anti-4-1BB monoclonal antibody leads to the amelioration of inflammatory bowel disease", Immunology Letters, vol. 101, Issue 2, pp. 210-216, 2005.
Mizukoshi et al., Hepatology, vol. 43, pp. 1284-1294, 2006.
Zhou et al, Preparation of Mouse Anti-human 4-1BB Monoclonal Antibody and Identification of Its Biological Characteristics Journal of cell and molecular immunology, vol. 27, No. 9, 2011.
Chen et al., "Identification of NY-ES0-1 Peptide Analogues Capable of Improved Stimulation of Tumor-Reactive CTL", Journal of Immunology, vol. 165, pp. 948-955, 2000.
European Search Report in Application No. 18736336, dated Sep. 11, 2019, 9 pages.
Japanese Office Action in Application No. 2019-517981, dated Oct. 10, 2019 English Translation, 2 pages.
Li et al., "Immunotherapy of melanoma with the immune costimulatory monoclonal antibodies targeting CD137", Clinical Pharmacology: Advances and Applications, p. 47, 2013.

Miyagawa et al., "A Newly Identified MAGE-3-Derived, HLA-A24-Restricted Peptide Is Naturally Processed and Presented as a CTL Epitope on MAGE-3-Expressing Gastrointestinal Cancer Cells", Oncology, vol. 70, pp. 54-62, 2006.
Murillo et al., "Therapeutic Antitumor Efficacy of Anti-CD137 Agonistic Monoclonal Antibody in Mouse Models of Myeloma", Clin Cancer Res., 14(21), 6895-6906, 2008.
Oji et al., "Expression of the Wilms' Tumor Gene WTJ in Solid Tumors and Its Involvement in Tumor Cell Growth", Japanese Journal of Cancer Research, vol. 90, pp. 194-204, 1999.
Parkhurst et al., "Identification of a Shared HIA-A *0201-restricted T-Cell Epitope from the Melanoma Antigen Tyrosinase-related Protein 2 (TRP2)", Cancer Research, vol. 58, pp. 4895-4901, 1998.
Russian Office Action in Application No. 2019116731, dated Nov. 12, 2019, 4 pages.
Yee et al., "Isolation of High Avidity Melanoma-Reactive CTL from Heterogeneous Populations Using Peptide-MHC Tetramers", (Journal of Immunology, vol. 162, pp. 2227-2234, 1999.
Canadian Office Action in Canadian Appln No. 2942557, dated Aug. 5, 2020, 7 pages.
Housseau et al. "Tumor-specific CD8+ T Lymphocytes Derived From the Peripheral Blood of Prostate Cancer Patients by in vitro stimulation with Autologous Tumor Cell Lines", Int. J. Cancer, Mar. 2002, 98(1):57-62.
Lim, O. et al., "GMP-Compliant, Large-Scale Expanded Allogeneic Natural Killer Cells Have Potent Cytolytic Activity against Cancer Cells In Vitro and In Vivo",PLOS ONE, Jan. 2013, 8:1-8.
Stromnes, et al., "Re-adapting T cells for cancer therapy: from mouse models to clinical trials," Immunol Rev., Jan. 2014, 257: 145-164.

FIG. 5

| Antibody | Ka(1/Ms) | Kd(1/s) | $K_D$(M) |
|---|---|---|---|
| EU101 | 1.57e10 | 1.8e-5 | 6.36e-11 |
| 94G1 | 1.66e9 | 1.18e-4 | 6.02e-10 |

SEQUENCE LISTING

<160> NUMBER OF SEQ ID NOS: 44

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Thr Ile Ser Asp Tyr
1               5

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ala Ser
1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Asp Gly His Ser Phe Pro Pro Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Asp Gly His Ser Trp Pro Pro Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Thr Phe Ser Ser Tyr Trp
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Ile Asn Pro Gly Asn Gly His Thr
1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Arg Ser Phe Thr Thr Ala Arg Ala Phe Ala Tyr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Arg Ser Phe Lys Thr Ala Arg Ala Phe Ala Tyr
1               5                   10

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Phe Pro Pro
                85                  90                  95

Thr Phe Gly Gln Gly Thr Lys Leu Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Met Thr Gln Ser Pro Ala Phe Leu Ser Val Thr Pro Gly

```
                1               5                  10                  15
            Glu Lys Val Thr Ile Thr Cys Arg Ala Ser Gln Thr Ile Ser Asp Tyr
                            20                  25                  30

Leu His Trp Tyr Gln Gln Lys Pro Asp Gln Ala Pro Lys Leu Leu Ile
                        35                  40                  45

Lys Tyr Ala Ser Gln Ser Ile Ser Gly Ile Pro Ser Arg Phe Ser Gly
                    50                  55                  60

Ser Gly Ser Gly Thr Asp Phe Thr Phe Thr Ile Ser Ser Leu Glu Ala
            65                  70                  75                  80

Glu Asp Ala Ala Thr Tyr Tyr Cys Gln Asp Gly His Ser Trp Pro Pro
                            85                  90                  95

Thr Phe Gly Gln Gly Thr Lys Leu Glu Ile Lys
                            100                 105

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Gln Ser Gly Ala Glu Val Lys Lys Pro Gly Ala
            1               5                   10                  15

Ser Val Lys Leu Ser Cys Lys Ala Ser Gly Tyr Thr Phe Ser Ser Tyr
                            20                  25                  30

Trp Met His Trp Val Arg Gln Ala Pro Gly Gln Gly Leu Glu Trp Ile
                        35                  40                  45

Gly Glu Ile Asn Pro Gly Asn Gly His Thr Asn Tyr Asn Glu Lys Phe
                    50                  55                  60

Lys Ser Arg Ala Thr Met Thr Arg Asp Thr Ser Thr Ser Thr Ala Tyr
            65                  70                  75                  80

Met Glu Leu Ser Ser Leu Arg Ser Glu Asp Ser Ala Val Tyr Tyr Cys
                            85                  90                  95

Ala Arg Ser Phe Thr Thr Ala Arg Ala Phe Ala Tyr Trp Gly Gln Gly
                            100                 105                 110

Thr Leu Val Thr Val Ser Ser
                    115

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Ser Gly Ala Glu Val Lys Lys Pro Gly Ala
            1               5                   10                  15

Ser Val Lys Leu Ser Cys Lys Ala Ser Gly Tyr Thr Phe Ser Ser Tyr
                            20                  25                  30

Trp Met His Trp Val Arg Gln Ala Pro Gly Gln Gly Leu Glu Trp Ile
                        35                  40                  45

Gly Glu Ile Asn Pro Gly Asn Gly His Thr Asn Tyr Asn Glu Lys Phe
                    50                  55                  60

Lys Ser Arg Ala Thr Met Thr Arg Asp Thr Ser Thr Ser Thr Ala Tyr
```

```
                      65                  70                  75                  80
Met Glu Leu Ser Ser Leu Arg Ser Glu Asp Ser Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser
        115

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Val Thr Met Thr Arg Asp Thr Ser Thr Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser
        115

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser
```

<210> SEQ ID NO 15
<211> LENGTH: 20
<212> TYPE: PRT
<213> ORGANISM: Homo sapiens

<400> SEQUENCE: 15

Cys Pro Ala Gly Thr Phe Cys Asp Asn Asn Arg Asn Gln Ile Cys Ser
1               5                   10                  15

Pro Cys Pro Pro
            20

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Val Gln Leu Gln Gln Ser Gly Ala Glu Val Lys Lys Pro Gly Ala
1               5                   10                  15

Ser Val Lys Leu Ser Cys Lys Ala Ser
            20                  25

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Val Gln Leu Val Gln Ser Gly Ala Glu Val Lys Lys Pro Gly Ala
1               5                   10                  15

Ser Val Lys Leu Ser Cys Lys Ala Ser
            20                  25

<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asn Tyr Asn Glu Lys Phe Lys Ser Arg Ala Thr Met Thr Arg Asp Thr
1               5                   10                  15

Ser Thr Ser Thr Ala Tyr Met Glu Leu Ser Ser Leu Arg Ser Glu Asp
            20                  25                  30

Ser Ala Val Tyr Tyr Cys
            35

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 19

Asn Tyr Asn Glu Lys Phe Lys Ser Arg Val Thr Met Thr Arg Asp Thr
1               5                   10                  15

Ser Thr Ser Thr Ala Tyr Met Glu Leu Ser Ser Leu Arg Ser Glu Asp
                20                  25                  30

Ser Ala Val Tyr Tyr Cys
            35

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asn Tyr Asn Glu Lys Phe Lys Ser Arg Val Thr Met Thr Arg Asp Thr
1               5                   10                  15

Ser Thr Ser Thr Ala Tyr Met Glu Leu Ser Ser Leu Arg Ser Glu Asp
                20                  25                  30

Thr Ala Val Tyr Tyr Cys
            35

<210> SEQ ID NO 21
<211> LENGTH: 107
<212> TYPE: PRT
<213> ORGANISM: Homo sapiens

<400> SEQUENCE: 21

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 22
<211> LENGTH: 330
<212> TYPE: PRT
<213> ORGANISM: Homo sapiens

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 23
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys

```
                85                  90                  95
Lys Val Glu Pro Lys Ser Cys Asp Lys Thr His Thr Cys Pro Pro Cys
            100                 105                 110
Pro Ala Pro Glu Ala Ala Gly Gly Pro Ser Val Phe Leu Phe Pro Pro
            115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Ala Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggatccacaa gatcattgca g                                                   21

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttgagctcga gcctggtcct gaaaaca                                             27

<210> SEQ ID NO 26
<211> LENGTH: 27
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 26
cgcgtggatc caaggagtgt tcctcca                                          27

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttgagctcga gacgtttctg atcgtta                                          27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgcgtggatc cggcatctgt cgaccct                                          27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ttgagctcga ggatctgcgg agagtgt                                          27

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggatccacaa gatcattgca g                                                21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctcgaggcat atgtcacagg t                                                21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ggatccacaa gatcattgca g                                             21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctcgaggctg gagaaactat                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggatcctgcc cagctggtac                                               20

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttgagctcga gcctggtcct gaaaaca                                       27

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggatccagga atcagatttg c                                             21

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttgagctcga gcctggtcct gaaaaca                                       27

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggatccacaa gatcattgca g                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctcgaggcaa atctgattcc t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggatccacaa gatcattgca g                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctcgagtgga ggacagggac t                                              21

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Ala Asn Asn Pro Asp Trp Asp Phe Asn Pro
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Tyr Lys Asp Asp Asp Asp Lys
1               5

<210> SEQ ID NO 44
<211> LENGTH: 255
<212> TYPE: PRT
<213> ORGANISM: Homo sapiens

<400> SEQUENCE: 44

-continued

```
Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
            35              40                  45

Pro Pro Asn Ser Phe Ser Ser Ala Gly Gly Gln Arg Thr Cys Asp Ile
50                      55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135             140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

ANTI-HUMAN 4-1BB ANTIBODIES AND USES THEREOF

CROSS-REFERENCE TO RELATED APPLICATIONS

This application is a continuation of U.S. patent application Ser. No. 15/863,526, filed Jan. 5, 2018, which claims priority to and the benefit of U.S. Patent Application No. 62/443,281, filed on Jan. 6, 2017, the disclosures of each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 22, 2018, is named 2012994-0035_SL.txt and is 24,817 bytes in size.

BACKGROUND

Cancer remains one of the leading causes of death in the world. Recent statistics report that 13% of the world population dies from cancer. According to estimates from the International Agency for Research on Cancer (IARC), in 2012 there were 14.1 million new cancer cases and 8.2 million cancer deaths worldwide. By 2030, the global burden is expected to grow to 21.7 million new cancer cases and 13 million cancer deaths due to population growth and aging and exposure to risk factors such as smoking, unhealthy diet and physical inactivity. Further, pain and medical expenses for cancer treatment cause reduced quality of life for both cancer patients and their families. It is apparent that, above all, cancer is a disease for which it is necessary to urgently find improved treatment methods.

SUMMARY

The present disclosure provides, among other things, antibodies and fragments thereof that bind to a human 4-1BB polypeptide. In some aspects, provided anti-human 4-1BB antibodies and fragments thereof are variants of a reference anti-human 4-1BB antibody in that they contain one or more particular structural features that are not found in the reference anti-human 4-1BB antibody. The present disclosure encompasses a recognition that provided variant anti-human 4-1BB antibodies have improved properties relative to a reference anti-human 4-1BB antibody lacking one or more structural features described herein. In some embodiments, provided anti-human 4-1BB antibodies and fragments thereof have one or more improved properties, such as, for example, improved binding affinity, improved induction of T cell proliferation (e.g., proliferation of $CD8^+$ T cells), increased ability to induce $IFN\gamma$ production by T cells (e.g., proliferation of $CD8^+$ T cells), improved ability to reduce and/or eliminate cancer proliferation in vivo (e.g., at a lower dose).

In some embodiments, an anti-4-1BB antibody or antigen-binding antibody fragment includes 1, 2, or 3 heavy chain CDR sequences that are or include a sequence of SEQ ID NOs: 5 to 8. In some embodiments, an anti-4-1BB antibody or antigen-binding antibody fragment includes one or more of: a heavy chain CDR1 that is or includes a sequence of SEQ ID NO: 5, a heavy chain CDR2 that is or includes a sequence of SEQ ID NO: 6 and a heavy chain CDR3 that is or includes a sequence of SEQ ID NO: 7 or 8.

In some embodiments, an anti-4-1BB antibody or antigen-binding antibody fragment includes each of: a heavy chain CDR1 that is or includes a sequence of SEQ ID NO: 5, a heavy chain CDR2 that is or includes a sequence of SEQ ID NO: 6 and a heavy chain CDR3 that is or includes a sequence of SEQ ID NO: 7 or 8.

In some embodiments, an anti-4-1BB antibody or antigen-binding antibody fragment includes 1, 2, or 3 light chain CDR sequences that are or include a sequence of SEQ ID NOs: 1-4. In some embodiments, an anti-4-1BB antibody or antigen-binding antibody fragment includes one or more of: a light chain CDR1 that is or includes a sequence of SEQ ID NO: 1, a light chain CDR2 that is or includes a sequence of SEQ ID NO: 2 and a light chain CDR3 that is or includes a sequence of SEQ ID NO: 3 or 4. In some embodiments, an anti-4-1BB antibody or antigen-binding antibody fragment includes each of: a light chain CDR1 that is or includes a sequence of SEQ ID NO: 1, a light chain CDR2 that is or includes a sequence of SEQ ID NO: 2 and a light chain CDR3 that is or includes a sequence of SEQ ID NO: 3 or 4.

In some embodiments, an anti-4-1BB antibody or antigen-binding antibody fragment includes a heavy chain variable domain that includes a heavy chain CDR1 that is or includes a sequence of SEQ ID NO: 5, a heavy chain CDR2 that is or includes a sequence of SEQ ID NO: 6 and a heavy chain CDR3 that is or includes a sequence of SEQ ID NO: 7 or 8, and/or a light chain variable domain that includes a light chain CDR1 that is or includes a sequence of SEQ ID NO: 1, a light chain CDR2 that is or includes a sequence of SEQ ID NO: 2 and a light chain CDR3 that is or includes a sequence of SEQ ID NO: 4.

In some embodiments, an anti-4-1BB antibody or antigen-binding antibody fragment includes a heavy chain variable domain that includes a heavy chain framework 1 (FR1) region comprising a sequence of SEQ ID NO: 16 or 17. In some embodiments, an anti-4-1BB antibody or antigen-binding antibody fragment includes a heavy chain variable domain that includes a heavy chain framework 3 (FR3) region comprising a sequence of any one of SEQ ID NOs: 18-20. In some embodiments, an anti-4-1BB antibody or antigen-binding antibody fragment includes a heavy chain variable domain that includes a heavy chain framework 1 (FR1) region comprising a sequence of SEQ ID NO: 16 or 17 and a heavy chain framework 3 (FR3) region comprising a sequence of any one of SEQ ID NOs: 18-20.

In some embodiments, an anti-4-1BB antibody or antigen-binding antibody fragment includes substantial homology to an antibody or antibody fragment that includes a heavy chain variable domain that is or includes a sequence selected from SEQ ID NOs: 11-14. In some embodiments, an anti-4-1BB antibody or antigen-binding antibody fragment includes a heavy chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 11-14. In some embodiments, an anti-4-1BB antibody or antigen-binding antibody fragment includes a heavy chain variable domain that is or includes a sequence selected from SEQ ID NOs: 11-14.

In some embodiments, an anti-4-1BB antibody or antigen-binding antibody fragment includes substantial homology to an antibody or antibody fragment that includes a light chain variable domain that is or includes a sequence of SEQ ID NO: 9 or 10. In some embodiments, an anti-4-1BB antibody or antigen-binding antibody fragment includes a light chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence of SEQ ID NO: 9 or 10. In some embodiments, an anti-4-1BB antibody or antigen-binding antibody fragment includes a light chain variable domain that is or includes a sequence of SEQ ID NO: 9 or 10.

In some embodiments, an anti-4-1BB antibody or antigen-binding antibody fragment includes substantial homology to an antibody or antibody fragment that includes a heavy chain variable domain that is or includes a sequence selected from SEQ ID NOs: 11-14 and a light chain variable domain that is or includes a sequence of SEQ ID NO: 10. In some embodiments, an anti-4-1BB antibody or antigen-binding antibody fragment includes a heavy chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 11-14 and a light chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence of SEQ ID NO: 10. In some embodiments, an anti-4-1BB antibody or antigen-binding antibody fragment includes a heavy chain variable domain that is or includes a sequence selected from SEQ ID NOs: 11-14 and a light chain variable domain that is or includes a sequence of SEQ ID NO: 10.

In some embodiments, a provided anti-human 4-1BB antibody or fragment thereof is an agonistic antibody. In some embodiments, a provided anti-human 4-1BB antibody or fragment thereof is characterized as having superior agonistic activity than a humanized anti-human 4-1BB antibody 94G1 (i.e., an antibody including light chain and heavy chain variable domains of SEQ ID NOs: 9 and 11, respectively). In some embodiments, a provided anti-human 4-1BB antibody or fragment thereof is characterized as having improved binding affinity than a humanized anti-human 4-1BB antibody 94G1 (i.e., an antibody including light chain and heavy chain variable domains of SEQ ID NOs: 9 and 11, respectively).

In some embodiments, a provided anti-human 4-1BB antibody or fragment thereof is or comprises a humanized antibody. In some embodiments, a provided anti-human 4-1BB antibody or fragment thereof includes a human immunoglobulin constant domain, wherein the constant domain is selected from an IgG1 or a variant thereof, an IgG2 or a variant thereof, an IgG4 or a variant thereof, an IgA or a variant thereof, an IgE or a variant thereof, an IgM or a variant thereof, and an IgD or a variant thereof. In some embodiments, a provided anti-human 4-1BB antibody or fragment thereof is or comprises a human IgG1. In some embodiments, an IgG1 is or comprises a sequence that is at least 95% identical to SEQ ID NO: 22 or 23.

In some embodiments, a provided anti-human 4-1BB antibody or fragment thereof is a monoclonal antibody.

In some embodiments, a provided anti-human 4-1BB antibody or fragment thereof is a full length antibody. In some embodiments, a provided anti-human 4-1BB antibody or fragment thereof is a Fab fragment, a Fab' fragment, a F(ab')2 fragment, a Fv fragment, a disulfide-bonded Fv fragment, a scFv fragment, a single domain antibody, humabody, nanobody, or a diabody.

In some embodiments, a provided anti-human 4-1BB antibody or fragment thereof has a binding affinity ($K_D$) for a human 4-1BB molecule of $1\times10^{-7}$ to $1\times10^{-12}$ M. In some embodiments, a provided anti-human 4-1BB antibody or fragment thereof has a binding affinity ($K_D$) for a human 4-1BB molecule of $1\times10^{-8}$ to $1\times10^{-12}$ M. In some embodiments, a provided anti-human 4-1BB antibody or fragment thereof has a binding affinity ($K_D$) for a human 4-1BB molecule of $1\times10^{-9}$ to $1\times10^{-12}$ M. In some embodiments, a provided anti-human 4-1BB antibody or fragment thereof has a binding affinity ($K_D$) for a human 4-1BB molecule of $1\times10^{-10}$ to $1\times10^{-12}$ M.

In some embodiments, a provided anti-human 4-1BB antibody or fragment thereof binds to an epitope within the extracellular domain of a human 4-1BB polypeptide. In some embodiments, a provided anti-human 4-1BB antibody or fragment thereof binds to an epitope within the extracellular domain of human 4-1BB. In some embodiments, binding of a provided anti-human 4-1BB antibody or fragment thereof is abrogated by one or more mutations at positions N30, D38, N39, and R41 of SEQ ID NO: 44.

In some embodiments, a provided anti-human 4-1BB antibody or fragment thereof fails to bind or weakly binds a non-primate 4-1BB polypeptide. In some embodiments, a provided anti-human 4-1BB antibody or fragment thereof fails to bind or weakly binds a canine 4-1BB polypeptide.

In some embodiments, the present disclosure provides nucleic acid molecules encoding an anti-4-1BB antibody or antigen-binding fragment. In some embodiments, the present disclosure provides vectors that include a nucleic acid molecule encoding an anti-4-1BB antibody or antigen-binding fragment. In some embodiments, the present disclosure provides host cells that include a vector and/or nucleic acid molecule encoding an anti-4-1BB antibody or antigen-binding fragment. In some embodiments, a host cell is selected from a bacterial, yeast, insect or mammalian cell. In some embodiments, a is selected from the group consisting of *E. coli, P. pastoris*, Sf9, COS, HEK293, CHO and a mammalian lymphocyte.

In some embodiments, the present disclosure provides pharmaceutical compositions that include an anti-4-1BB antibody or antigen-binding fragment and a pharmaceutically acceptable carrier. In some embodiments, the present disclosure provides pharmaceutical compositions that include a nucleic acid and/or vector encoding an anti-4-1BB antibody or antigen-binding fragment and a pharmaceutically acceptable carrier.

In some embodiments, the present disclosure provides methods of treating a subject in need thereof, the method comprising administering to the subject a composition that comprises or delivers an anti-4-1BB antibody or antigen-binding fragment. In some embodiments, the present disclosure provides methods of treating a subject in need thereof, the method comprising administering to the subject a composition that comprises or delivers a nucleic acid and/or vector encoding an anti-4-1BB antibody or antigen-binding fragment. In some embodiments, a subject has or is at risk for developing cancer.

In some embodiments, the present disclosure provides methods of inducing an immune response in a subject in need thereof, the method comprising administering to the subject a composition that comprises or delivers an anti-4-1BB antibody or antigen-binding fragment. In some embodiments, the present disclosure provides methods of inducing an immune response in a subject in need thereof, the method comprising administering to the subject a composition that comprises or delivers a nucleic acid and/or vector encoding an anti-4-1BB antibody or antigen-binding fragment. In some embodiments, a subject has or is at risk for developing cancer.

In some embodiments, the present disclosure provides methods of enhancing an immune response in a subject in need thereof, the method comprising administering to the subject a composition that comprises or delivers an anti-4-

1BB antibody or antigen-binding fragment. In some embodiments, the present disclosure provides methods of enhancing an immune response in a subject in need thereof, the method comprising administering to the subject a composition that comprises or delivers a nucleic acid and/or vector encoding an anti-4-1BB antibody or antigen-binding fragment. In some embodiments, a subject has or is at risk for developing cancer.

In some embodiments, a cancer to be treated by a method of the present disclosure in a subject is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, and prostate cancer.

In some embodiments, a composition comprises or delivers an anti-human 4-1BB antibody of the present disclosure or an antigen-binding fragment thereof at a dose of 0.01 mg/kg to 100 mg/kg. In some embodiments, a composition comprises or delivers an anti-human 4-1BB antibody or an antigen-binding fragment thereof at a dose of about 0.01 mg/kg, 0.025 mg/kg, 0.05 mg/kg, 0.075 mg/kg, 0.1 mg/kg, 0.25 mg/kg, 0.5 mg/kg, 0.75 mg/kg, 1 mg/kg, 2 mg/kg, 3 mg/kg, 4 mg/kg, 5 mg/kg, 8 mg/kg, 10 mg/kg, 20 mg/kg, 25 mg/kg, 30 mg/kg, 40 mg/kg, 50 mg/kg, 50 mg/kg, 70 mg/kg, 80 mg/kg, 90 mg/kg, or 100 mg/kg.

In some embodiments, anti-human 4-1BB antibodies and/or fragments thereof and/or compositions comprising the same are characterized by inducing increased T cell proliferation (e.g., $CD8^+$ T cell proliferation) and/or increased IFNγ secretion by T cells (e.g., $CD8^+$ T cells) in a subject.

In some embodiments, the present disclosure provides methods that include administering to the subject a composition that comprises or delivers an anti-4-1BB antibody or antigen-binding fragment to a subject that has been administered or will be administered one or more additional anticancer therapies. In some embodiments, the present disclosure provides methods that include administering to the subject a composition that comprises or delivers an anti-4-1BB antibody or antigen-binding fragment to a subject that has been administered or will be administered one or more of ionizing radiation, a chemotherapeutic agent, an antibody agent, and a cell-based therapy, such that the subject receives treatment with both.

In some embodiments, the present disclosure provides methods that include administering to the subject a composition that comprises or delivers an anti-4-1BB antibody or antigen-binding fragment to a subject that has been administered or will be administered one or more of an immune checkpoint inhibitor, IL-12, GM-CSF, an anti-CD4 agent, fluorouracil, doxorubicin, irinotecan, paclitaxel, cisplatin, or cyclophosphamide.

In some embodiments, the present disclosure provides methods that include administering to the subject a composition that comprises or delivers an anti-4-1BB antibody or antigen-binding fragment to a subject that has been administered or will be administered a composition comprising an immune checkpoint inhibitor, such that the subject receives treatment with both. In some embodiments, an immune checkpoint inhibitor is an agent that inhibits PD-1 signaling. In some embodiments, an agent that inhibits PD-1 signaling is an anti-PD-1 antibody. In embodiments, an anti-PD-1 antibody is nivolumab, pembrolizumab, atezolizumab, durvalumab, or avelumab.

In some embodiments, the present disclosure provides methods of determining a dose of an anti-4-1BB antibody or antigen binding fragment thereof for therapeutic treatment of a subject in need thereof. In some embodiments, such a method includes (i) providing or obtaining a measurement of secreted IFN-gamma in a biological sample from the subject, wherein the subject has been administered a composition that comprises or delivers an amount of an anti-4-1BB antibody or antigen-binding fragment described herein; and (ii) comparing the measurement of secreted IFN-gamma to a reference value, where if the measurement of secreted IFN-gamma is higher or lower than the reference value, adjusting the amount of an anti-4-1BB antibody or antigen binding fragment thereof to be administered, thereby determining a dose for therapeutic treatment of a subject. In some embodiments, a reference value comprises an index value which includes a value derived from one or more healthy subjects, a value derived from one or more cancer diagnosed subject or a value derived from a cancer risk prediction algorithm. In some embodiments, a biological sample is a sample of whole blood, plasma, or serum. In some embodiments, a subject has or is at risk for developing cancer. In some embodiments, a cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, and prostate cancer.

In some embodiments, the present disclosure provides methods for increasing secretion of IFN-γ by a cell in vivo or in vitro that include: contacting the cell with an anti-4-1BB antibody or antigen-binding fragment described herein.

In some embodiments, the present disclosure provides methods ex vivo proliferation or isolation of activated T cells that include: contacting a population of T cells with an anti-4-1BB antibody or antigen-binding fragment described herein, thereby increasing proliferation of activated T cells.

In some embodiments, the present disclosure provides methods for isolating antigen-specific activated T cells that include one or more steps of: (a) culturing peripheral blood mononuclear cells (PBMC) in a medium together with a peptide of an epitope of interest and IL-2; (b) inducing 4-1BB expression in the cultured cells by adding the peptide of the epitope of interest; (c) contacting the cultured cells with a surface coated with an anti-4-1BB antibody or antigen-binding fragment described herein, wherein cultured cells expressing 4-1BB adhere to the coated surface; and (d) removing unattached cells, thereby isolating antigen-specific activated T cells. In some embodiments, activated T cells are $CD8^+$ T cells.

In some embodiments, the present disclosure provides methods for treating or preventing cancer in a subject in need thereof that includes administering to the subject a composition that includes a therapeutically effective amount of activated T cells produced by any of the method described herein. In some embodiments, a cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, and prostate cancer. In some embodiments, a composition includes least $10^9$, at least $10^{10}$ cells, or more than $10^{10}$ activated T cells. In some embodiments, activated T cells are CD8+ T cells.

Also provided, among other things, are technologies for characterizing anti-human 4-1BB antibodies and/or fragments thereof as described herein and/or compositions comprising the same. In some embodiments, provided are methods for characterizing anti-human 4-1BB antibodies and/or fragments thereof and/or compositions comprising the same binding to AML cells (e.g., HL60). In some embodiments, provided are methods for characterizing anti-human 4-1BB antibodies and/or fragments thereof and/or compositions comprising the same are by ELISA, immunohistochemistry, Biacore binding assays, mass spectrometry, isoelectric focusing (IEF) chromatography, and/or western blot.

The present disclosure provides various technologies related to making or manufacturing anti-human 4-1BB antibodies and/or fragments thereof as described herein and/or compositions containing said antibodies or fragments thereof.

As used in this application, the terms "about" and "approximately" are used as equivalents. Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The Drawing included herein, which is comprised of the following Figures, is for illustration purposes only and not for limitation. The foregoing and other objects, aspects, features, and advantages of the present disclosure will become more apparent and better understood by referring to the following description taken in conjunction with the accompanying figures in which:

FIG. 5 provides a table listing in vitro binding affinities of variant anti-4-1BB antibodies for 4-1BB. Binding affinity was measured using surface plasmon resonance (SPR, Biacore 3000). 94G1 and EU101 are exemplary humanized variant anti-4-1BB antibodies.

CERTAIN DEFINITIONS

Figure 1A:
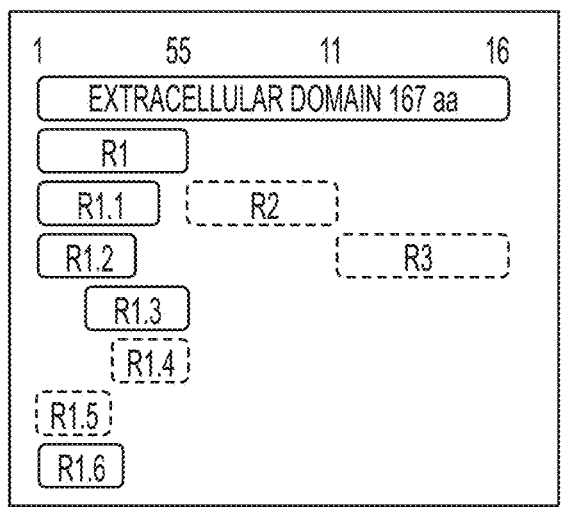
FIG. 1A depicts human 4-1BB extracellular domain (ECD) constructs. At the top is a schematic of a full length 4-1BB ECD (167 amino acids), and below is shown various fragments of a 4-1BB ECD: R1 (1-55 aa), R2 (56-110 aa), R3 (110-167 aa), R1.1 (1-45 aa), R1.2 (1-35 aa), R1.3 (11-55 aa), R1.4 (21-55 aa) R1.5 (1-25 aa) and R1.6 (1-30 aa). Each of these 4-1BB ECD constructs were fused with GST.

In the description that follows, a number of terms used in recombinant DNA and immunology are extensively utilized. In order to provide a clearer and consistent understanding of the specification and claims, including the scope to be given such terms, the following definitions are provided.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Agonist: Those skilled in the art will appreciate that the term "agonist" may be used to refer to an agent condition, or event whose presence, level, degree, type, or form correlates with an increased level or activity of another agent (i.e., the agonized agent). In general, an agonist may be or include an agent of any chemical class including, for example, small molecules, polypeptides, nucleic acids, carbohydrates, lipids, metals, and/or any other entity that shows the relevant activating activity. In some embodiments, an agonist may be direct (in which case it exerts its influence directly upon its target); in some embodiments, an agonist may be indirect (in which case it exerts its influence by other than binding to its target; e.g., by interacting with a regulator of the target, so that level or activity of the target is altered).

Animal: as used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Antagonist: Those skilled in the art will appreciate that the term "antagonist", as used herein, may be used to refer to an agent condition, or event whose presence, level, degree, type, or form correlates with decreased level or activity of another agent (i.e., the inhibited agent, or target). In general, an antagonist may be or include an agent of any chemical class including, for example, small molecules, polypeptides, nucleic acids, carbohydrates, lipids, metals, and/or any other entity that shows the relevant inhibitory activity. In some embodiments, an antagonist may be direct (in which case it exerts its influence directly upon its target); in some embodiments, an antagonist may be indirect (in which case it exerts its influence by other than binding to its target; e.g., by interacting with a regulator of the target, so that level or activity of the target is altered).

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); humabodies, VHHs; Anticalins®; Nanobodies® minibodies; BiTE®s; ankyrin repeat proteins or DARPINs®; Avimers®; DARTs; TCR-like antibodies; Adnectins®; Affilins®; Trans-Bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

Antibody fragment: As used herein, an "antibody fragment" refers to a portion of an antibody or antibody agent as described herein, and typically refers to a portion that includes an antigen-binding portion or variable region thereof. An antibody fragment may be produced by any means. For example, in some embodiments, an antibody fragment may be enzymatically or chemically produced by fragmentation of an intact antibody or antibody agent. Alternatively, in some embodiments, an antibody fragment may be recombinantly produced (i.e., by expression of an engineered nucleic acid sequence. In some embodiments, an antibody fragment may be wholly or partially synthetically produced. In some embodiments, an antibody fragment (particularly an antigen-binding antibody fragment) may have a length of at least about 50, 60, 70, 80, 90, 100, 110, 120, 130, 140, 150, 160, 170, 180, 190 amino acids or more, in some embodiments at least about 200 amino acids.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

CDR: as used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

Chemotherapeutic Agent: The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more *vinca* alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIBO15, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine.

Combination therapy: As used herein, the term "combination therapy" refers to those situations in which a subject is simultaneously exposed to two or more therapeutic regimens (e.g., two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality.

Corresponding to: As used herein, the term "corresponding to" may be used to designate the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

Engineered. In general, the term "engineered" refers to the aspect of having been manipulated by the hand of man. For example, a polypeptide is considered to be "engineered" when the polypeptide sequence manipulated by the hand of man. For example, in some embodiments of the present invention, an engineered polypeptide comprises a sequence that includes one or more amino acid mutations, deletions and/or insertions that have been introduced by the hand of man into a reference polypeptide sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, derivatives and/or progeny of an engineered polypeptide or cell are typically still referred to as "engineered" even though the actual manipulation was performed on a prior entity.

Epitope: as used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Ex vivo: as used herein refers to biologic events that occur outside of the context of a multicellular organism. For example, in the context of cell-based systems, the term may be used to refer to events that occur among a population of cells (e.g., cell proliferation, cytokine secretion, etc.) in an artificial environment.

Framework or framework region: as used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

Humanized: as is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

$K_D$: as used herein, refers to the dissociation constant of a binding agent (e.g., an antibody or binding component thereof) from a complex with its partner (e.g., the epitope to which the antibody or binding component thereof binds).

Operably linked: as used herein, refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest; in some embodiments, control elements act in trans to or otherwise at a from the functional element of interest.

Pharmaceutical composition: As used herein, the term "pharmaceutical composition" refers to a composition in which an active agent is formulated together with one or more pharmaceutically acceptable carriers. In some embodiments, the composition is suitable for administration to a human or animal subject. In some embodiments, the active agent is present in unit dose amount appropriate for administration in a therapeutic regimen that shows a statistically significant probability of achieving a predetermined therapeutic effect when administered to a relevant population.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Prevent or prevention: as used herein when used in connection with the occurrence of a disease, disorder, and/or condition, refers to reducing the risk of developing the disease, disorder and/or condition and/or to delaying onset and/or severity of one or more characteristics or symptoms of the disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Recombinant: as used herein, is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc).

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically Effective Amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy such as a pancreatic carcinoma or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence. In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid.

Vector: as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual* ($2^{nd}$ ed., Cold Spring Harbor Laboratory Press, Cold Spring Harbor, N.Y. (1989)), which is incorporated herein by reference for any purpose.

DETAILED DESCRIPTION OF EXEMPLARY EMBODIMENTS

The present disclosure relates, inter alia, to 4-1BB, which is an inducible co-stimulatory molecule, and therapeutic antibodies that bind thereto that have been engineered to have improved characteristics over a reference anti-4-1BB antibody. For example, engineered antibodies provided herein have been modified to enhance antigen affinity relative to that of a reference agonist antibody that specifically recognizes an epitope within the extracellular domain of human 4-1BB (Korean Patent No. 10-0500286, Accession No: KCTC 0952BP). Specifically, as described herein, the inventors engineered a reference humanized anti-human 4-1BB antibody, 94G1 (U.S. Pat. No. 7,932,045). As described examples herein, the light chain and heavy chain CDR sequences of a reference antibody 94G1, were separately engineered to improve the affinity of each chain. Moreover, as described herein, exemplary engineered anti-4-1BB antibodies can effectively induce proliferation of activated T cells. Notably, exemplary engineered anti-4-1BB antibodies are capable of inducing surprisingly improved activity of $CD8^+$ T cells due to the stimulation caused by the 4-1BB humanized antibody binding to a 4-1BB molecule and inhibiting activation-induced cell death (AICD). Thus the present disclosure provides engineered anti-human 4-1BB antibodies with improved properties over a reference antibody, and moreover demonstrate that these antibodies have surprisingly beneficial activity in vitro and in vivo.

4-1BB 4-1BB (also referred to as CD137, TNFRSF9, etc) is a receptor belonging to the tumor necrosis factor receptor (TNFR) superfamily. 4-1BB is a co-stimulatory molecule generally expressed in activated T lymphocytes and involved in immunity and autoimmune diseases (Kwon et al. *PNAS* 84:2896, 1987; Kwon et al. *PNAS* (1989) 86:1963; Son et al. *Journal of Immunological Methods* (2004) 286 (1-2): 187-201, each of which is herein incorporated by reference in its entirety). Human 4-1BB is a 255 amino acid protein (Accession No. NM_001561; NP_001552). The complete human 4-1BB amino acid sequence is provided in SEQ ID NO: 44. 4-1BB is expressed on the cell surface in monomer (30 kDa) and dimer (55 kDa) forms and likely trimerizes with 4-1BB ligand to signal.

Current understanding of 4-1BB suggests that it is constitutively expressed on a number of cells, albeit at low levels, including $Foxp3^+$ Tregs and dendritic cells (DC). (See, Vinay and Kwon (2014) *BMB Rep.* 47(3): 122-129, which is incorporated by reference herein.) Activation with a number of agonists, such as cytokines (e.g., IL-2, IL-4), polyclonal activators (e.g., Con A and PHA), cell surface molecules (e.g., anti-CD3 and anti-CD28) and promoters of $Ca^{2+}$ induction and PKC activity (e.g., ionomycin and photbol myristate acetate) further enhance expression of 4-1BB. Id.

Numerous studies of murine and human T cells indicate that 4-1BB promotes enhanced cellular proliferation, survival, and cytokine production (Croft, 2009, *Nat. Rev. Immunol.* 9:271-285). Studies have indicated that some 4-1BB agonist monoclonal antibodies can increase costimulatory molecule expression and markedly enhance cytolytic T lymphocyte responses, resulting in anti-tumor efficacy in various models. 4-1BB agonist monoclonal antibodies have demonstrated efficacy in prophylactic and therapeutic settings. Further, 4-1BB monotherapy and combination therapy tumor models have established durable anti-tumor protective T cell memory responses (Lynch (2008) *Immunol. Rev.* 22: 277-286). 4-1BB agonists also have been shown to inhibit autoimmune reactions in a variety of art-recognized autoimmunity models (Vinay (2006) *J Mol. Med.* 84:726-736). This dual activity of 4-1BB offers the potential to provide anti-tumor activity while dampening autoimmune side effects that can be associated with immunotherapy approaches.

4-1BB Antibodies and Fragments Thereof

The present disclosure provides, at least in part, engineered anti-human 4-1BB antibodies and fragments thereof that exhibit markedly, and unexpectedly, superior characteristics in vitro and/or in vivo. For example, certain provided antibodies have increased affinity relative to a reference humanized anti-human 4-1BB antibody.

In some embodiments, an anti-4-1BB antibody or antigen-binding antibody fragment includes 1, 2, or 3 heavy chain CDR sequences that are or include a sequence of SEQ ID NOs: 5 to 8. In some embodiments, an anti-4-1BB antibody or antigen-binding antibody fragment includes one or more of: a heavy chain CDR1 that is or includes a sequence of SEQ ID NO: 5, a heavy chain CDR2 that is or includes a sequence of SEQ ID NO: 6 and a heavy chain CDR3 that is or includes a sequence of SEQ ID NO: 7 or 8. In some embodiments, an anti-4-1BB antibody or antigen-binding antibody fragment includes each of: a heavy chain CDR1 that is or includes a sequence of SEQ ID NO: 5, a heavy chain CDR2 that is or includes a sequence of SEQ ID NO: 6 and a heavy chain CDR3 that is or includes a sequence of SEQ ID NO: 7 or 8.

In some embodiments, an anti-4-1BB antibody or antigen-binding antibody fragment includes 1, 2, or 3 light chain CDR sequences that are or include a sequence of SEQ ID NOs: 1-4. In some embodiments, an anti-4-1BB antibody or antigen-binding antibody fragment includes one or more of: a light chain CDR1 that is or includes a sequence of SEQ ID NO: 1, a light chain CDR2 that is or includes a sequence of SEQ ID NO: 2 and a light chain CDR3 that is or includes a sequence of SEQ ID NO: 3 or 4. In some embodiments, an anti-4-1BB antibody or antigen-binding antibody fragment includes each of: a light chain CDR1 that is or includes a sequence of SEQ ID NO: 1, a light chain CDR2 that is or includes a sequence of SEQ ID NO: 2 and a light chain CDR3 that is or includes a sequence of SEQ ID NO: 3 or 4.

In some embodiments, an anti-4-1BB antibody or antigen-binding antibody fragment includes a heavy chain variable domain that includes a heavy chain CDR1 that is or includes a sequence of SEQ ID NO: 5, a heavy chain CDR2 that is or includes a sequence of SEQ ID NO: 6 and a heavy chain CDR3 that is or includes a sequence of SEQ ID NO: 7 or 8 and/or a light chain variable domain that includes a light chain CDR1 that is or includes a sequence of SEQ ID NO: 1, a light chain CDR2 that is or includes a sequence of SEQ ID NO: 2 and a light chain CDR3 that is or includes a sequence of SEQ ID NO: 4.

In some embodiments, an anti-4-1BB antibody or antigen-binding antibody fragment includes a heavy chain variable domain that includes a heavy chain CDR2 that is or includes a sequence of SEQ ID NO: 6 where the $5^{th}$ amino acid, asparagine (N), was substituted with glutamine (Q), glutamic acid (E) or serine (S). In some embodiments, an anti-4-1BB antibody or antigen-binding antibody fragment includes a heavy chain variable domain that includes a heavy chain CDR2 that is or includes a sequence of SEQ ID NO: 6 where the $5^{th}$ amino acid, asparagine (N), was substituted with valine (V), glycine (G), or proline (P).

In some embodiments, an anti-4-1BB antibody or antigen-binding antibody fragment includes a light chain variable domain that includes a light chain CDR3 that is or includes a sequence of SEQ ID NO: 3 or 4 where the $6^{th}$ amino acid position of LCDR3 is mutated.

In some embodiments, an anti-4-1BB antibody or antigen-binding antibody fragment includes a heavy chain variable domain that includes a heavy chain framework 1 (FR1) region comprising a sequence of SEQ ID NO: 16 or 17. In some embodiments, an anti-4-1BB antibody or antigen-binding antibody fragment includes a heavy chain variable domain that includes a heavy chain framework 3 (FR3) region comprising a sequence of any one of SEQ ID NOs: 18-20. In some embodiments, an anti-4-1BB antibody or antigen-binding antibody fragment includes a heavy chain variable domain that includes a heavy chain framework 1 (FR1) region comprising a sequence of SEQ ID NO: 16 or 17 and a heavy chain framework 3 (FR3) region comprising a sequence of any one of SEQ ID NOs: 18-20.

In some embodiments, an anti-4-1BB antibody or antigen-binding antibody fragment includes substantial homology to an antibody or antibody fragment that includes a heavy chain variable domain that is or includes a sequence selected from SEQ ID NOs: 11-14. In some embodiments, an anti-4-1BB antibody or antigen-binding antibody fragment includes a heavy chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 11-14. In some embodiments, an anti-4-1BB antibody or antigen-binding antibody fragment includes a heavy chain variable domain that is or includes a sequence selected from SEQ ID NOs: 11-14.

In some embodiments, an anti-4-1BB antibody or antigen-binding antibody fragment includes substantial homology to an antibody or antibody fragment that includes a light chain variable domain that has or includes a sequence of SEQ ID NO: 9 or 10. In some embodiments, an anti-4-1BB antibody or antigen-binding antibody fragment includes a light chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence of SEQ ID NO: 9 or 10. In some embodiments, an anti-4-1BB antibody or antigen-binding antibody fragment includes a light chain variable domain that is or includes a sequence of SEQ ID NO: 9 or 10.

In some embodiments, an anti-4-1BB antibody or antigen-binding antibody fragment includes substantial homology to an antibody or antibody fragment that includes a heavy chain variable domain that is or includes a sequence selected from SEQ ID NOs: 11-14 and a light chain variable domain that is or includes a sequence of SEQ ID NO: 10. In some embodiments, an anti-4-1BB antibody or antigen-binding antibody fragment includes a heavy chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 11-14 and a light chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence of SEQ ID NO: 10. In some embodiments, an anti-4-1BB antibody or antigen-binding antibody fragment includes a heavy chain variable domain that is or includes a sequence selected from SEQ ID NOs: 11-14 and a light chain variable domain that is or includes a sequence of SEQ ID NO: 10.

Amino acid sequences of anti-human 4-1BB antibody or antigen-binding fragment binds of the present disclosure may be substituted through conservative substitution. The term "conservative substitution" used herein refers to modification of a polypeptide in which one or more amino acids are substituted with an amino acid having a similar biochemical property so as not to cause the loss of a biological or biochemical function of the corresponding polypeptide. The term "conservative sequence variant" or "conservative amino acid substitution" used herein is the substitution of an amino acid residue with an amino acid residue having a similar side chain. Amino acid residues having a similar side chain are defined in the art. Those residues encompass amino acids with a basic side chain (e.g., lysine, arginine, and histidine), amino acids with an acidic side chain (e.g., aspartic acid and glutamate), amino acids with a non-charged polar side chain (e.g., glycine, asparagine, glutamine, serine, threonine, tyrosine, and cysteine), amino acids with a non-polar side chain (e.g., alanine, valine, leucine, isoleucine, proline, phenylalanine, methionine, and tryptophan), amino acids with a beta-branched side chain (e.g., threonine, valine, and isoleucine) and amino acids with an aromatic side chain (e.g., tyrosine, phenylalanine, tryptophan, and histidine). Therefore, it is expected that the antibody of the present invention can have conservative amino acid substitution, and still ensure an activity.

In some embodiments, an anti-human 4-1BB antibody or antigen-binding fragment of the present disclosure may include a constant region selected from an IgG1 constant domain, an IgG2 constant domain, an IgG1/IgG2 hybrid constant domain, a human IgG4 constant domain, an IgA constant domain, an IgE constant domain, an IgM constant domain, and an IgD constant domain.

In some embodiments, an anti-human 4-1BB antibody or antigen-binding fragment of the present disclosure is or includes an IgA, IgD, IgE, IgM, IgG, or variants thereof.

In some embodiments, an anti-human 4-1BB antibody of the present disclosure includes a variant Fc-region that has an amino acid mutations and/or substitutions at one or more positions of 234, 235, 236, 237, 238, 239, 253, 254, 265, 266, 267, 268, 269, 270, 288, 297, 298, 299, 307, 311, 322, 327, 328, 329, 330, 331, 332, 434 and 435.

In some embodiments, an anti-human 4-1BB antibody or antigen-binding fragment of the present disclosure is human IgG1 isotype. In some embodiments, an anti-human 4-1BB antibody or antigen-binding fragment of the present disclosure includes a variant IgG1. In some embodiments, an anti-human 4-1BB antibody or antigen-binding fragment includes an IgG1 polypeptide that has amino acid mutation at one or more positions of 233, 234, 235, 236, 265, 297, 329, 331 and 322.

In some embodiments, an anti-human 4-1BB antibody or antigen-binding fragment includes an IgG1 polypeptide containing one or more mutations in L234, L235, D270, N297, E318, K320, K322, P331 and P329. In some embodiments, an anti-human 4-1BB antibody or antigen-binding fragment includes an IgG1 polypeptide containing two, three, four, or more mutations in L234, L235, D270, N297, E318, K320, K322, P331 and P329. In some embodiments, an anti-human 4-1BB antibody or antigen-binding fragment includes an IgG1 polypeptide with mutations in L234A and L235A.

In some embodiments, an anti-human 4-1BB antibody or antigen-binding fragment includes a light chain constant region. In some embodiments, an anti-human 4-1BB antibody or antigen-binding fragment includes a kappa (κ) and/or lambda (λ) light chain and/or a variant thereof.

In some embodiments, an anti-human 4-1BB antibody or antigen-binding fragment is a monoclonal antibody. In some embodiments, an anti-human 4-1BB antibody or antigen-binding fragment is a Fab fragment, a Fab' fragment, a F(ab')2 fragment, a Fv fragment, a disulfide-bonded Fv fragment, a scFv fragment, a single domain antibody, humabody, nanobody, and/or a diabody. In some embodiments, an anti-human 4-1BB antibody or antigen-binding fragment is a monovalent antibody. In some embodiments, an anti-human 4-1BB antibody or antigen-binding fragment is a multivalent antibody. In some embodiments, an anti-human 4-1BB antibody or antigen-binding fragment is a multispecific antibody (e.g., a bispecific antibody).

In some embodiments, the present disclosure encompasses methods of modifying the carbohydrate content of an antibody of the disclosure by adding or deleting a glycosylation site. Methods for modifying the carbohydrate content of antibodies are well known in the art and encompassed within the disclosure, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the present disclosure encompasses methods of modifying the carbohydrate content of an antibody of the present disclosure by deleting one or more endogenous carbohydrate moieties of the antibody. In a specific embodiment, the present disclosure encompasses deleting the glycosylation site of the Fc region of an antibody, by modifying position 297 from asparagine to alanine. In some embodiments, an anti-human 4-1BB antibody or antigen-binding fragment comprises a N297A mutation in the CH2 domain. In some embodiments, the N297A mutation results in aglycosylation, which reduces FcR or C1q binding. In some embodiments, an anti-human 4-1BB antibody or antigen-binding fragment comprises a heavy chain comprising an Fc region comprising a N297A mutation and a K322A mutation. In some embodiments, an anti-human 4-1BB antibody or antigen-binding fragment comprises a heavy chain comprising an Fc region comprising a N297A mutation and a D265A mutation. In some embodiments, an anti-human 4-1BB antibody or antigen-binding fragment comprises a heavy chain comprising an Fc region comprising a N297A mutation, a D265A mutation, and a K322A mutation. In some embodiments, an anti-human 4-1BB antibody or antigen-binding fragment comprises an Fc region with a L234A mutation and/or a L235A mutation. In some embodiments, an anti-human 4-1BB antibody or antigen-binding fragment comprises an Fc region with one or more mutations selected from L234A-, L235A, N297A, D265A, and K322A. In some embodiments, an anti-human 4-1BB antibody or antigen-binding fragment comprises Fc region with two or more mutations selected from L234A-, L235A, N297A, D265A, and K322A. In some embodiments, an anti-human 4-1BB antibody or antigen-binding fragment comprises Fc region with three, four, or five mutations selected from L234A-, L235A, N297A, D265A, and K322A.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, *Nat. Biotechnol* 17:176-180; Davies et al., 20017 *Biotechnol Bioeng* 74:288-294; Shields et al, 2002, *J Biol Chem* 277:26733-26740; Shinkawa et al., 2003, *J Biol Chem* 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., WO 00061739; EA01229125; US 20030115614; Okazaki et al., 2004, *JMB*, 336: 1239-49 each of which is incorporated herein by reference in its entirety.

In some embodiments, an anti-human 4-1BB antibody or antigen-binding fragment of the present disclosure is as an agonist for human 4-1BB.

In some embodiments, an anti-human 4-1BB antibody or antigen-binding fragment of the present disclosure binds to a human 4-1 BB molecule. In some embodiments, an anti-human 4-1BB antibody or antigen-binding fragment of the present disclosure specifically binds to a human 4-1 BB molecule.

In some embodiments, an anti-human 4-1BB antibody or antigen-binding fragment binds to a sequence that is or includes that of SEQ ID NO: 15. In some embodiments, an anti-human 4-1BB antibody or antigen-binding fragment binds to an epitope of 4-1BB extracellular domain that is or includes a sequence of SEQ ID NO: 15.

In some embodiments, binding of an anti-human 4-1BB antibody or antigen-binding fragment of the present disclosure with human 4-1BB extracellular domain is abrogated by one or more mutations of SEQ ID NO: 44 selected from N30, D38, N39, R41, A56, G57, R60 or T61.

In some embodiments, an anti-human 4-1BB antibody or antigen-binding fragment of the present disclosure binds to a human 4-1 BB molecule with a binding affinity ($K_D$) of $1 \times 10^{-7}$ to $1 \times 10^{-12}$ M. In some embodiments, an anti-human 4-1BB antibody or antigen-binding fragment of the present disclosure binds to a human 4-1 BB molecule with a binding affinity ($K_D$) of $1 \times 10^8$ to $1 \times 10^{-12}$ M. Binding affinity ($K_D$) may be measured, for example, by surface plasmon resonance, for example, using a BIACORE system.

In some embodiments, an anti-human 4-1BB antibody or antigen-binding fragment of the present disclosure binds to a human 4-1BB molecule or a fragment thereof at a binding affinity ($K_D$) of less than $1.0 \times 10^{-8}$ M. In some embodiments, an anti-humanized 4-1BB antibody or antigen-binding fragment of the present disclosure binds to a human 4-1BB molecule or a fragment thereof at a binding affinity ($K_D$) of less than $1.0 \times 10^{-9}$ M. In some embodiments, an anti-humanized 4-1BB antibody or antigen-binding fragment of the present disclosure binds to a human 4-1BB molecule or a fragment thereof at a binding affinity ($K_D$) of less than $1.0 \times 10^{-10}$ M.

In some embodiments, an anti-4-1BB antibody or antigen-binding fragment of the present disclosure fails to bind or weakly binds a non-primate 4-1BB polypeptide (e.g., a canine, mouse and rat 4-1BB polypeptide). In some embodiments, an anti-4-1BB antibody or antigen-binding fragment of the present disclosure binds efficiently to human or monkey 4-1BB. This binding affinity suggests that the structure and/or sequence of epitope for a primate 4-1BB antibody may be quite different from canine, mouse and rat.

In some embodiments, an anti-human 4-1BB antibody or antigen-binding fragment of the present disclosure is an agonistic antibody. In some embodiments, an anti-human 4-1BB antibody or antigen-binding fragment of the present disclosure mediates T cell activation. In some embodiments, an anti-human 4-1BB antibody or antigen-binding fragment of the present disclosure binds $CD8^+$ and/or $CD4^+$ T cells expressing human 4-1BB.

In some embodiments, an anti-human 4-1BB antibody or antigen-binding fragment of the present disclosure does not have or has low ADCC activity. In some embodiments, an anti-human 4-1BB antibody or antigen-binding fragment of the present disclosure does not have or has low CDC activity. In some embodiments, an anti-human 4-1BB antibody or antigen-binding fragment of the present disclosure does not have or has low ADCC activity and CDC activity. In some embodiments, an anti-human 4-1BB antibody or antigen-binding fragment of the present disclosure has an ADCC cell killing activity of less than about less than about 20%, less than about 10%, less than about 8%, or less than about 5%. In some embodiments, an anti-human 4-1BB antibody or antigen-binding fragment of the present disclosure has an ADCC cell killing activity of less than about 10%. In some embodiments, an anti-human 4-1BB antibody or antigen-binding fragment of the present disclosure has a CDC cell killing activity of less than about 30%, less than about 20%, less than about 10%, less than about 8%, or less than about 5%. In some embodiments, an anti-human 4-1BB antibody or antigen-binding fragment of the present disclosure has a CDC cell killing activity of less than about 20%.

In some embodiments, an anti-human 4-1BB antibody or antigen-binding fragment of the present disclosure is characterized by low toxicity (e.g., a low degree of post administration cell death). In some embodiments, an anti-human 4-1BB antibody or antigen-binding fragment of the present disclosure is characterized by low hepatoxicity. In some embodiments, a subject that has been administered an anti-human 4-1BB antibody or antigen-binding fragment of the present disclosure at a therapeutic dose has levels of one or more of ALT, AST and total bilirubin in a normal range. In some embodiments, an anti-human 4-1BB antibody or antigen-binding fragment of the present disclosure is characterized by an ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (Elliott et al., Lancet 344:1125-1127 (1994), entirely incorporated herein by reference).

Nucleic Acids

The disclosure provides polynucleotides comprising a nucleotide sequence encoding anti-human 4-1BB antibodies of the present disclosure and fragments thereof. Anti-human 4-1BB antibodies and fragments thereof as described herein may be produced from nucleic acid molecules using molecular biological methods known to the art. Nucleic acids of the present disclosure include, for example, DNA and/or RNA.

In some embodiments, nucleic acid constructs include regions that encode an anti-human 4-1BB antibody or fragment thereof (e.g., 94K, 94 KV, 94KVT, EU101). In some embodiments, such antibodies or fragments thereof will include $V_H$ and/or $V_L$ regions. An anti-human 4-1BB antibody or fragment thereof may be identified and/or selected for a desired binding and/or functional properties, and variable regions of said antibody isolated, amplified, cloned and/or sequenced. Modifications may be made to the $V_H$ and $V_L$ nucleotide sequences, including additions of nucleotide sequences encoding amino acids and/or carrying restriction sites, and/or substitutions of nucleotide sequences encoding amino acids. In some embodiments, a nucleic acid sequence may or may not include an intron sequence.

Where appropriate, nucleic acid sequences that encode anti-human 4-1BB antibodies and fragments thereof (e.g., 94K, 94 KV, 94KVT, EU101) may be modified to include codons that are optimized for expression in a particular cell type or organism (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding antibody components, in whole or in part, may include an altered sequence to optimize codon usage for a particular cell type (e.g., a eukaryotic or prokaryotic cell). For example, a coding sequence for a humanized heavy (or light) chain variable region as described herein may be optimized for expression in a bacterial cells. Alternatively, the coding sequence may be optimized for expression in a mammalian cell (e.g., a CHO cell). Such a sequence may be described as a codon-optimized sequence.

Nucleic acid constructs of the present disclosure may be inserted into an expression vector or viral vector by methods known to the art, and nucleic acid molecules may be operably linked to an expression control sequence. A vector comprising any of the above-described nucleic acid molecules, or fragments thereof, is further provided by the present disclosure. Any of the above nucleic acid molecules, or fragments thereof, can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987)).

In some embodiments, conventionally used techniques, such as, fore example, electrophoresis, calcium phosphate precipitation, DEAE-dextran transfection, lipofection, etc. may be used to introduce a foreign nucleic acid (DNA or RNA) into a prokaryotic or eukaryotic host cell. Desirably, a vector may include regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. In some embodiments, a vector comprises regulatory sequences that are specific to the genus of the host. Preferably, a vector comprises regulatory sequences that are specific to the species of the host.

In addition to the replication system and the inserted nucleic acid, a nucleic acid construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. For example, a cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI110, pBI101.2, pBI101.3, pBI121 and pBIN19 (Clontech). Examples of animal expression vectors include pEUK-C1, pMAM and pMAMneo (Clontech). The TOPO cloning system (Invitrogen, Carlsbad, Calif.) also can be used in accordance with the manufacturer's recommendations.

An expression vector can comprise a native or nonnative promoter operably linked to an isolated or purified nucleic acid molecule as described above. Selection of promoters, e.g., strong, weak, inducible, tissue-specific and developmental-specific, is within the skill in the art. Similarly, combining of a nucleic acid molecule, or fragment thereof, as described above with a promoter is also within the skill in the art.

Suitable viral vectors include, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. These viral vectors can be prepared using standard recombinant DNA techniques described in, for example, Sambrook et al., *Molecular Cloning, a Laboratory Manual*, 2d edition, Cold Spring Harbor Press, Cold Spring Harbor, N.Y. (1989); and Ausubel et al., *Current Protocols in Molecular Biology*, Greene Publishing Associates and John Wiley & Sons, New York, N.Y. (1994).

A retroviral vector is derived from a retrovirus. Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

In some embodiments, nucleic acids and vectors of the present disclosure may be isolated and/or purified. The present disclosure also provides a composition comprising an above-described isolated or purified nucleic acid molecule, optionally in the form of a vector. Isolated nucleic acids and vectors may be prepared using standard techniques known in the art including, for example, alkali/SDS treatment, CsCl binding, column chromatography, agarose gel electrophoresis and other techniques well known in the art. The composition can comprise other components as described further herein.

In some embodiments, nucleic acid molecules are inserted into a vector that is able to express an anti-human 4-1BB antibody or fragment thereof when introduced into an appropriate host cell. Appropriate host cells include, but are not limited to, bacterial, yeast, insect, and mammalian cells. Exemplary host cells include prokaryotes (e.g., E. coli) and eukaryotes (e.g., a COS or a CHO cell). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells (e.g., DG44 cells). In some embodiments, a mammalian host cell suitable for the expression of the antibody may be a Chinese Hamster Ovary (CHO) cell (for example, including DHFR-CHO cells used along with a DHFR-selectable marker), an NSO myeloma cell, a COS cell or an SP2 cell.

Any method(s) known to one skilled in the art for the insertion of DNA fragments into a vector may be used to construct expression vectors encoding an anti-human 4-1BB antibody or fragment thereof of the present disclosure under control of transcriptional/translational control signals. These methods may include in vitro recombinant DNA and synthetic techniques and in vivo recombination (See, e.g., Ausubel, supra; or Sambrook, supra).

Production of Antibodies

Antibodies and antigen-binding fragments of the present invention may be prepared and/or purified by any technique known in the art, which allows for the subsequent formation of a stable antibody or antibody fragment.

A nucleic acid encoding an anti-human 4-1BB antibody and/or antigen-binding fragment of the present disclosure may be easily isolated and sequenced by conventional procedures. For example, an oligonucleotide primer designed to specifically amplify corresponding heavy chain and light chain-coding regions from a hybridoma or phage template DNA may be used. Isolated nucleic acids may be inserted into an expression vector, and then desired monoclonal antibodies may be produced from a suitable host cell (that is, transformant) transformed by introducing the expression vector to the host cell. In some embodiments, a method for preparing anti-human 4-1BB antibody and/or antigen-binding fragment of the present disclosure may include amplifying an expression vector including a nucleic acid encoding the antibody, but is not limited thereto.

In some embodiments, a host cell is eukaryotic host cell, including, for example, yeast, higher plant, insect and mammalian cells. Depending upon the host employed in a recombinant production procedure, antibodies and antibody fragments of the present disclosure can be glycosylated or can be non-glycosylated. In some embodiments, a recombinant expression vector encoding an anti-human 4-1BB antibody and/or antigen-binding fragment of the present disclosure is introduced into a mammalian host cell and an antibody may be prepared by culturing the host cell for a sufficient time to express the antibody. In some embodiments, a mammalian host cell is cultured for a sufficient time to secrete an antibody or antibody fragment of the present disclosure in a culture medium.

In some embodiments, an expressed antibody of the present disclosure may be uniformly purified after being isolated from the host cell. Isolation and/or purification of an antibody of the present disclosure may be performed by a conventional method for isolating and purifying a protein. For example, not wishing to be bound by theory, an anti-human 4-1BB antibody and/or antigen-binding fragment of the present disclosure can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, N.Y., N.Y., (1997-2001), e.g., chapters 1, 4, 6, 8, 9, and 10, each entirely incorporated herein by reference. In some embodiments, an antibody of the present disclosure may be isolated and/or purified by additionally combining filtration, superfiltration, salting out, dialysis, etc.

Purified anti-human 4-1BB antibodies and/or antigen-binding fragments of the present disclosure can be characterized by, for example, ELISA, ELISPOT, flow cytometry, immunocytology, BIACORE™ analysis, SAPIDYNE KINEXA™ kinetic exclusion assay, SDS-PAGE and Western blot, or by HPLC analysis as well as by a number of other functional assays disclosed herein.

Therapeutic Applications

The present disclosure encompasses a recognition that engineered anti-human 4-1BB antibodies and antigen-binding fragments may be useful for diagnosis, prevention, and/or treatment of certain diseases such as, for example, cancer. Any of the anti-4-1BB antibodies or antigen-binding fragments provided herein may be used in therapeutic methods. For example, an anti-4-1BB antibody or antigen-binding fragment of the present disclosure can be used as immunotherapeutic agents, for example in the treatment of a malignant disease (e.g., cancer).

The present disclosure provides methods for treating and/or preventing a malignant disease, said methods including administering an anti-4-1BB antibody or antigen-binding fragment of the present disclosure to a subject. Methods for modulating or treating at least one malignant disease in a cell, tissue, organ, animal or patient, include, but are not limited to, cancer and/or and the treatment of inflammatory diseases.

Cancer treatments in the context of the present disclosure may be mediated through increasing cytotoxic T cells and anti-cancer cytokines. Generally, antigen-specific cell-mediated immunity is caused by cytotoxic T cells, and includes two signaling events: a first signaling event is induced when a T cell recognizes an antigen from an antigen-presenting cell via a receptor, and a second signaling is induced by co-stimulatory molecules. Due to the first and second stimuli, T cell activity and related factors are increased, thereby forming T cells specifically functioning in cancer treatment, and the formed T cells are increased in cytotoxicity, cell division, cell viability and anti-cancer cytokine secretion due to stimulation with the co-stimulatory molecules.

Specifically, it has been demonstrated that stimulation by 4-1BB can enhance the activity of $CD8^+$ T cells, increase secretion of anti-cancer cytokines such as interferon gamma (IFNγ), increase expression of anti-apoptotic molecules such as Bcl-2, BclXL and Bfl-1, and/or inhibits activation-induced cell death (AICD). In some embodiments, an anti-human 4-1BB antibody or antigen-binding fragment of the present disclosure can enhance or increase one or more of $CD8^+$ T cell activity, secretion of anti-cancer cytokines such as interferon gamma (IFNγ), expression of anti-apoptotic molecules such as Bcl-2, BclXL and Bfl-1, and inhibition of activation-induced cell death (AICD). In some embodiments, therapeutic treatment with an anti-human 4-1BB antibody or antigen-binding fragment of the present disclosure can reduce and/or inhibit growth of cancer cells.

In some embodiments, the present disclosure provides a method for delaying or inhibiting tumor growth, comprising regulation of cytokine secretion in vivo or in vitro by administering an anti-human 4-1BB antibody or antigen-binding fragment of the present disclosure. In some embodiments, the present disclosure provides a method for reducing tumor burden, comprising regulation of cytokine secretion in vivo or in vitro by administering an anti-human 4-1BB antibody or antigen-binding fragment of the present disclosure.

In some embodiments, the present disclosure provides a method for treating cancer or tumor by monitoring to a biological subject of cancer or tumor to be treated, comprising: (i) administrating an anti-human 4-1BB antibody or antigen-binding fragment of the present disclosure to a subject, (ii) separating then isolating a biological sample from the subject, (iii) measuring a secretion amount of INFγ or TGFβ from the sample and estimating a proportion ratio and (iv) determining a therapeutically effective amount of the antibody or antigen-binding fragment thereof by comparing the control samples which are administered or not administrated with the anti-human 4-1BB antibody or antigen-binding fragment thereof.

In some embodiments, the present disclosure provides a method of treating a subject in need thereof, the method comprising a step of administering to the subject a composition that comprises or delivers an anti-4-1BB antibody or antigen-binding fragment of the present disclosure and/or a nucleic acid the same. In some embodiments, a subject has or is at risk for developing cancer. In some embodiments, the present disclosure provides a method for preventing or treating cancer or tumor of a patient, which includes administering a therapeutically effective amount of the humanized 4-1BB antibody or the antigen-binding fragment thereof to a patient with cancer or tumor.

In some embodiments, the present disclosure provides a method of inducing an immune response in a subject in need thereof, the method comprising a step of administering to the subject a composition that comprises or delivers an anti-4-1BB antibody or antigen-binding fragment of the present disclosure and/or a nucleic acid the same. In some embodiments, a subject has or is at risk for developing cancer.

In some embodiments, the present disclosure provides a method of enhancing an immune response or increasing the activity of an immune cell in a subject in need thereof, the method comprising a step of administering to the subject a composition that comprises or delivers an anti-4-1BB antibody or antigen-binding fragment of the present disclosure and/or a nucleic acid the same. In some embodiments, a subject has or is at risk for developing cancer.

Cancers suitable for treatment with method of the present disclosure can include, but are not limited to, bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, and prostate cancer. In some embodiments, a cancer for treatment with an anti-4-1BB antibody or antigen-binding fragment of the present disclosure may include, but is not limited to, carcinoma, lymphoma (e.g., Hodgkin's and non-Hodgkin's lymphomas), blastoma, sarcoma and leukemia. In some embodiments, cancer may include squamous cell carcinoma, small cell lung cancer, non-small cell lung cancer, lung adenocarcinoma, squamous cell carcinoma of the lung, peritoneal cancer, hepatocellular carcinoma, gastric cancer, pancreatic cancer, glioma, cervical cancer, ovarian cancer, liver cancer, bladder cancer, hepatocellular carcinoma, breast cancer, colon cancer, colorectal cancer, endometrial or uterine carcinoma, salivary carcinoma, kidney cancer, prostate cancer, vulvar cancer, thyroid cancer, liver carcinoma, leukemia and other lymphoproliferative disorders, and various types of head and neck cancer.

A composition including an anti-4-1BB antibody or antigen-binding fragment of the present disclosure may be administered at a pharmaceutically effective amount to treat cancer cells or metastasis thereof, or inhibit the growth of cancer. For use in therapeutic methods, an anti-4-1BB antibody or antigen-binding fragment of the present disclosure would be formulated, dosed, and administered in a fashion consistent with good medical practice. Factors for consideration in this context include the particular disorder being treated, the particular mammal being treated, the clinical condition of the individual patient, the age of the patient, the weight of the patient, the cause of the disorder, the site of delivery of the agent, the method of administration, the scheduling of administration, and other factors known to medical practitioners.

The present disclosure provides high affinity anti-human 4-1BB antibodies that may have superior properties relative to a reference antibody. The present disclosure encompasses a recognition that these antibodies may have improved ability to induce T cell activation and/or secretion of cytokines such as IFNγ. Accordingly, the present disclosure encompasses a recognition that an anti-human 4-1BB antibody or antigen binding fragment of the present disclosure may be administered a dose lower than reference antibody.

In some embodiments composition that includes an anti-4-1BB antibody or antigen-binding fragment of the present disclosure may be administered to a patient as a bolus or by continuous injection when needed. In some embodiments, bolus administration is of an anti-4-1BB Fab of the present disclosure and may be administered at a dose of 0.0025 to 100 mg/kg, 0.025 to 0.25 mg/kg, 0.010 to 0.10 mg/kg, or 0.10 to 0.50 mg/kg. In the case of the continuous injection, the antibody of the present invention presented as a Fab fragment may be administered at a dose of 0.001 to 100 mg/kg/min, 0.0125 to 1.25 mg/kg/min, 0.010 to 0.75 mg/kg/min, 0.010 to 1.0 mg/kg/min or 0.10 to 0.50 mg/kg/min for 1 to 24 hours, 1 to 12 hours, 2 to 12 hours, 6 to 12 hours, 2 to 8 hours, or 1 to 2 hours. In some embodiment, an antibody of the present disclosure is a full-length antibody (having a complete constant domain). In some embodiments, a full-length antibody is administered at a dose of approximately 0.01 to 10 mg/kg, 1 to 8 mg/kg, or 2 to 6 mg/kg. In some embodiments, a full-length antibody is administered by injection for 30 to 35 minutes. Administration frequency may vary depending on the severity of a condition. For example, the frequency may be once every 2 to 7 days, once a week, or once every 1, 2, 3 or 4 weeks.

In some embodiments, a composition may be administered to a patient by subcutaneous injection. Specifically, the antibody may be administered to a patient at a dose of 0.1 to 100 mg by subcutaneous injection once every 2 to 7 days, every week, once every two weeks, or every month.

Combination Therapies

The present disclosure provides therapeutic methods that include administration of an anti-human 4-1BB antibody or antigen-binding fragment of the present disclosure in combination with one or more other therapies.

In some embodiments, an anti-human 4-1BB antibody or antigen-binding fragment is administered in combination with one or more therapies that have been approved for treatment of cancer. For example, combination treatment of with an anti-4-1BB antibody and a conventional chemotherapeutic, cisplatin, has been shown to have synergistic activity in tumor killing and prevention of organ-specific toxicity-. (Kim et al., Cancer Research (2008) 68(18):7264-9)

In some embodiments, an anti-human 4-1BB antibody or antigen-binding fragment of the present disclosure is administered in combination with a second therapy selected from an immune checkpoint inhibitor, Interleukin 12 (IL-12), Granulocyte-macrophage colony-stimulating factor (GM-CSF), an anti-CD4 agent, and a chemotherapeutic agent, such that the subject receives treatment with both.

In some embodiments, an anti-human 4-1BB antibody or antigen-binding fragment of the present disclosure is administered to a subject that been administered or will be administered a composition comprising a chemotherapeutic agent, such that the subject receives treatment with both. Therapeutic methods of the present disclosure may include administration of any chemotherapeutic agent known in the art. In some embodiments, chemotherapeutic agent is administered to a subject that been administered or will be administered a composition comprising an anti-human 4-1BB antibody or antigen-binding fragment.

In some embodiments, an anti-human 4-1BB antibody or antigen-binding fragment is administered to a subject that been administered or will be administered a composition comprising fluorouracil. In some embodiments, fluorouracil is administered to a subject that been administered or will be administered a composition comprising an anti-human 4-1BB antibody or antigen-binding fragment. In some embodiments, an anti-human 4-1BB antibody or antigen-binding fragment is administered to a subject that been administered or will be administered a composition comprising doxorubicin. In some embodiments, doxorubicin is administered to a subject that been administered or will be administered a composition comprising an anti-human 4-1BB antibody or antigen-binding fragment. In some embodiments, an anti-human 4-1BB antibody or antigen-binding fragment is administered to a subject that been administered or will be administered a composition comprising irinotecan. In some embodiments, irinotecan is administered to a subject that been administered or will be administered a composition comprising an anti-human 4-1BB antibody or antigen-binding fragment. In some embodiments, an anti-human 4-1BB antibody or antigen-binding fragment is administered to a subject that been administered or will be administered a composition comprising paclitaxel. In some embodiments, paclitaxel is administered to a subject that been administered or will be administered a composition comprising an anti-human 4-1BB antibody or antigen-binding fragment.

In some embodiments, an anti-human 4-1BB antibody or antigen-binding fragment is administered to a subject that been administered or will be administered a composition comprising cisplatin. In some embodiments, cisplatin is administered to a subject that been administered or will be administered a composition comprising an anti-human 4-1BB antibody or antigen-binding fragment. In some embodiments, an anti-human 4-1BB antibody or antigen-binding fragment is administered to a subject that been administered or will be administered a composition comprising cyclophosphamide. In some embodiments, cyclophosphamide is administered to a subject that been administered or will be administered a composition comprising an anti-human 4-1BB antibody or antigen-binding fragment.

In some embodiments, an anti-human 4-1BB antibody or antigen-binding fragment of the present disclosure is administered to a subject that been administered or will be administered a composition comprising GM-CSF, such that the subject receives treatment with both. In some embodiments, GM-CSF is administered to a subject that been administered or will be administered a composition comprising an anti-human 4-1BB antibody or antigen-binding fragment.

In some embodiments, an anti-human 4-1BB antibody or antigen-binding fragment of the present disclosure is administered to a subject that been administered or will be administered a composition comprising IL-12, such that the subject receives treatment with both. In some embodiments, IL-12 is administered to a subject that been administered or will be administered a composition comprising an anti-human 4-1BB antibody or antigen-binding fragment.

In some embodiments, an anti-human 4-1BB antibody or antigen-binding fragment of the present disclosure is administered to a subject that been administered or will be administered a composition comprising an anti-CD4 agent, such that the subject receives treatment with both. In some embodiments, an anti-CD4 agent is administered to a subject that been administered or will be administered a composition comprising an anti-human 4-1BB antibody or antigen-binding fragment.

In some embodiments, an anti-human 4-1BB antibody or antigen-binding fragment of the present disclosure is administered to a subject that been administered or will be administered a composition comprising a checkpoint inhibitor (e.g., an immune checkpoint inhibitor), such that the subject receives treatment with both. In some embodiments, an immune checkpoint inhibitor is administered to a subject that been administered or will be administered a composition comprising an anti-human 4-1BB antibody or antigen-binding fragment.

A checkpoint inhibitor used in combination with an anti-human 4-1BB antibody or antigen-binding fragment of the present disclosure can be, for example, any immune checkpoint inhibitor. Examples of inhibitory checkpoint molecules include A2AR, B7-H3, B7-H4, BTLA, CTLA-4, CD277, IDO, KIR, PD-1, LAG-3, TIM-3, TIGIT and VISTA. An immune checkpoint inhibitor may refer to any compound that inhibits the function of an immune inhibitory checkpoint protein. Inhibition includes reduction of function and full blockade. In some embodiments, an immune checkpoint inhibitor is an antibody that specifically recognizes an immune checkpoint protein. A number of immune checkpoint inhibitors are known and in analogy of these known immune checkpoint protein inhibitors, alternative immune checkpoint inhibitors may be developed in the (near) future. Immune checkpoint inhibitors include, but are not limited to, peptides, antibodies, nucleic acid molecules and small molecules.

In some embodiments, an immune checkpoint inhibitor is an inhibitor of CTLA-4. In some embodiments, a checkpoint inhibitor is an antibody that targets CTLA-4, such as, for example, ipilimumab. In some embodiments, a checkpoint inhibitor also targets CD366, which is a transmembrane protein also known as T cell immunoglobulin and mucin domain containing protein-3 (TIM-3). In some embodiments, an immune checkpoint inhibitor is an agent that inhibits PD-1 signaling.

PD-1 (i.e. programmed cell death protein-1), is a protein that is distributed on the surface of an immune cell such as a T or B cell and is also known as CD279. In a human, PD-1 is expressed by a PDCD1 gene located at the 2p37.3 position on chromosome 2. PD-1 is known to bind two ligands, PD-L1 and PD-L2.

In some embodiments, an anti-PD-1 agent is administered to patient who is receiving, has received or will receive treatment with an anti-human 4-1BB antibody or antigen-binding fragment of the present disclosure. In some certain embodiments, an anti-human 4-1BB antibody or antigen-binding fragment of the present disclosure is administered to patient who is receiving, has received or will receive treatment with an anti-PD-1 agent.

In some embodiments, an anti-PD-L1 agent is administered to patient who is receiving, has received or will receive treatment with an anti-human 4-1BB antibody or antigen-binding fragment of the present disclosure. In some certain embodiments, an anti-human 4-1BB antibody or antigen-binding fragment of the present disclosure is administered to patient who is receiving, has received or will receive treatment with an anti-PD-L1 agent. In some embodiments, agents that inhibit PD-L1 include, for example, AMP-244, MEDI-4736, MPDL328 OA, MIH1.

In some embodiments, an anti-PD-1 agent is an agent that inhibits PD-1. In some embodiments, an anti-PD-1 agent is an agent that inhibits PD-L1 and/or PD-L2. In some embodiments, an antibody agent that inhibits PD-1 signaling is a monoclonal antibody or a fragment thereof. In some embodiments, an antibody agent that inhibits PD-1 signaling is an anti-PD-1 antibody or fragment thereof.

In some embodiments, an anti-PD-1 antibody is administered to patient who is receiving, has received or will receive treatment with an anti-human 4-1BB antibody or antigen-binding fragment of the present disclosure. In some certain embodiments, an anti-human 4-1BB antibody or antigen-binding fragment of the present disclosure is administered to patient who is receiving, has received or will receive treatment with an anti-PD-1 antibody. Anti-PD-1 antibodies include, for example, nivolumab, pembrolizumab, atezolizumab, durvalumab, and avelumab. Pembrolizumab (Keytruda, Merck) is an antibody therapeutic that inhibits PD-1 activity.

As described in the Examples of the present application, administration of an anti-human 4-1BB antibody or antigen-binding fragment of the present disclosure in combination with an anti-PD-1 antibody may enhance efficacy relative to either treatment alone, and further may also reduce conventionally known side effects.

In some certain embodiments, pembrolizumab is administered to patient who is receiving, has received or will receive treatment with an anti-human 4-1BB antibody or antigen-binding fragment of the present disclosure. In some certain embodiments, an anti-human 4-1BB antibody or antigen-binding fragment of the present disclosure is administered to patient who is receiving, has received or will receive treatment with pembrolizumab.

In some embodiments, an immune checkpoint inhibitor (e.g., an anti-PD-1 agent) is administered to a patient in an amount of from about 0.01 mg/kg to about 100 mg/kg. In some embodiments, an immune checkpoint inhibitor (e.g., an anti-PD-1 agent) is administered to a patient in an amount within a range bounded by a lower limit and an upper limit, the upper limit being larger than the lower limit. In some embodiments, the lower limit may be about 0.01 mg/kg, 0.025 mg/kg, 0.05 mg/kg, 0.075 mg/kg, 0.1 mg/kg, 0.25 mg/kg, 0.5 mg/kg, 0.75 mg/kg, 1 mg/kg, 2 mg/kg, 3 mg/kg, 4 mg/kg, 5 mg/kg, 8 mg/kg, 10 mg/kg, 20 mg/kg, 25 mg/kg, 30 mg/kg, 40 mg/kg, 50 mg/kg, 50 mg/kg, 70 mg/kg, 80 mg/kg, or 90 mg/kg. In some embodiments, the upper limit may be about 0.025 mg/kg, 0.05 mg/kg, 0.075 mg/kg, 0.1 mg/kg, 0.25 mg/kg, 0.5 mg/kg, 0.75 mg/kg, 1 mg/kg, 2 mg/kg, 3 mg/kg, 4 mg/kg, 5 mg/kg, 8 mg/kg, 10 mg/kg, 20 mg/kg, 25 mg/kg, 30 mg/kg, 40 mg/kg, 50 mg/kg, 50 mg/kg, 70 mg/kg, 80 mg/kg, 90 mg/kg, or 100 mg/kg. In some embodiments, an immune checkpoint inhibitor (e.g., an anti-PD-1 agent) may be administered to a patient in an amount of from about 1 mg/kg to about 20 mg/kg, from about 1 mg/kg to about 10 mg/kg, from about 1 mg/kg to about 5 mg/kg, from about 2 mg/kg to about 5 mg/kg, from about 2 mg/kg to about 4 mg/kg, from about 3 mg/kg to about 5 mg/kg, or from about 3 mg/kg to about 4 mg/kg. In some embodiments, an immune checkpoint inhibitor (e.g., an anti-PD-1 agent) may be administered to a patient in an amount of about 1 mg/kg, about 2 mg/kg, about 3 mg/kg, about 4 mg/kg, or about 5 mg/kg.

In some embodiments, treatment with a combination of an immune checkpoint inhibitor and an anti-human 4-1BB antibody or antigen-binding fragment of the present disclosure may enhance proliferation, migration, persistence and/or cytoxic activity of $CD8^+$ T cells in a subject.

Cell-Based Applications

Yet another object of the present invention is to provide a method for proliferating activated T cells ex vivo by administering the 4-1BB humanized antibody or antigen-binding fragment thereof.

In some embodiments, a method for ex vivo proliferation and/or isolation of activated T cells includes contacting a population of T cells with an anti-4-1BB antibody or antigen-binding fragment of the present disclosure, thereby increasing proliferation of activated T cells.

In some embodiments, a method for proliferating activated T cells ex vivo includes administering an anti-4-1BB antibody or antigen-binding fragment of the present disclosure. In some embodiments, activated T cells are proliferated and/or isolated from a sample of peripheral blood mononuclear cells (PBMC). PBMCs can be obtained/isolated using methods known in the art.

In some embodiments, a method for ex vivo proliferation and/or isolation of activated T cells includes administration of an anti-CD3 monoclonal antibody to the culture medium (e.g., at a concentration of at least about 0.5 ng/ml). In some embodiments, a method for ex vivo proliferation and/or isolation of activated T cells includes administration of IL-2 and/or IL-15 to the culture medium (e.g., at concentration that is at least about 10 units/ml).

In some embodiments, a method for isolating antigen-specific activated T cells includes (a) culturing peripheral blood mononuclear cells (PBMC) in a medium together with a peptide of an epitope of interest and IL-2; (b) inducing 4-1BB expression in the cultured cells by adding the peptide of the epitope of interest; (c) contacting the cultured cells with a surface coated with an anti-4-1BB antibody or antigen-binding fragment, wherein cultured cells expressing 4-1BB adhere to the coated surface; and (d) removing unattached cells, thereby isolating antigen-specific activated T cells.

In some embodiments, the activated T cells are CD8+ T cells.

In some embodiments, lymphocytes (e.g., T cells) are cultured at a temperature of at least about 25° C., preferably at least about 30° C., more preferably about 37° C.

The present disclosure encompasses the recognition that activated T cells (e.g., CD8+ T cells), generated by the methods described herein may be therapeutically useful (e.g., for the treatment of cancer).

Cell-Based Therapies

The present disclosure provides methods to selectively isolate and mass culture CD8+ T cells which recognize an autologous cancer antigen (self-tumor antigen), for example, an autologous cancer antigen that overexpressed in cancer cells while present in a low ratio in normal cells. The present disclosure that cells (e.g., CD8+ T) isolated by these methods may be useful for the treatment of cancer.

In some embodiments, a method for treating and/or preventing cancer in a subject in need thereof includes administering to the subject a therapeutically effective amount of activated T cells produced by an ex vivo method such as those described herein.

Upon appropriate reactivation, tumor antigen specific T cells can recognize and eliminate autologous tumor cells. For example, tumor antigen specific T cells can be generated ex vivo using methods as described herein. Upon adoptive transfer, specifically reactivated T cells from cancer patients can efficiently reject autologous human tumors in vivo.

The present disclosure provides methods for preventing and/or treating cancer and/or tumor of a patient, which include administering a therapeutically effective amount of activated T cells prepared ex vivo by administering an anti-4-1BB antibody or antigen-binding fragment of the present disclosure.

In some embodiments, T cells for using in a therapeutic method are allogenic (from the same species but different donor) as the recipient subject. In some embodiments, T cells for using in a therapeutic method are autologous (the donor and the recipient are the same). In some embodiments, T cells for using in a therapeutic method are syngeneic (the donor and the recipients are different but are identical twins).

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective amount of cells in the composition is at least $10^8$, typically greater than $10^8$, at least $10^9$ cells, and generally more than $10^{10}$. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less. In some embodiments, cells for administration are in a volume of less than 500 ml, less than 250 ml, or 100 ml or less. In some embodiments, a density of the desired cells is typically greater than $10^6$ cells/ml and generally is greater than $10^7$ cells/ml, generally $10^8$ cells/ml or greater. A clinically relevant number of immune cells can be apportioned into multiple infusions that cumulatively equal or exceed $10^8$ cells, $10^9$ cells, $10^{10}$ cells. $10^{11}$ cells, or $10^{12}$ cells.

Compositions

Provided herein are compositions comprising antibodies and antigen binding fragments that specifically bind to an epitope of a human 4-1BB polypeptide. Compositions of the present disclosure (e.g., compositions that deliver an anti-human 4-1BB antibody or antibody fragment) may include any suitable and effective amount of a composition for use in delivering a provided anti-human 4-1BB antibody or antibody fragment to a cell, tissue, organ, animal or patient in need of such modulation, treatment or therapy. Also provided herein are compositions that include activated cell populations (e.g., activated T cell population) that have been generated via a method of the present disclosure (e.g., a method that includes a step contacting a cell with an anti-human 4-1BB antibody or antibody fragment).

Compositions of the present disclosure include pharmaceutical compositions that include an anti-human 4-1BB antibody or antigen-binding fragment disclosed herein and/or a cell population obtained by a method disclosed herein. In some embodiments, a pharmaceutical composition can include a buffer, a diluent, an excipient, or any combination thereof. In some embodiments, a composition, if desired, can also contain one or more additional therapeutically active substances.

In some embodiments, an anti-4-1BB antibody, antigen-binding fragment and/or cell population of the present disclosure are suitable for administration to a mammal (e.g., a human). Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

In some embodiments, compositions are formulated for parenteral administration. For example, a pharmaceutical composition provided herein may be provided in a sterile injectable form (e.g., a form that is suitable for subcutaneous injection or intravenous infusion). For example, in some embodiments, a pharmaceutical compositions is provided in a liquid dosage form that is suitable for injection. In some embodiments, a pharmaceutical composition is provided as powders (e.g., lyophilized and/or sterilized), optionally under vacuum, which can be reconstituted with an aqueous diluent (e.g., water, buffer, salt solution, etc.) prior to injection. In some embodiments, a pharmaceutical composition is diluted and/or reconstituted in water, sodium chloride solution, sodium acetate solution, benzyl alcohol solution, phosphate buffered saline, etc. In some embodiments, a powder should be mixed gently with the aqueous diluent (e.g., not shaken).

In some embodiments, an anti-4-1BB antibody, antigen-binding fragment, and/or cell population of the present disclosure is formulated with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. A vehicle or lyophilized powder can contain additives that maintain isotonicity (e.g., sodium chloride, mannitol) and chemical stability (e.g., buffers and preservatives). In some embodiments, a formulation is sterilized by known or suitable techniques.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

In some embodiments, a pharmaceutical composition including an anti-4-1BB antibody, antigen-binding fragment, and/or cell population of the present disclosure can be included in a container for storage or administration, for example, an vial, a syringe (e.g., an IV syringe), or a bag (e.g., an IV bag). A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. The examples below describe, in part, dosing of an exemplary anti-human 4-1BB antibody to a rodent. Standard methods are known in the art of how to scale dosing in animal systems. See, for example, *J Basic Clin Pharm*. March 2016-May 2016; 7(2): 27-31, which is incorporated herein by reference in its entirety. By way of example, the composition may comprise between 0.1% and 100% (w/w) active ingredient.

In some embodiments, a composition comprises or delivers an anti-human 4-1BB antibody or antigen-binding fragment of the present disclosure at a dose of 0.01 mg/kg to 100 mg/kg. In some embodiments, a composition comprises or delivers an anti-human 4-1BB antibody or antigen-binding fragment at a dose in an amount within a range bounded by a lower limit and an upper limit, the upper limit being larger than the lower limit. In some embodiments, the lower limit may be about 0.01 mg/kg, 0.025 mg/kg, 0.05 mg/kg, 0.075 mg/kg, 0.1 mg/kg, 0.25 mg/kg, 0.5 mg/kg, 0.75 mg/kg, 1 mg/kg, 2 mg/kg, 3 mg/kg, 4 mg/kg, 5 mg/kg, 8 mg/kg, 10 mg/kg, 20 mg/kg, 25 mg/kg, 30 mg/kg, 40 mg/kg, 50 mg/kg, 50 mg/kg, 70 mg/kg, 80 mg/kg, or 90 mg/kg. In some embodiments, the upper limit may be about 0.025 mg/kg, 0.05 mg/kg, 0.075 mg/kg, 0.1 mg/kg, 0.25 mg/kg, 0.5 mg/kg, 0.75 mg/kg, 1 mg/kg, 2 mg/kg, 3 mg/kg, 4 mg/kg, 5 mg/kg, 8 mg/kg, 10 mg/kg, 20 mg/kg, 25 mg/kg, 30 mg/kg, 40 mg/kg, 50 mg/kg, 50 mg/kg, 70 mg/kg, 80 mg/kg, 90 mg/kg, or 100 mg/kg.

A pharmaceutical composition may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired.

Remington's The Science and Practice of Pharmacy, 21st Edition, A. R. Gennaro (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by the United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

In some embodiments, a provided pharmaceutical composition comprises one or more pharmaceutically acceptable excipients (e.g., preservative, inert diluent, dispersing agent, surface active agent and/or emulsifier, buffering agent, etc.). In some embodiments, a pharmaceutical composition comprises one or more preservatives. In some embodiments, pharmaceutical compositions comprise no preservative.

In some embodiments, a composition including an anti-human 4-1BB antibody or antigen-binding fragment of the present disclosure is stably formulated. In some embodiments, a stable formulation of an anti-human 4-1BB antibody or antigen-binding fragment of the present disclosure may comprise a phosphate buffer with saline or a chosen salt, as well as preserved solutions and formulations containing a preservative as well as multi-use preserved formulations suitable for pharmaceutical or veterinary use. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

In some embodiments, a pharmaceutical composition is provided in a form that can be refrigerated and/or frozen. In some embodiments, a pharmaceutical composition is provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody compositions for longer than the specified time results in antibody degradation.

Liquid dosage forms and/or reconstituted solutions may comprise particulate matter and/or discoloration prior to administration. In some embodiments, a solution should not be used if discolored or cloudy and/or if particulate matter remains after filtration.

General considerations in the formulation and/or manufacture of pharmaceutical agents may be found, for example, in Remington: The Science and Practice of Pharmacy 21st ed., Lippincott Williams & Wilkins, 2005.

Kits

The present disclosure further provides a pharmaceutical pack or kit comprising one or more containers filled with at least one anti-human 4-1BB antibody or antibody fragment as described herein. Kits may be used in any applicable method, including, for example, therapeutic methods, diagnostic methods, cell proliferation and/or isolation methods, etc. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In some embodiments, a kit may include one or more reagents for detection (e.g, detection of an anti-human 4-1BB antibody or antibody fragment). In some embodiments, a kit may include an anti-human 4-1BB antibody or antibody fragment in a detectable form (e.g., covalently associated with detectable moiety or entity).

In some embodiments, an anti-human 4-1BB antibody or antibody fragment as provided herein may be included in a kit used for treatment of subjects. In some embodiments, an anti-human 4-1BB antibody or antibody fragment as provided herein may be included in a kit used for proliferation and/or isolation of T cells (e.g., $CD8^+$ T cells).

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments. However, the following examples are merely provided to illustrate the present invention, but the scope of the present invention is not limited to the following examples.

EXAMPLES

The present disclosure provides, at least in part, humanized anti-human 4-1BB antibodies and fragments thereof with improved properties that contain one or more structural features that are not found in a reference humanized anti human 4-1BB antibody, 94G1. 94G1 was generated by humanization of the murine anti human 4-1BB antibody BBK-4 antibody. Antigen-recognizing sites (CDR regions) were determined using CDR loop assignment (IMGT: Lefranc, 1997) and a 3-D model (Swiss-Pdb Viewer (www.expasy.org)). A phage display library was prepared with diversity in a total of 10 sites including 4 sites on the amino acid sequence of the light chain and 6 sites of the heavy chain was constructed. After panning, approximately 14 humanized antibody clones out of 1,000 clones were selected (for a total of six humanized scFvs), and among the selected clones, 94G1, was obtained (Son et al. *J. Immunol. Methods* (2004) 286: 187-201). These humanized antibodies, including 94G1, had affinities for human 4-1BB antigen that were less than $1/10^{th}$ that of BBK-4, but were active in vitro. The present disclosure encompassed the recognition that structural variants of 94G1, may have improved properties. Generation and characterization of variant humanized anti-human 4-1BB antibodies and fragments thereof is described in further detail in the following examples.

Example 1—Preparation of Humanized Anti-Human 4-1BB Antibodies

This example describes the production of an exemplary anti-human 4-1BB antibodies with improved affinity over a reference 94G1 antibody. 94G1 was generated by humanizing a murine anti human 4-1BB antibody (BBK 4) as described in Son et al. *J. Immunol. Methods* (2004) 286: 187-201, which is herein incorporated by reference in its entirety. Also used herein is a H4-1BB antigen (Accession No: KCTC 0952BP) that is specifically isolated from activated T cells (e.g., activated T cell line), and has not been identified from unstimulated T cells. For example, a H4-1BB antigen can be isolated from T cells that have been matured by phorbol myristate acetate (PMA), ionomycin, Concanavalin A, or anti CD3i, This H4-1BB antigen has a size of 1.4 kb, and 60% homology with mouse 4-1BB (Garni-Wagner et al., Cellular Immunology (1996) 169: 91-98, which is herein incorporated by reference in its entirety). In this example, 94G1 was divided into a light chain and a heavy chain vectors, each of optimized to generate improved humanized antibodies.

The present disclosure encompasses a recognition that a suitable method for generating improved humanized anti-human 4-1BB antibodies or fragments thereof is through single, stepwise amino acid substitutions and/or combinations thereof. The present disclosure provides various structural variants of humanized anti-human 4-1BB antibodies and fragments thereof with one or more structural features (e.g., amino acid substitutions) that are not found in a 94G1 antibody. The present disclosure further encompasses a recognition that structural features can be combined for stepwise improvements in one or more antibody properties (e.g., increased antigen affinity).

First, a humanized anti-human 4-1BB antibody with increased affinity relative to 94G1 reference antibody was obtained by changing a CDR region of a light chain, rather than a heavy chain. This light chain structural variant was fixed, and combined with humanized anti-human 4-1BB antibody heavy chains structural variants with, e.g., mutations in the CDR region of 94G1. Further structural features were integrated to generate humanized anti-human 4-1BB antibodies with high affinity and/or other improved characteristics.

1.1 Construction of Vectors

Vectors with a 94G1 light chain and 94G1 heavy chain, respectively, were constructed by changing pComb3H-HA to be expressed in a Fab type to improve a heavy chain and a light chain of a humanized antibody in *E. coli* (*J. Immunol Methods* (2008) 329(1-2):176-83; Virology (2004) 318: 598). Specifically, a 94G1 light chain was inserted into a vector designed by changing an AP2 tag (SEQ ID NO: 42—NANNPDWDFNP) with a flag tag (SEQ ID NO: 43—DYKDDDDK), the flag tag is designed to be located downstream thereof, and has a human heavy chain sequence (Accession No. AB019438) obtained from known data of the NCBI GenBank was placed as a constant domain in a heavy chain position. In addition, after a 94G1 light chain sequence was cloned into the vector, it was transferred to *E. coli* (e.g., TG1) (F' [traD36 proAB+lacIqlacZΔM15]supE thi-1 Δ(lac-proAB) Δ(mcrB-hsdSM)5, (rK-mK-) by transformation, followed by selection of a transformed vector called pCOM-Fab-94G1-L, which was used as a backbone to induce affinity maturation of the light chain (Table 1). The above-described method was similarly carried out for the 94G1 heavy chain, and a selected vector was called pCOM-Fab-94G1-H. An improved light chain, 94/w, was designed as the light chain of pCOM-Fab-94G1, which served as backbone for production of heavy chain variants with improved affinity.

TABLE 1

94G1 and 94/w LCDR amino acid sequences

| SEQ ID NO. | Amino acid sequence | CDR |
|---|---|---|
| SEQ ID NO: 1 | QTISDY | LCDR 1 |
| SEQ ID NO: 2 | YAS | LCDR 2 |
| SEQ ID NO: 3 | QDGHSFPPT | LCDR 3 |
| SEQ ID NO: 4 | QDGHSWPPT | LCDR 3.6 variant 94/w |

1.2 Affinity Maturation of Humanized Anti-Human 4-1BB Antibody Light Chain

Described herein is the development a humanized anti-human 4-1BB antibody with a light chain variant that has improved binding affinity. An antibody with a high affinity was obtained by changing LCDR3 (SEQ ID NO: 3) of a 94G1 light chain in the context of the pCOM-Fab-94G1-L vector described above as follows. Various DNA sequences encoding a light chain were amplified by PCR using primers [using NNS (N: A, T, C, G; S: C, G)] designed to insert 19 different amino acids into each amino acid position of the 9 amino acids SEQ ID NO: 3, constituting the LCDR3 part of the 94G1 light chain. Amplified products were ligated to a light chain position of the vector and then transformed into *E. coli* TG1. All clones with light chain structure variants of LCDR3 were substituted in different forms and collected to prepare nine position mixes. To assess whether each amino acid position was substituted with a different amino acid, two clones changed in respective positions were randomly chosen and analyzed by sequencing using an ABI-3730xl sequencer, which showed that the amino acid residues at respective positions were substituted at various forms.

To see whether 94G1 Fab variants with mutations at different LCDR3 positions had increased antibody affinity, each position mix was expressed by adding IPTG (to a final concentration of 1 mM) to *E. coli* TG1, and then Fab antibody present in a supernatant was subjected to ELISA. Specifically, each position mix was cultured with shaking in a 2YT medium in a 37° C. incubator until the culture had an absorbance at 600 nm of 0.8 or more, then overnight cultured at 30° C. with IPTG (e.g., at a final concentration of 1 mM). ELISA was performed the following day on a supernatant obtained by centrifugation at 12,000 rpm for 10 minutes at 4° C. Binding affinities were determined for the various 94G1 LCDR3 variant Fabs by dividing the binding activities of each clones with respect to 4-1BB Fab by the expression levels for the respective mutant clone. A 94G1 LCDR3 variant with a mutation position 6 of LCDR3 (LCDR3.6) showed the highest binding affinity.

Subsequently, to determine how various mutations of 94G1 at the LCDR3.6 position impacted antibody affinity, 25 monoclonal antibodies were isolated from pCOM-Fab94G1-LCDR3.6 position mix and expressed by adding IPTG (e.g., at a final concentration of 1 mM) to *E. coli* (e.g., TG1), cultured, and ELISA was performed on a Fab antibody present in a supernatant. Binding affinities were determined for the various 94G1 LCDR3.6 clones by dividing the 4-1BB Fab binding activities of each clones by the expression levels for each.

A 94G1 LCDR3.6 variant with phenylalanine at the LCDR3.6 position substituted with tryptophan exhibited the highest binding affinity. A Fab antibody prepared by substituting the constant heavy chain of pCOM-Fab94G1-L with the heavy chain of the backbone 94G1 on the improved 94G1 light chain was called 94/w. Thus, a 94/w variant includes an improved 94G1 light chain in which the 6$^{th}$ amino acid of LCDR3 is substituted with tryptophan (W) (QDGHSWPPT—SEQ ID NO: 4) and a 94G1 heavy chain. IPTG-induced expression in *E. coli* and ELISA of a 94/w Fab was used to determine binding affinity as described above. Using this method, it was determined that a 94/w Fab antibody has a binding activity 3.5 times higher than that of 94G1 (Fab antibody) (data not shown).

1.3 Affinity Maturation of Humanized Anti-Human 4-1BB Antibody Heavy Chain CDRs Described herein is the development humanized anti-human 4-1BB antibodies with heavy chain structural variants that have improved binding affinity. To achieve further improved anti-human 4-1BB antibodies, a 94/w light chain as described above was used and the 94G1 heavy chain was affinity matured. Provided in Table 2 below are the HCDR amino acid sequences for a reference 94G1 antibody heavy chain.

TABLE 2

94G1 and 94K HCDR amino acid sequences

| SEQ ID NO. | Amino acid sequence | CDR |
|---|---|---|
| SEQ ID NO: 5 | GYTFSSYW | HCDR 1 |
| SEQ ID NO: 6 | INPGNGHT | HCDR 2 |
| SEQ ID NO: 7 | ARSFTTARAFAY | HCDR 3 |
| SEQ ID NO: 8 | ARSFKTARAFAY | HCDR 3.5 variant 94K |

Improvement of a heavy chain using 94/w as a starting sequence was performed by similar methods as described for the 94G1 light chain above. Particularly, to improve a 94G1 heavy chain, amino acid residues were substituted with various amino acids at respective amino acid positions of HDR2 and/or HCDR3. In the case of the third CDR of the heavy chain (HCDR3, SEQ ID NO: 7), clones were produced with random substitution amino acid residues of 94/w HCDR3 by different amino acids were collected to prepare 12 position mixes. A mutant clone that increases the length of HCDR3 was also prepared. When the $5^{th}$ amino acid residue of HCDR3 was substituted with a different amino acid, an affinity increase was observed. Subsequently, to determine how various mutations at the HCDR3.5 position impacted affinity of the 94/w antibody, 19 monoclonal antibodies were isolated from a position mix in which the HCDR3.5 position of the 94/w antibody was randomly substituted. HCDR3.5 variant Fabs were expressed in E. coli by adding IPTG (e.g., to a concentration of 1 mM) and ELISA was performed using a Fab antibody present in a supernatant. Sequencing identified that when threonine was substituted with lysine at HCDR3.5 ($5^{th}$ position) position (SEQ ID NO: 8—ARSFKTARAFAY), the highest affinity was shown, and the resulting product was called 94K/w.

In the case of the second CDR of the heavy chain (HCDR2), a position mix was prepared by random substitution of each of 9 amino acids of a 94G1 HCDR2 (SEQ ID NO: 6) for ELISA. The ELISA results showed that when amino acid residues at $2^{nd}$, $5^{th}$ and $6^{th}$ positions were changed, the affinity increased. From each of the 94/w HCDR2.2, HCDR2.5 and HCDR2.6 position mixes, 22, 19, and 36 monoclonal antibodies were isolated, respectively, and the binding activity of each clone with respect to 4-1BB was analyzed depending on an Fab expression level. In the case of HCDR2.5, an ELISA value was relatively higher than those when asparagine was substituted with valine (V), glycine (G), or proline (P). In addition, according to sequencing data for antibody heavy chains, there was a risk of deamination at the $5^{th}$ amino acid, asparagine (N), of HCDR2 (SEQ ID NO: 6), and variant HCDR2 sequences were also prepared with substitutions at this residue with each of glutamine (Q), glutamic acid (E), and serine (S).

DNAs of 94G1 structural variants with mutations in HCDR3 and/or HDR2 of the heavy chain prepared as described above, were amplified by PCR using a three-base sequence NNS, ligated to the heavy chain position of a vector having a constant domain of the 94/w light chain, and then transformed into E. coli TG1 by the method used in improvement of the light chain as described above.

1.4 Optimization of Humanized Anti-Human 4-1BB Antibody Heavy Chain Framework Regions Heavy chain variants were also produced with optimized framework sequences. For example, heavy chain framework 1 (FR1) regions were produced where the heavy chain FR1 (SEQ ID NO: 16) was modified so that the $5^{th}$ amino acid, glutamine (Q), was substituted with valine (V). Exemplary FR1 regions are provided in Table 3 below.

TABLE 3

| 94G1 heavy chain FR1 and variations thereof | |
|---|---|
| SEQ ID NO. | Amino acid sequence |
| SEQ ID NO: 16 | QVQLQQSGAEVKKPGASVKLSCKAS 94G1 FR1 |
| SEQ ID NO: 17 | QVQLVQSGAEVKKPGASVKLSCKAS FR1 Gln 5 Val |

Also, framework 3 (FR3) regions were produced where the heavy chain FR3 (SEQ ID NO: 18) was modified as such: the $10^{th}$ amino acid, alanine (A), and/or the $33^{rd}$ amino acid, serine (S), which were murine sequences, were substituted with valine (V) and threonine (T), respectively. Exemplary FR3 regions are provided in Table 4 below.

TABLE 4

| 94G1 heavy chain FR3 and variations thereof | |
|---|---|
| SEQ ID NO. | Amino acid sequence |
| SEQ ID NO: 18 | NYNEKFKSRATMTRDTSTSTA 94G1 FR3 YMELSSLRSEDSAVYYC |
| SEQ ID NO: 19 | NYNEKFKSRVTMTRDTSTSTA FR3 Ala 10 Val YMELSSLRSEDSAVYYC |
| SEQ ID NO: 20 | NYNEKFKSRVTMTRDTSTSTA FR3 Ala 10 Val; YMELSSLRSEDTAVYYC  FR3 Ser 33 Thr |

1.5 Preparation of Humanized Anti-Human 4-1BB Variable Regions and Full-Length Antibodies Anti-human 4-1BB antibody variable regions were produced that include various combinations of the above described heavy chain and light chain CDRs and framework regions. For example, a Fab-type 94KVT/w antibody was produced with the $5^{th}$ amino acid, threonine, at CDR3 of a heavy chain was substituted with lysine (K), and the $10^{th}$ amino acid of heavy chain FR3, alanine, and the $33^{rd}$ amino acid of heavy chain FR3, serine, were substituted with valine (V) and threonine (T), respectively to produce heavy chain and light chain variable region sequence that are or include SEQ ID NO: 30 and SEQ ID NO: 34, respectively. In addition, 94KVT heavy chain variants were produced where the $5^{th}$ amino acid of HCDR2 (SEQ ID NO: 6), asparagine (N), was substituted with glutamine (Q), glutamic acid (E) or serine (S). Exemplary heavy chain and light chain variable domain sequences are provided in Table 5 below (CDR sequences underlined).

TABLE 5

Exemplary humanized anti-human 4-1BB antibody variable domains

| Antibody | Light chain variable domain | Heavy chain variable domain |
|---|---|---|
| 94G1 | DIVMTQSPAFLSVTPGEKVTIT<br>CRAS<u>QTISDYLH</u>WYQQKPDQ<br>APKLLIK<u>YASQSIS</u>GIPSRFSGS<br>GSGTDFTFTISSLEAEDAATYY<br>C<u>QDGHSFPPT</u>FGQGTKLEIK<br>(SEQ ID NO: 9) | QVQLQQSGAEVKKPGASVKLS<br>CKAS<u>GYTFSSYWMH</u>WVRQAP<br>GQGLEWIG<u>EINPGNGHT</u>NYNEK<br>FKSRATMTRDTSTSTAYMELSS<br>LRSEDSAVYYC<u>ARSFTTARAFA</u><br><u>Y</u>WGQGTLVTVSS<br>(SEQ ID NO: 11) |

TABLE 5-continued

Exemplary humanized anti-human 4-1BB antibody variable domains

| Antibody | Light chain variable domain | Heavy chain variable domain |
| --- | --- | --- |
| 94w | DIVMTQSPAFLSVTPGEKVTIT<br>CRAS<u>QTISD</u>YLHWYQQKPDQ<br>APKLLIK<u>YAS</u>QSISGIPSRFSGS<br>GSGTDFTFTISSLEAEDAATYY<br>C<u>QDGHSWPPT</u>FGQGTKLEIK<br>(SEQ ID NO: 10) | QVQLQQSGAEVKKPGASVKLS<br>CKAS<u>GYTFSSYWMH</u>WVRQAP<br>GQGLEWIG<u>EINPGNGHT</u>NYNEK<br>FKSRATMTRDTSTSTAYMELSS<br>LRSEDSAVYYC<u>ARSFTTARAFA</u><br><u>Y</u>WGQGTLVTVSS<br>(SEQ ID NO: 11) |
| 94K/w | DIVMTQSPAFLSVTPGEKVTIT<br>CRAS<u>QTISD</u>YLHWYQQKPDQ<br>APKLLIK<u>YAS</u>QSISGIPSRFSGS<br>GSGTDFTFTISSLEAEDAATYY<br>C<u>QDGHSWPPT</u>FGQGTKLEIK<br>(SEQ ID NO: 10) | QVQLQQSGAEVKKPGASVKLS<br>CKAS<u>GYTFSSYWMH</u>WVRQAP<br>GQGLEWIG<u>EINPGNGHT</u>NYNEK<br>FKSRATMTRDTSTSTAYMELSS<br>LRSEDSAVYYC<u>ARSFKTARAFA</u><br><u>Y</u>WGQGTLVTVSS<br>(SEQ ID NO: 12) |
| 94KV/w | DIVMTQSPAFLSVTPGEKVTIT<br>CRAS<u>QTISD</u>YLHWYQQKPDQ<br>APKLLIK<u>YAS</u>QSISGIPSRFSGS<br>GSGTDFTFTISSLEAEDAATYY<br>C<u>QDGHSWPPT</u>FGQGTKLEIK<br>(SEQ ID NO: 10) | QVQLVQSGAEVKKPGASVKLS<br>CKAS<u>GYTFSSYWMH</u>WVRQAP<br>GQGLEWIG<u>EINPGNGHT</u>NYNEK<br>FKSRVTMTRDTSTSTAYMELSS<br>LRSEDSAVYYC<u>ARSFKTARAFA</u><br><u>Y</u>WGQGTLVTVSS<br>(SEQ ID NO: 13) |
| 94KVT/w,<br>EU101 | DIVMTQSPAFLSVTPGEKVTIT<br>CRAS<u>QTISD</u>YLHWYQQKPDQ<br>APKLLIK<u>YAS</u>QSISGIPSRFSGS<br>GSGTDFTFTISSLEAEDAATYY<br>C<u>QDGHSWPPT</u>FGQGTKLEIK<br>(SEQ ID NO: 10) | QVQLVQSGAEVKKPGASVKLS<br>CKAS<u>GYTFSSYWMH</u>WVRQAP<br>GQGLEWIG<u>EINPGNGHT</u>NYNEK<br>FKSRVTMTRDTSTSTAYMELSS<br>LRSEDTAVYYC<u>ARSFKTARAFA</u><br><u>Y</u>WGQGTLVTVSS<br>(SEQ ID NO: 14) |

For conversion to a full-length anti-human 4-1BB antibodies (whole Ig type), an Fc domain was connected to the respective Fab. For example, a 94K/w Fab composed of a heavy chain in which threonine is substituted with lysine at HCDR3.5 and a light chain with 94/w variant in which the 6th amino acid of LCDR3 is substituted with tryptophan (W), and respective regions extended from CH2 and CH3 domains and a sequence of human IgG1 were amplified by PCR to overlap and subjected to splice PCR to produce full IgG DNA, and then the resulting DNA was cloned in a mammalian expression vector. Full length antibodies for other humanized anti-human 4-1BB antibodies described herein were produced in a similar manner. Exemplary immunoglobulin constant region sequences are provided in Table 6 below.

TABLE 6

Exemplary immunoglobulin constant domains

| SEQ ID NO. | Amino acid sequence | Description |
| --- | --- | --- |
| SEQ ID NO: 21 | RTVAAPSVFIFPPSDEQLKSGTASVVCLLNNFYPRE<br>AKVQWKVDNALQSGNSQESVTEQDSK<br>DSTYSLSSTLTLSKADYEKHKVYACEVTHQ<br>GLSSPVTKSFNRGEC | κ constant<br>domain |
| SEQ ID NO: 22 | ASTKGPSVFPLAPSSKSTSGGTAALGCLVKDYFPEP<br>VTVSWNSGALTSGVHTFPAVLQSSGLYS<br>LSSVVTVPSSSLGTQTYICNVNHKPSNTKVDK<br>KVEPKSCDKTHTCPPCPAPELLGGPSVFLFPP<br>KPKDTLMISRTPEVTCVVVDVSHEDPEVKFN<br>WYVDGVEVHNAKTKPREEQYNSTYRVVSVL<br>TVLHQDWLNGKEYKCKVSNKALPAPIEKTIS<br>KAKGQPREPQVYTLPPSRDELTKNQVSLTCL<br>VKGFYPSDIAVEWESNGQPENNYKTTPPVLD<br>SDGSFFLYSKLTVDKSRWQQGNVFSCSVMHE<br>ALHNHYTQKSLSLSPGK | IgG1 |
| SEQ ID NO: 23 | ASTKGPSVFPLAPSSKSTSGGTAALGCLVKDY<br>FPEPVTVSWNSGALTSGVHTFPAVLQSSGLYS<br>LSSVVTVPSSSLGTQTYICNVNHKPSNTKVDK<br>KVEPKSCDKTHTCPPCPAPEAAGGPSVFLFPP<br>KPKDTLMISRTPEVTCVVVDVSHEDPEVKFN<br>WYVDGVEVHNAKTKPREEQYNSTYRVVSVL<br>TVLHQDWLNGKEYKCAVSNKALPAPIEKTIS<br>KAKGQPREPQVYTLPPSRDELTKNQVSLTCL | IgG1 variant<br>(L234; L235;<br>K322) |

TABLE 6-continued

Exemplary immunoglobulin constant domains

| SEQ ID NO. | Amino acid sequence | Description |
|---|---|---|
| | VKGFYPSDIAVEWESNGQPENNYKTTPPVLD<br>SDGSFFLYSKLTVDKSRWQQGNVFSCSVMHE<br>ALHNHYTQKSLSLSPGK | |

As used herein a full length 94KVT/w antibody includes an IgG1 sequence, such as that of SEQ ID NO: 22. Additionally, a full length antibody, referred to herein as EU101, was produced that includes 94KVT/w variable domains describe above (SEQ ID NOs: 10 and 14, for light chain and heavy chain variable domains, respectively), with a variant IgG1 constant domain that includes 3 mutations: L234, L235, and K322 (SEQ ID NO: 23). Thus, example provides a number of exemplary humanized anti-human 4-1BB antibodies and antibody fragments that have been engineered to potentially enhance antigen binding affinity. These exemplary antibodies and fragments are characterized in the following examples.

Example 2—Characterization of Binding of Humanized Anti-Human 4-1BB Antibodies

2.1 Determining Binding Epitope of Anti-Human 4-1BB Antibodies

The present disclosure encompasses a recognition that humanized anti-human 4-1BB antibodies provided herein may be useful for 4-1BB co-stimulation. Therapeutic applications of antibodies of the present disclosure may include promoting anti-cancer immunity and/or anti-viral immunity. However, for clinical applications, it is important to identify which part of human 4-1BB is recognized by and/or reacts with an anti-humanized 4-1BB antibody (i.e., a binding epitope). 4-1BB antibodies that recognize different epitopes of 4-1BB molecule have identified, and these antibodies can have been shown to have different clinical effects. (See, e.g., Kwon et al. Eur. J. Immunogenetics (2002) 29: 449-452, herein incorporated by reference in its entirety). Epitope mapping encompasses methods for identifying a molecular determinant of antibody-antigen recognition. This example describes epitope mapping of an exemplary anti-human 4-1BB antibody as engineered in Example 1 above. Specifically, this example assesses the binding epitope of a humanized anti-human 4-1BB antibody with 94KVT/w variable domains, EU101.

A human 4-1BB antigen for investigating an epitope of the humanized 4-1BB antibody is derived from a cDNA library manufactured from human peripheral blood lymphocytes that was generated by at least some of the inventors of the present application (See, e.g., Kwon et al. Cellular Immunology (1996) 169: 91-98; Immunol. Lett. (1995) 45: 67-73; and Korean Patent No. 10-0500286, each of which is incorporated herein by reference). cDNA encoding an extracellular domain (ECD) of the obtained human homologue of 4-1BB cDNA (hereinafter, referred to as H4-1BB) was selected, fused with GST, and then inserted into a vector (pGEX-6T) to express. A cell line producing a GST-4-1BB fusion polypeptide as used herein, was deposited as part of the disclosure for Korean Patent No. 10-0500286, Accession No: KCTC 0952BP. A full length sequence of human 4-1BB is provided as SEQ ID NO: 44, below. The extracellular domain of human 4-1BB corresponds to amino acids 1 to 167 of the full length H4-1BB sequence.

```
Full length human 4-1BB sequence
                                    SEQ ID NO: 44
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL
```

To determine an epitope of 4-1BB recognized by humanized anti-human 4-1BB antibodies of the present disclosure, constructs were generated with fragments of a 4-1BB extracellular domain of various sizes (e.g., R1, R2, R3), fused to GST, and replicated. A schematic of GST-4-1BB polypeptides as used in the present example is provided in FIG. 1A. and exemplary primer sequences used herein for generating different 4-1BB extracellular domain constructs are provided in Table 7 below. Individual recombinant GST-H-4-1BB constructs were cultured with 1 mM IPTG and produced in E. coli BL21DX5a cells, and the fusion polypeptides were purified using a glutathione-agarose column.

TABLE 7

Exemplary primers used to generate human 4-1BB extracellular domain fragments useful for epitope mapping

| | Forward | Reverse |
|---|---|---|
| R1 | 5'-<br>GGATCCACAAGATCATTGCA<br>G-3' (SEQ ID NO. 24) | 5'-<br>TTGAGCTCGAGCCTGGTCCT<br>GAAAACA-3'<br>(SEQ ID NO. 25) |
| R2 | 5'-<br>CGCGTGGATCCAAGGAGTGTT<br>CCTCCA-3'<br>(SEQ ID NO. 26) | 5'-<br>TTGAGCTCGAGACGTTTCTG<br>ATCGTTA-3'<br>(SEQ ID NO. 27) |
| R3 | 5'-<br>CGCGTGGATCCGGCATCTGTC<br>GACCCT-3'<br>(SEQ ID NO. 28) | 5'-<br>TTGAGCTCGAGGATCTGCGG<br>AGAGTGT-3'<br>(SEQ ID NO. 29) |
| R1.1 | 5'-<br>GGATCCACAAGATCATTGCA<br>G-3' (SEQ ID NO. 30) | 5'-<br>CTCGAGGCATATGTCACAG<br>GT-3' (SEQ ID NO. 31) |
| R1.2 | 5'-<br>GGATCCACAAGATCATTGCA<br>G-3' (SEQ ID NO. 32) | 5'-<br>CTCGAGGCTGGAGAAACT<br>AT-3' (SEQ ID NO. 33) |
| R1.3 | 5'-<br>GGATCCTGCCCAGCTGGTA<br>C-3' (SEQ ID NO. 34) | 5'-<br>TTGAGCTCGAGCCTGGTCCTGAAA<br>ACA-3' (SEQ ID NO. 35) |

TABLE 7-continued

Exemplary primers used to generate human 4-1BB extracellular domain fragments useful for epitope mapping

| | Forward | Reverse |
|---|---|---|
| R1.4 | 5'-GGATCCAGGAATCAGATTTGC-3' (SEQ ID NO. 36) | 5'-TTGAGCTCGAGCCTGGTCCTGAAACA-3' (SEQ ID NO. 37) |
| R1.5 | 5'-GGATCCACAAGATCATTGCAG-3' (SEQ ID NO. 38) | 5'-CTCGAGGCAAATCTGATTCCT-3' (SEQ ID NO. 39) |
| R1.6 | 5'-GGATCCACAAGATCATTGCAG-3' (SEQ ID NO. 40) | 5'-CTCGAGTGGAGGACAGGGACT-3' (SEQ ID NO. 41) |

Purified protein samples were obtained from transformed bacterial cells by a lysis buffer (e.g., 10 mM Tris-HCl—pH 7.4, 50 mM NaCl, 5 mM EDTA, 30 mM NaF, 0.1 mM Na3VO4, 1% Triton X-100, 0.5% Nonidet P-40, 1 mM PMSF, and protease inhibitor mixture). Approximately 20 µg of each fusion polypeptide sample was diluted in a 4×SDS sample buffer, subjected to electrophoresis on SDS-PAGE gels, and then transferred to nitrocellulose membranes (Millipore, Bedford, Mass.). On the cellulose membranes, anti-human 4-1BB mAb was reacted with anti-mouse IgG horseradish peroxide (HRP). Binding antibodies were recognized by enhanced chemiluminescence (ECL) (Amersham Pharmacia Biotech, Little Chalfont, UK).

As described above and shown in FIG. 1B, when each of three non-overlapping H4-1BB ECD fragment-GST fusion polypeptides, R1, R2, and R3, were treated with GST-binding, respectively. It was determined that an exemplary humanized anti-4-1BB antibody encompassed by the present disclosure (EU101) binds to an N-terminal fragment construct (R1) fusion construct of approximately 32 kDa (amino acids 1 to 55 of 4-1BB) by western blotting. Moreover, this binding was specific, as no binding was observed with either of the R2 or R3 fusion constructs. See FIG. 1B.

Figure 1B:
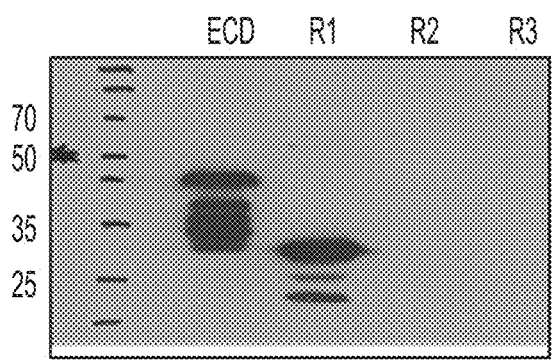
FIG. 1B depicts a western blot showing binding of an exemplary humanized anti-4-1BB antibody to 4-1BB ECD fusion constructs as described in FIG. 1A. As shown, an exemplary humanized anti-4-1BB antibody binds to a full length 4-1BB ECD fusion polypeptide and to the R1 fusion polypeptide, but not to the R2 or R3 fusion polypeptides. Molecular size markers are indicated in kDa on the left.
Figure 2A:
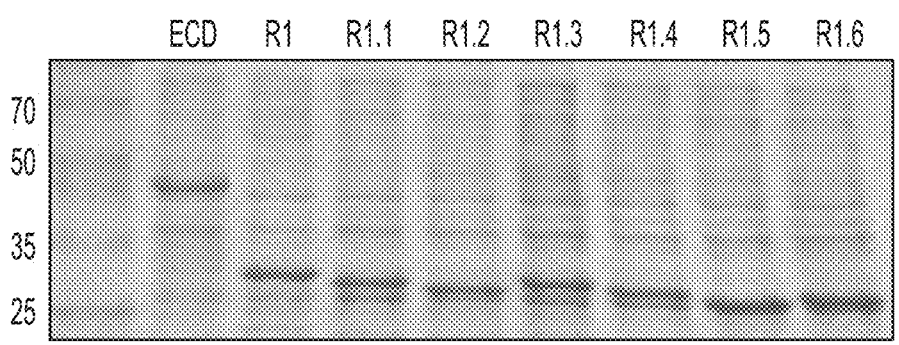
FIG. 2A depicts an SDS-PAGE gel of whole cell extracts from cells expressing 4-1BB ECD fusion constructs. Fusion constructs as described above in FIG. 2A were expressed in E. coli BL21 cells induced with 1 mM IPTG, and whole cell extracts resolved by 12% SDS-PAGE. As shown, all fusion constructs (ECD, R1, R1.1, R1.2, R1.3, R1.4, R1.5, and R1.6) have robust protein expression.

Furthermore, to determine the minimal binding site of the humanized anti-4-1BB antibody, an R1 extracellular domain fragment was further divided into 6 smaller fragments: R1.1 (amino acids 1 to 45 of 4-1BB), R1.2 (amino acids 1 to 35 of 4-1BB), R1.3 (amino acids 11 to 55 of 4-1BB), R1.4 (amino acids 21 to 55 of 4-1BB), R1.5 (amino acids 1 to 25 of 4-1BB), and R1.6 (amino acids 1 to 30 of 4-1BB) polypeptide fragments, as depicted in FIG. 1A, and fused to GST (Glutathione S-Transferase, 27 kDa). Exemplary primer pairs used for the generation of these constructs are provided in Table 7 above. Fusion polypeptide constructs were produced in E. coli BL21 cells with IPTG induction (e.g., 1 mM IPTG) and bacterial whole cell extract was resolved by 12% SDS-PAGE. As shown in FIG. 2A, SDS-PAGE confirmed that individual 4-1BB fusion polypeptides are well expressed.

Figure 2B:
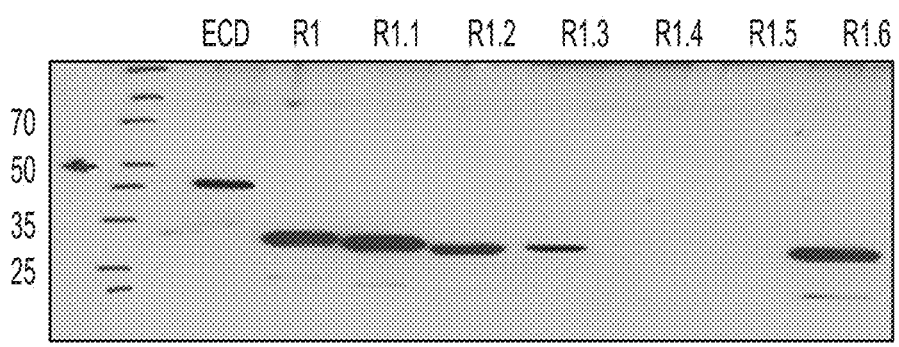
FIG. 2B depicts a western blot showing binding of an exemplary humanized anti-4-1BB antibody to full length 4-1BB ECD fusion polypeptide, and R1.1, R1.2, R1.3, and R1.6 fusion polypeptides, but not to the R1.4 or R1.5 fusion polypeptides. Immunoblots were performed with an exemplary anti-human 4-1BB antibody. Molecular size markers are indicated in kDa on the left.

SDS-PAGE was transferred to a nitrocellulose membrane and immunoblotting was performed using an exemplary anti-human 4-1BB antibody, EU101. As shown in FIG. 2B, it was confirmed that a sequence of amino acids 10 to 30 of the extracellular domain of H4-1BB is significant for binding an exemplary humanized anti-4-1BB antibody. This analysis indicates that an exemplary anti-human 4-1BB antibody of the present disclosure (EU101) binds to an epitope of human 4-1BB whose sequence is or includes CPAGTFCDNNRNQICSPCPP (SEQ ID NO: 15). It was also confirmed that a sequence including amino acids 35 to 50 of the 4-1BB extracellular domain is not significant for binding an exemplary humanized antibody described herein (FIG. 2B).

2.2 Assessing Binding Affinity of Exemplary Humanized Anti-Human 4-1BB Antibodies to 4-1BB Antigen Binding Ability of Exemplary Anti-Human 4-1BB Antibodies To examine the binding ability of exemplary humanized anti-human 4-1BB antibodies described in Example 1 to a human 4-1BB antigen (H4-1BB), ELISA was performed. E. coli-expressed recombinant human 4-1BB was used for antigen.

Figure 3:
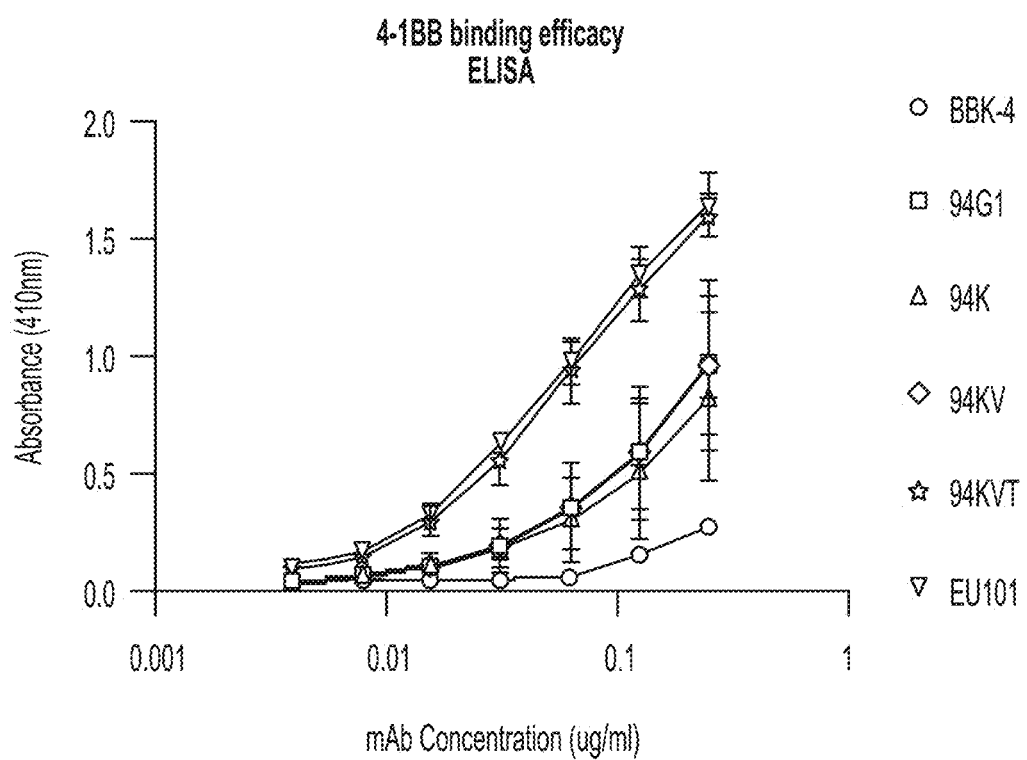
FIG. 3 depicts binding affinity of anti-4-1BB monoclonal antibodies for recombinant human 4-1BB antigen, as measured by ELISA. $OD_{450\ nm}$ values are represented on the y-axis, and increasing concentrations of anti-4-1BB antibodies (in µg/ml) along the x-axis. BBK-4 (circles) is a murine anti-human 4-1BB antibody, 94G1 (squares), 94K (upward pointing triangles), 94 KV (diamonds), 94KVT (stars) and EU101 (downward pointing triangles) are exemplary humanized variant anti-4-1BB antibodies.

A murine BBK-4 antibody, a reference 94G1 humanized antibody, and exemplary engineered antibodies 94K, 94 KV, 94KVT and EU101 as described in Example 1 were each treated on 96 well plates coated with histidine-tagged 4-1BB extracellular domain recombinant protein (H4-1BB). Exemplary ELISA affinity analysis employed a total volume of 100 µl at a concentration of 1.0 µg/ml, and the reaction was allowed to proceed at room temperature for 1 hour. Horseradish peroxidase (HRP)-labeled anti-human IgG and anti-mIgG-HRP, as appropriate, recognizing an antibody was treated thereto, and allow to react at room temperature for 40 minutes. After washing, treatment with an ABTS solution (Sigma-Aldrich), which is a substrate for a coloring reaction, and the reaction to allow to proceed at room temperature for 30 minutes, and an absorbance at 450 nm in the coloring reaction was detected using an ELISA reader to analyze a binding activity of the antibodies. Results are shown in FIG. 3. As shown in FIG. 3, as antibody concentration increases, binding between each antibody and 4-1BB antigen (H4-1BB) is improved. This data confirms that antibodies encompassed by the present disclosure specifically bind to 4-1BB.

Binding of Exemplary Anti-Human 4-1BB Antibodies to Cell-Expressed Antigen

Figure 4:
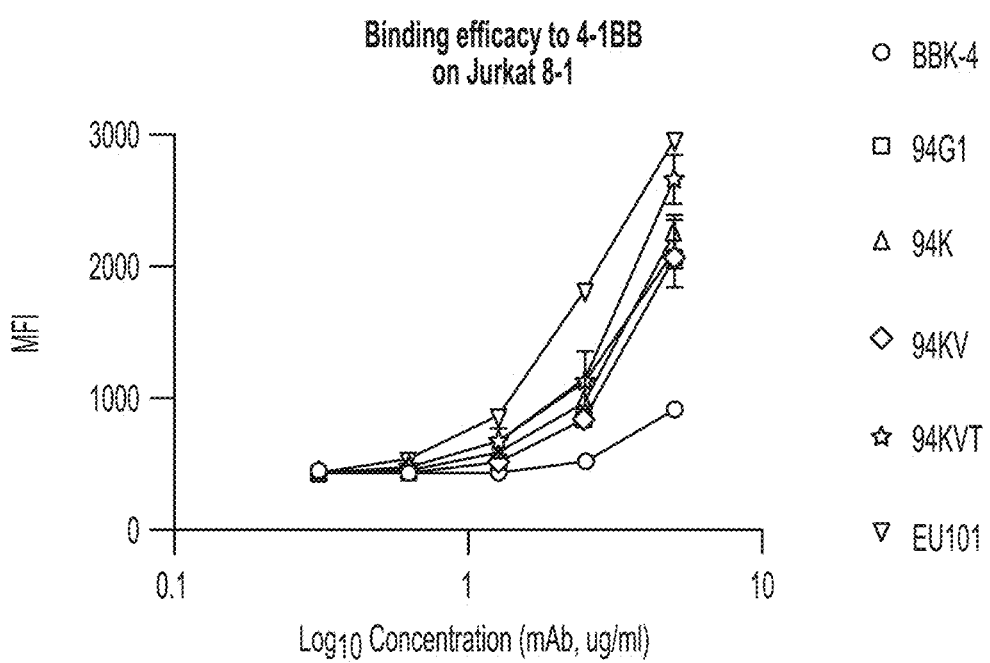
FIG. 4 depicts binding of anti-4-1BB monoclonal antibodies to 4-1BB expressing Jurkat T cells (Jurkat 8-1). Mean Fluorescence Intensity (MFI) values are represented on the y-axis and Log 10 concentration of antibody (in g/ml) along the x-axis. BBK-4 (circles) is a murine anti-human 4-1BB antibody, 94G1 (squares), 94K (upward pointing triangles), 94 KV (diamonds), 94KVT (stars) and EU101 (downward pointing triangles) are exemplary humanized variant anti-4-1BB antibodies.

The ability of exemplary humanized anti-human 4-1BB antibodies to bind a human 4-1BB antigen (H4-1BB) in a cellular context was assessed. Jurkat 8-1 cells were genetically engineered for overexpressing 4-1BB. Exemplary engineered antibodies 94K, 94 KV, 94KVT and EU101 as described in Example 1, along with that of a murine BBK-4 antibody, and a reference 94G1 humanized antibody were each assessed for binding to Jurkat 8-1 cells using an anti-mIgG-HRP or anti-hIgG-HRP secondary antibody, as appropriate, and analyzed by FACS. As shown in FIG. 4, each of the antibodies were able to effectively bind 4-1BB expressed by Jurkat 8-1 cells and the affinity of 94KVT and EU101 was higher than BBK-4 and 94G1. In vitro binding affinity of exemplary anti-human 4-1BB antibodies to antigen In vitro binding affinity of exemplary engineered antibody EU101 as described in Example 1, along with that of a reference 94G1 humanized antibody were each determined by Biacore analysis. Anti-human IgG was immobilized on a CM5 chip, and coupled to the Fab antibodies prepared above by flowing over the chip, and ultimately reacted with a human 4-1BB antigen (H4-1BB) to measure the binding activity between the antibody and the antigen (Biacore3000, sensor chip CM5). Affinity measurement results are shown in FIG. 5. Ka (1/Ms) and Kd (1/s) values represent how fast an antibody associates with and dissociates from an antigen, respectively. A dissociation constant ($K_D$) is obtain by dividing Kd by Ka ($Kd/Ka=K_D$).

As a dissociation constant decreases, it can be interpreted that dissociation occurs at a lower concentration and that affinity is increasing. As shown in FIG. 5, the exemplary engineered anti-human 4-1BB antibody had improved binding affinity relative to a reference 94G1.

Exemplary Anti-Human 4-1BB Antibodies Recognize 4-1BB Expressed by Activated CD8+ T Cells CD8+ T cells were isolated from human PBMCs and activated with 1 μg/ml anti-CD3 antibody—for 2 day. The ability of exemplary humanized anti-human 4-1BB antibodies (94K, 94 KV, 94KVT and EU101) described in Example 1 to detect a 4-1BB on the surface of activated CD8+ T cells was assessed relative to an exemplary commercially available anti-4-1BB antibody (4-1BB-PE). Also shown is detection with a BBK-4 a murine anti-human 4-1BB antibody and a 94G1 reference humanized antibody. Treatment with 4-1BB antibodies was at a concentration of 25 ng/ml.

Figure 6:
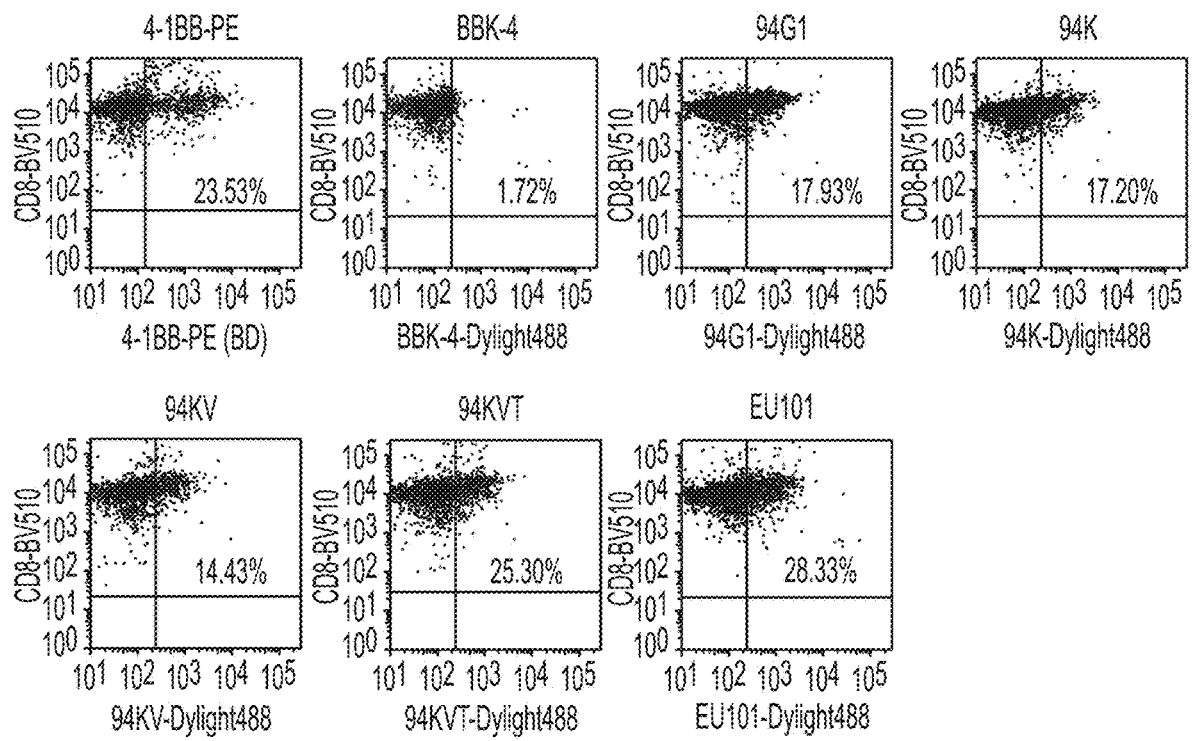
FIG. 6 depicts binding of anti-4-1BB monoclonal antibodies to 4-1BB expressing CD8+ T cells. CD8+ T cells were isolated from human PBMCs and activated by anti-CD3 antibody for 2 days. 4-1BB-PE is an exemplary commercially available anti-4-1BB antibody, BBK-4 is a murine anti-human 4-1BB antibody, 94G1, 94K, 94 KV, 94KVT and EU101 are exemplary humanized variant anti-4-1BB antibodies. The graph in the bottom panel reflects the values shown for each antibody in the FACS data in the top panels.
Figure 6:
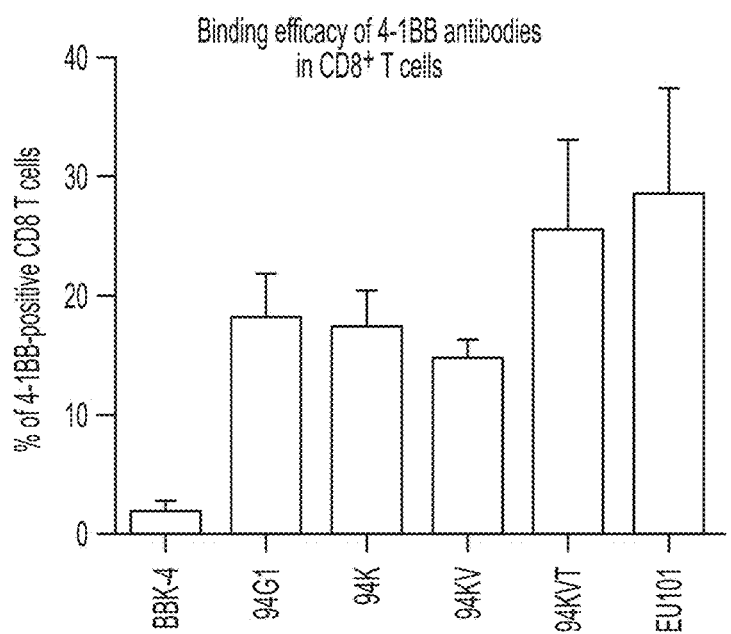

Exemplary antibodies were detected with an anti-mIgG-Dylight488 or anti-hIgG-Dylight488 as appropriate, and analyzed by FACS. Results are shown in FIG. 6. While a reference 94G1 antibody detected 4-1BB on 17.93% of CD8+ T cells, each of a 94KVT and EU101 antibody showed robust detect of 25.3% and 28.33%, respectively. Demonstrating that exemplary antibodies 94KVT and EU101 both had improved binding properties over BBK-4 and 94G1. Thus, humanized variant antibodies of the present disclosure have superior binding to activated T cells in vitro.

Example 3—Analysis of In Vitro Efficacy of Humanized Anti-Human 4-1BB Antibodies Anti-4-1BB antibodies have previously been demonstrated to provide signal stimulation to a co-stimulation molecule expressed in activated CD8+ T cells, 4-1BB, to activate the CD8+ T cells, induce proliferation and increase $T_H1$-type cytokine expression. In this example, activity of exemplary humanized anti-human 4-1BB antibodies described in Example 1 to induce proliferation of CD8+ T cells and $T_H1$-type cytokine expression was examined.

Figure 7:
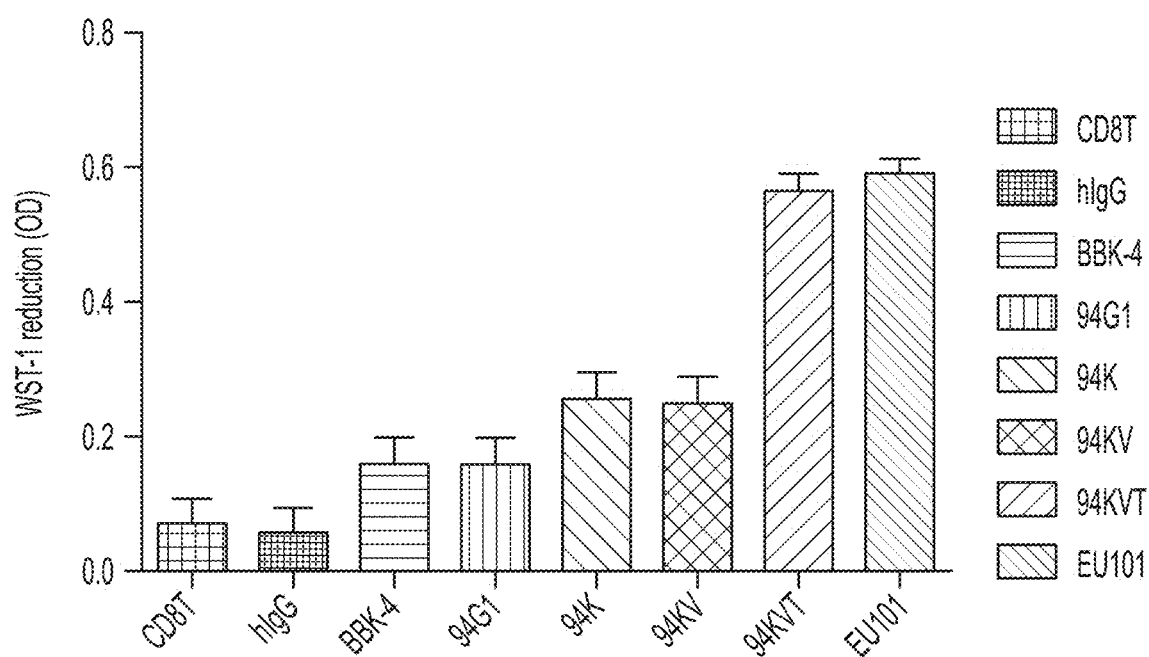
FIG. 7 depicts a graph quantifying in vitro proliferation of CD8+ T cells treated with anti-4-1BB antibodies. Proliferating CD8+ T cells were treated with no antibody, human IgG alone, BBK-4, or an exemplary humanized variant anti-4-1BB antibody: 94G1, 94K, 94 KV, 94KVT and EU101 and treated with WST-1 (water-soluble tetrazolium salt) to stain proliferating (i.e., metabolically active) cells.

3.1 Exemplary Anti-Human 4-1BB Antibodies Induce Cell Proliferation of CD8+ T Cells To assess proliferation of CD8+ T cells, cells were stained with WST-1 (water-soluble tetrazolium salt) is a cell proliferation reagent. WST-1-labeled CD8+ T cells were prepared and activated with 0.5 μg/ml of anti-CD3 antibody. The activated CD8+ T cells were treated with 1.0 μg/ml of iso-type control antibody, murine BBK-4 antibody, reference 94G1 antibody, and exemplary humanized anti-human 4-1BB antibodies (94K, 94 KV, 94KVT and EU101) described in Example 1. Cells were analyzed using a MACS system and results are shown in FIG. 7. Referring to FIG. 7, it was confirmed that exemplary humanized anti-human 4-1BB antibodies of the present disclosure induce cell proliferation of CD8+ T cells. Moreover, a degree of CD8+ T cell activation increases in an order of 94G1<94K/94 KV<94KVT/EU101.

3.2 Exemplary Anti-Human 4-1BB Antibodies Stimulate Cytokine Secretion

IFN-γ is a representative cytokine primarily secreted from a T lymphocyte or a natural killer cell (NK cell) and exhibiting proliferation and anti-viral activities. In addition, IFN-γ is a major activator for a macrophage, and particularly, a major cytokine distinguishing $T_H1$ cells from other types of cells. IFN-γ secretion plays a major role in the activation of cytotoxic T cells, phagocytes and B cells. Consequently, efficiency of an anticancer agent can be evaluated with an increased amount of $T_H1$ inducing IFN-γ. For this reason, measurement of secretion of IFN-γ by specific stimulation may be an optimal standard which can be used as a quantitative criterion for a functional change of T cells.

Figure 8:
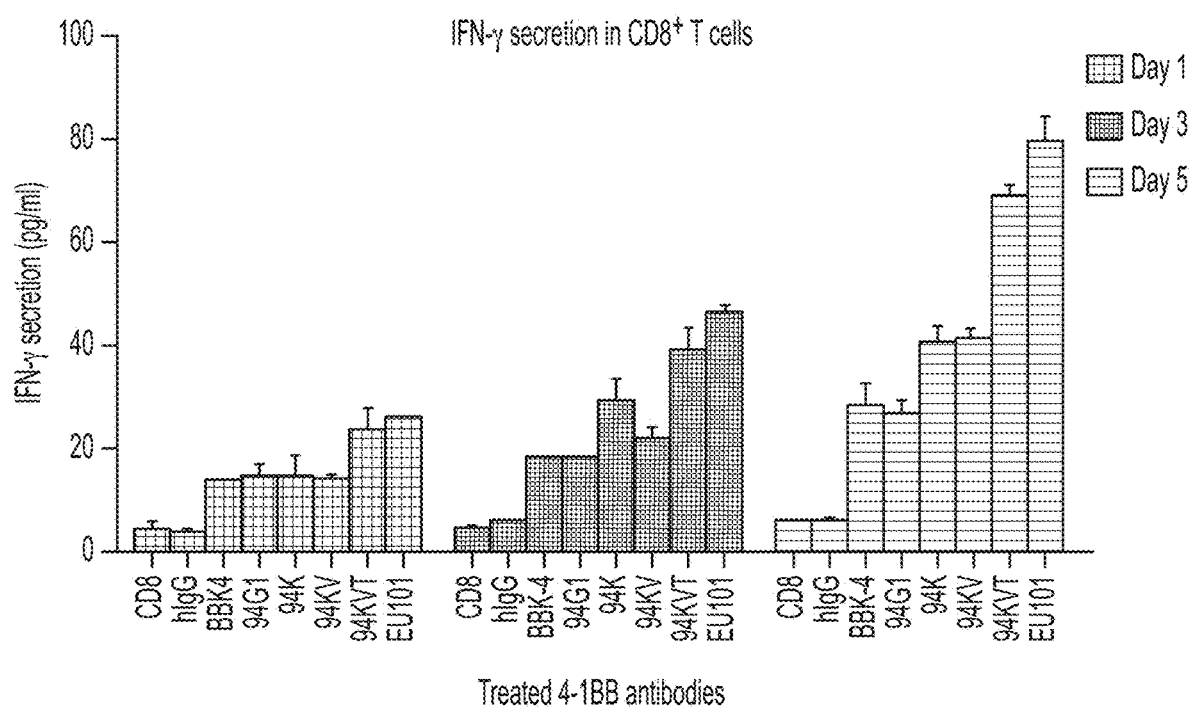
FIG. 8 depicts a graph quantifying in vitro IFNγ secretion by CD8+ T cells treated with anti-4-1BB antibodies. CD8+ T cells were isolated from human PBMCs and treated with no antibody, human IgG alone, or 1 µg/ml of an anti-4-1BB antibody: BBK-4, 94G1, 94K, 94 KV, 94KVT and EU101. IFNγ secretion was evaluated on days 1, 3, and 5.

CD8+ T cells were isolated from human PBMCs and treated with 0.5 μg/ml of an anti-CD3 mAb antibody and then treated with either no antibody, or with 1.0 μg/ml of an anti-4-1BB antibody: BBK-4, 94G1, 94K, 94 KV, 94KVT and EU101. IFNγ secretion was evaluated on days 1, 3, and 5. Results are shown in FIG. 8. As can be seen in FIG. 8, IFNγ secretion increased in all anti-4-1BB antibody treated samples, and this increase correlated with duration of antibody treatment. Treatment with 94KVT and EU101 antibody reached a secretion level that was 13-fold higher than the control group as day 5. Accordingly, exemplary humanized antibodies 94KVT and EU101 can both induce IFNγ secretion more efficiently than 94G1 reference antibody.

3.3 Increase in IFN-γ Level According to Treatment of Activated CD4+ T Cells or CD8+ T Cells with an Exemplary Anti-Human 4-1BB Antibody Blood was collected from three healthy donors, PBMCs obtained there from were isolated by Ficoll-plaque gradient centrifugation, and active T cells present in the PBMCs were rested in a RPMI-1640+2% FBS medium for 24 hours. The rested PBMCs were treated with an iron beads-attached anti-CD4 antibody or anti-CD8 antibody, and CD4+ cells or CD8+ cells were isolated using an MACS magnetic separator. The isolated CD4+ T cells or CD8+ T cells were treated with a T cell activator, anti-CD3, to induce 4-1BB expression, and treated with EU101 at different concentrations (0.5, 1.0, 2.5, and 5.0 μg/ml) for 3 days. After 3 days, a culture medium excluding the cells was obtained, and fluorescence of human IFN-γ in the culture medium was assessed by ELISA (ebioscience), and the result was compared with the standard curve provided in an IFN-γ ELISA kit (FIG. 9).

Figure 9:
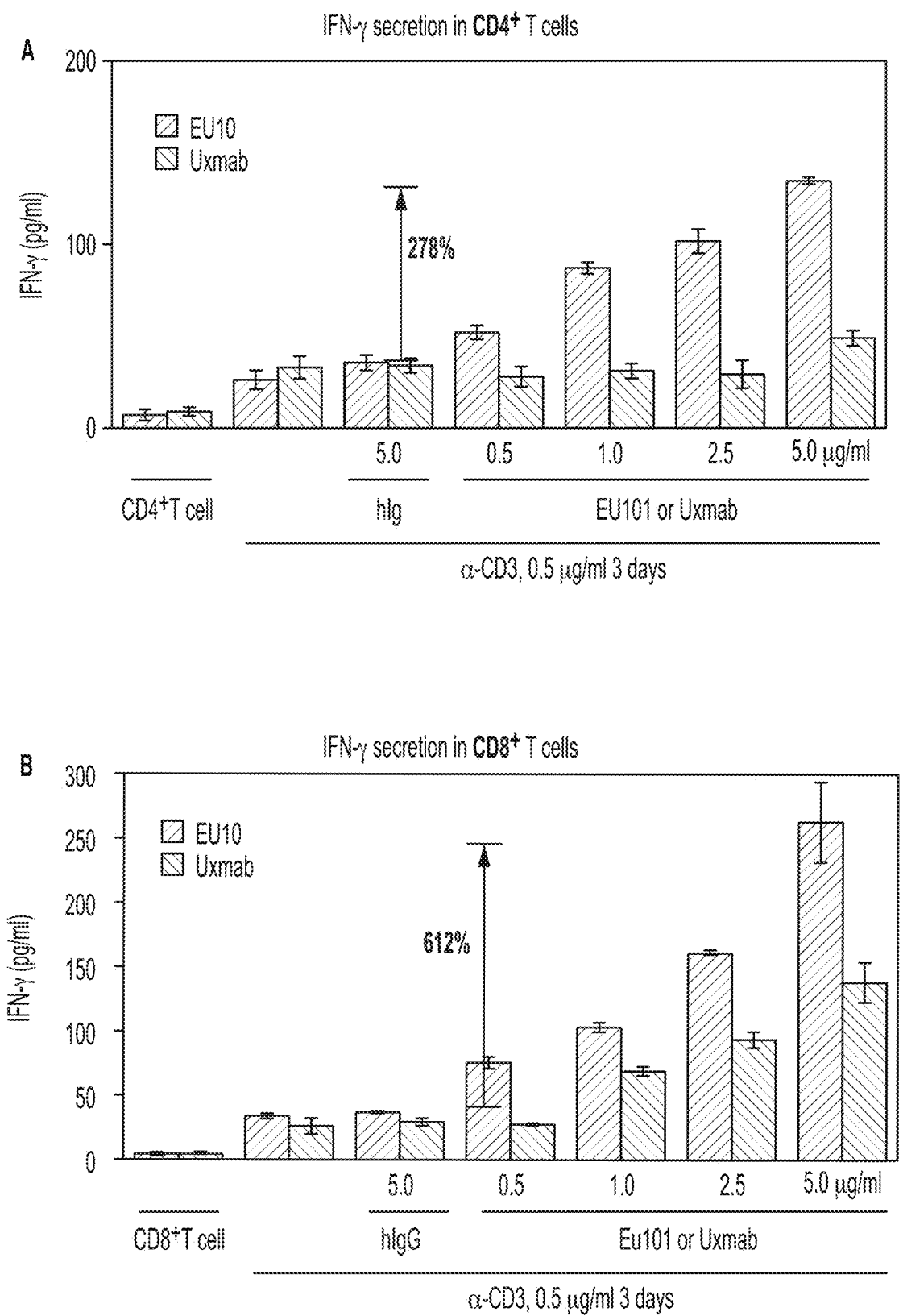
FIG. 9 shows graphs depicting IFN-γ secretion in (A) CD4+ and (B) CD8+. After being isolated from PBMCs of a healthy donor, activated T cells present in the PBMCs were rested in a RPMI-1640+2% FBS medium for 24 hours, and the rested PBMCs were treated with an iron beads-attached anti-CD4 antibody or anti-CD8 antibody, and CD4+ cells or CD8+ cells were isolated using an MACS magnetic separator. The isolated CD4+ T cells or CD8+ T cells were treated with a T cell activator, anti-CD3, to induce 4-1BB expression, and treated with EU101 at different concentrations (0.5, 1.0, 2.5, and 5.0 µg/ml) or a control human IgG (5.0 µg/ml) for 3 days. After 3 days, a culture medium excluding the cells was obtained, and fluorescence of human IFN-γ in the culture medium was assessed by ELISA (ebioscience). Results were compared with a standard curve as provided in an IFN-γ ELISA kit.

As shown in FIG. 9, expression levels of IFN-γ in the CD4+ T cells and CD8+ T cells dose-dependently increased. Particularly, when 5.0 μg/ml of EU101 was treated, compared with a 278% increase in the CD4+ T cells, the expression level of IFN-γ increased 612% in the CD8+ T cells. According to the T-cell specific expression pattern of IFN-γ involved in the conversion of the T cells into $T_H1$, an exemplary anti-human 4-1BB antibody of the present disclosure, EU101, has sufficient in vitro activity to suggest it may be effective for prevention and/or treatment of cancer.

3.4 Measurement of ADCC and CDC Activities of an Exemplary Anti-Human 4-1BB Antibody An immune system recognizes and attacks virus-infected cells or cancer cells, and antibodies may be used to induce cytotoxicity mediated apoptosis. For such an immune system, two types of mechanisms such as antibody-dependent cellular cytotoxicity (ADCC) and complement-dependent cytotoxicity (CDC) may be used. In both cases, apoptosis may be mediated by an antibody binding to a target on a cell surface. That is, when an antibody has an ADCC activity, a cell recognized by the antibody results in apoptosis mediated by a natural killer (NK) cell, and when an antibody has a CDC activity, killing is mediated by a complement protein. Therefore, in the case of the development of an antagonistic antibody therapeutic, a degree of killing cells recognized by an antibody can be identified through analyses of the ADCC and CDC activities. However, a target for the humanized 4-1BB antibody disclosed in the present disclosure is T cells, not cancer cells. That is, in consideration of a mechanism for inducing activation of T cells by binding a 4-1BB antibody as an agonistic antibody, an antibody that does not have the ADCC and CDC activities may be preferably for therapeutic uses.

Figure 10A:
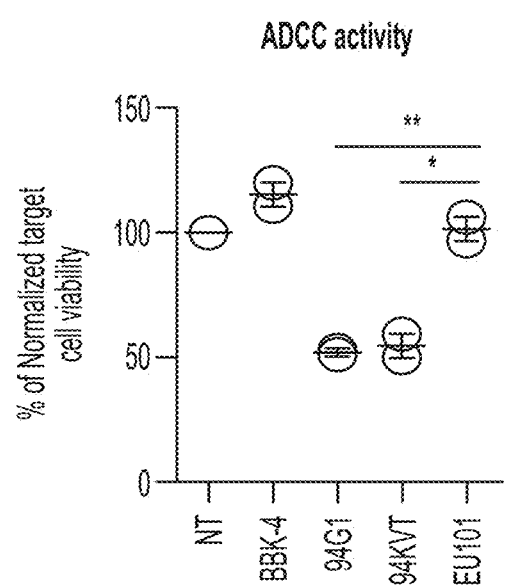
FIG. 10A shows a graph depicted antibody-dependent cytotoxicity (ADCC) of exemplary anti-human 4-1BB antibodies BBK4, 94G1, 94KVT and EU101.

In the present disclosure, for an ADCC assay, human PBMCs were isolated by Ficoll centrifugation using the same density difference. The PBMCs were incubated into RPMI (Thermo Fisher Scientific) and 10% FBS with IL-2 (100U/ml) for overnight cultured. Target cells (4-1BB expressing cell lines) were harvested, resuspended in a culture medium at 1 ml, and labeled with 5 uM CFSE at 37° C. for 5 min. Effector/Target cells of the present disclosure were washed in a ratio of 10:1, counted and then dispensed. For analysis, an antibody of the present disclosure was prepared for a final concentration of 10 nM (1.5 µg/ml), and cultured on a plate at 37° C. for 4 hours. 5 µl of 7-AAD was added to each well and transferred to a FACS tube, and then the sample was analyzed by FACS manufactured by BDFACScan. Frequencies of non-viable target cells (CFSE$^+$ 7-AAD$^+$) viable target cells (CFSE$^+$7-AAD$^-$) were measured. ADCC was assessed with a frequency of viable cells of the total cells (FIG. 10A).

Figure 10B:
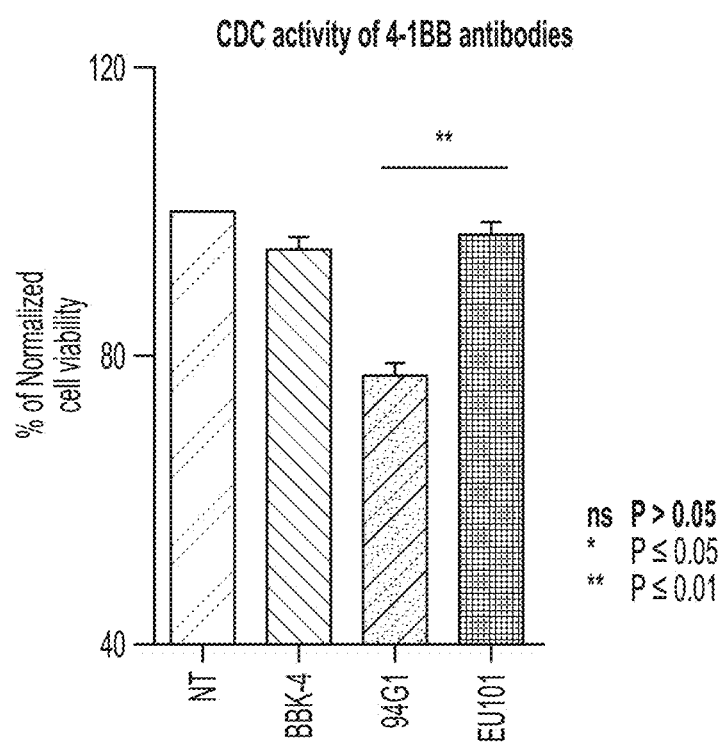
FIG. 10B shows a graph depicting complement-dependent cytotoxicity (CDC) of exemplary anti-human 4-1BB antibodies BBK4, 94G1, and EU101.

A complement-dependent cytotoxicity (CDC) assay was conducted similarly to the ADCC assay described above using FACS as a read-out value, with the above Target cells incubated with anti-4-1BB antibodies at ice for 30 min and then added the human supplemented serum at a final concentration of 20% at 37° C. for 30 minutes. Afterward, resulting samples were each transferred to a FACS tube, and assessed by FACS manufactured by BDFACScan (FIG. 10B). The results in FIG. 10A and FIG. 10B confirm that an exemplary humanized 4-1BB antibody, EU101, has almost no ADCC and CDC effects. Therefore, it can be said that an exemplary EU101 antibody of the present disclosure has beneficial ADCC and CDC properties for an agonist antibody, and is a good candidate for anti-cancer treatment in vivo.

Example 4—Confirmation of In Vivo Efficiency of an Exemplary Humanized Anti-Human 4-1BB Antibody The anti-human 4-1BB antibody, EU101, of the present disclosure showed a dose-dependent effect in an in vitro example, and showed a considerably superior effect to a conventional antibody. This example is to check if the anti-human 4-1BB antibody, EU101, is able to be used alone or in combination with a different composition to diagnose, prevent or treat cancer or tumor in vivo, and to effectively inhibit the growth of tumor.

4.1 NOD-Scid IL2Rgamma$^{null}$ Mouse Engraftment of Human Peripheral Blood Mononuclear Cells and Anti-Tumor Activity of Anti-Human 4-1BB Antibody Peripheral venous blood collected from a HLA-A24-type healthy donor was treated with heparin, and subjected to concentration-gradient centrifugation on Ficoll-paque (GE Healthcare, Piscataway, N.J.) to harvest PBMCs. The PBMCs were washed with an RPMI-1640 medium, and $3\times10^6$ of the cells were intraperitoneally injected into immnodeficient mice, that is, NSG mice (NOD.Cg-Prkdc$^{scid}$ Il2rg$^{tm1Wjl}$/SzJ; NOD-scid IL2rγ$^{null}$, Jackson Laboratory).

Analysis of humanized mice was performed by flow cytometry to check whether human T cells were present in the mouse blood collected by mouse orbital blood collection after 5 weeks of the engraftment of human PBMCs. 7-week-old NSG mice (Jackson Laboratory, Barharbor, Me.) were raised under a specific pathogen-free (SPF) environment.

Figure 11:
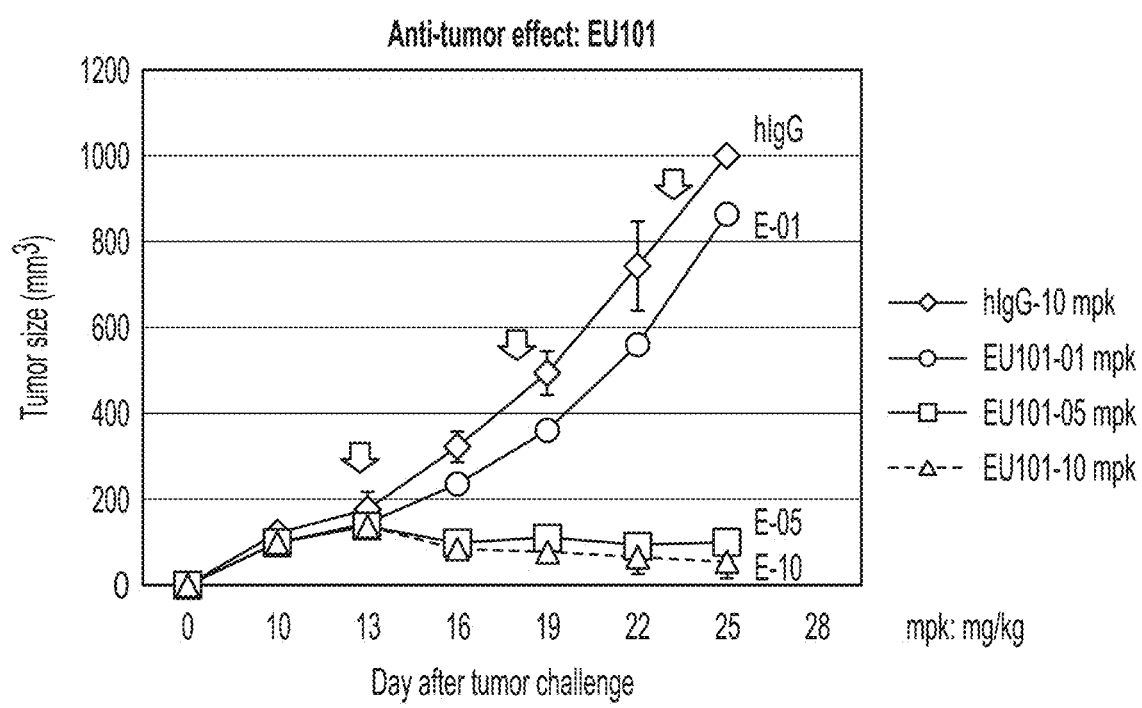
FIG. 11 shows in vivo anticancer effects of an exemplary anti-human 4-1BB antibody (EU101) by concentration, which are measured as tumor sizes after colon cancer tumor cells (HT29) were subcutaneously injected into humanized mice, and when tumor sizes reach 100 to 200 mm$^3$, an exemplary anti-human 4-1BB antibody (EU101) was intravenously administered to mice at doses of 1.0 mg, 5.0 mg and 10.0 mg per 1 kg of a body weight once every 5 days 3 times (representative data).

Flow cytometry was performed to check ratios of CD4 and CD8 after the cells were stained with human blood cell markers such as an APC-cy7 fluorescence-labeled CD45 antibody and a FITC fluorescence-labeled CD4 antibody, and a BV510 fluorescence-labeled CD8 antibody. After orbital blood collection from each mouse, human T cells from mouse blood samples were observed to check if a human immune system is engrafted into the mouse. Human tumor cells were prepared in an HLA type humanized mouse model and $1\times10^7$ cells were subcutaneously injected into the back of each mouse. When a tumor size reached 100 to 200 mm$^3$, a preparation of exemplary anti-human 4-1BB antibody (EU101) was intravenously administered at 1.0 mg, 5.0 mg or 10.0 mg per 1 kg of body weight once every 5 days total 3 times. As a control, human IgG was used. Tumor volume (mm$^3$) of each mouse was measured in every 3 days (FIG. 11). Results shown FIG. 11 confirm that tumor size in mice treated with an exemplary anti-human 4-1BB antibody (EU101) was reduced relative to mice treated with human IgG, and moreover that this reduction was proportional to antibody concentration. Particularly, tumor regression in a 5 mg/kg antibody-administered group occurred rapidly. Within a week after administration at a 5 mg/kg dose, tumor size settled in a humanized mouse and tumor growth was eradicated. Therefore, an exemplary antibody EU101 of the present disclosure shows an anticancer effect in vivo.

Consequently, the above results show that an exemplary anti-human 4-1BB antibody (EU101) that specifically recognizes an epitope (SEQ ID NO: 15) of H4-1BB, but due to improved characteristics of this exemplary antibody, such as, for example, improved affinity, this antibody shows superior effects in an in vivo mouse model. Thus, the example suggests that an antibody encompassed by the present disclosure can be used as an anticancer agent at a lower dosage than reference antibody.

Figure 12:
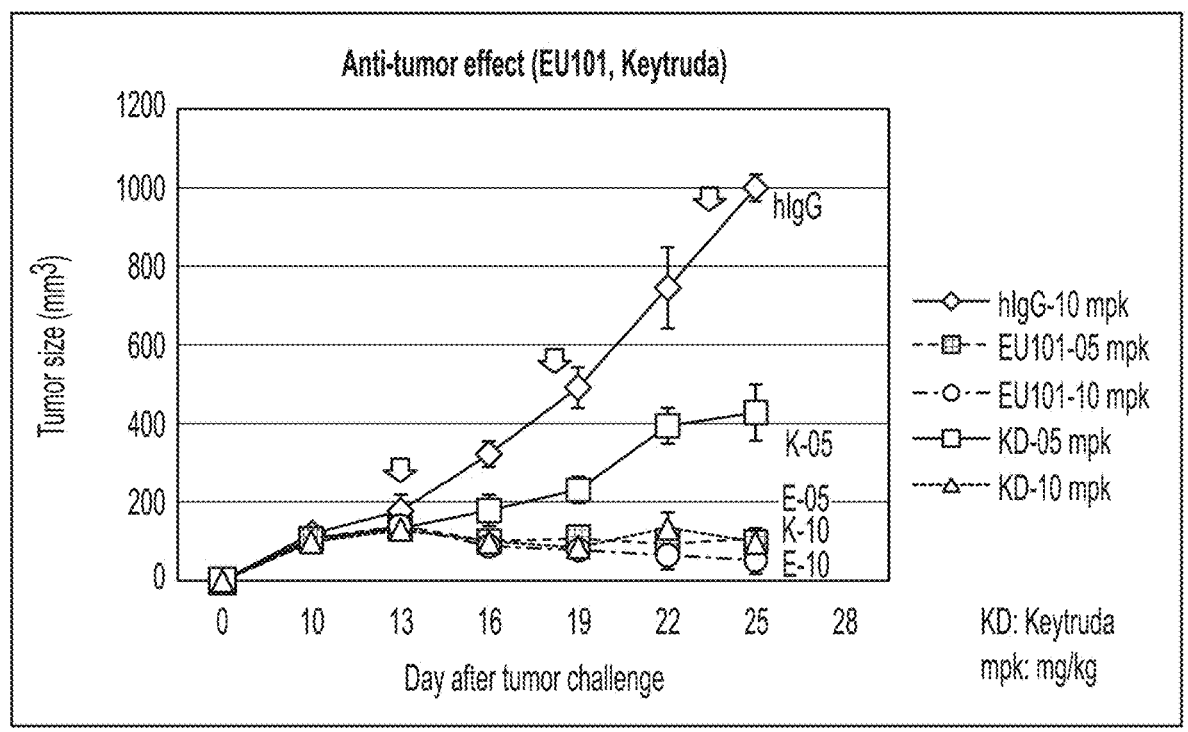
FIG. 12 shows anticancer effects of an exemplary anti-human 4-1BB antibody (EU101) and an exemplary anti-PD-1 antibody (Keytruda, "KD") antibodies by concentration. Anticancer effects were measured as tumor sizes after subcutaneous injection of colon cancer tumor cells (HT29) into humanized mice and antibody treatment. When tumor sizes reached 100 to 150 mm$^3$, mice were treated with an exemplary anti-human 4-1BB antibody (EU101) or an exemplary anti-PD-1 antibody (Keytruda) by intraperitoneal injection at a dose of 5.0 mg and 10.0 mg per 1 kg of body weight once every 5 days three times.

4.2 Effects of Inhibiting Tumor Growth with an Exemplary Anti-Human 4-1BB Antibody and an Anti-PD-1 Agent Comparison of Effects Caused by Individual Treatment of an Exemplary Anti-Human 4-1BB Antibody (EU101) and an Exemplary Anti-PD-1 Agent after Tumor Injection to Humanized Mice Humanized mice were prepared by the same method described in Example 4.1 above. To perform an experiment confirming an increase in anti-cancer effect according to doses of an exemplary anti-human 4-1BB antibody (EU101) and an exemplary anti-PD-1 agent (Keytruda)(purchased from MSD, GER), $1\times10^7$ cells of a HLA-A-type matched human colorectal adenocarcinoma cell line, HT29, were subcutaneously injected into the previously-prepared humanized mice. When the volume of the injected tumor reached 100 to 150 mm$^3$, the mice were divided into a total 5 groups of three mice, and to compare the effect of EU101 on tumor inhibition, each group of mice were treated with each of five three administration conditions (Control: IgG, Treated group 1: 5 mg/kg, and Treated group 2: 10 mg/kg) at 5 day intervals 3 times, and for anti-PD-1, the same procedures were carried out (FIG. 12). As a result of the experiment, in both cases of EU101 and keytruda (anti-PD1), tumor volumes were dose-dependently reduced. However, in FIG. 12, 5 mg/kg of EU101 did not have an influence on the tumor growth, but according to the treatment with 5 mg/kg and 10 mg/kg of EU101, an anti-tumor activity was dose-dependently exhibited. In addition, it was confirmed that EU101 exhibited higher efficiency at a lower dose than keytruda (anti-PD-1), and the tumor growth was completely blocked particularly by the treatment with 5 mg/kg of EU101. Treatment of humanized mice with combination of EU101 and an anti-PD-1 agent after tumor injection Since co-inhibitory receptors (PD-1 and CTLA-4) signals and a co-stimulation (CD137) T cell signal are differentiated for the same purpose of inhibiting tumor growth, stimulation of the two receptors can expect a synergyic effect (Chen et al., *Cancer Immunol. Res*. (2015) 3:149-160; Bartkowiak et al., *Front. Oncol*. (2015) 5: 117, both of which are incorporated by reference herein). In addition, PD1 immunotherapy showed a possibility of an anticancer treatment effect for some of cancer patient populations, but the administration of a low dose in combination therapy with a different anticancer agent may still be required in more extensive patient population. To investigate the anti-tumor effect caused by a combination therapy of an exemplary anti-human 4-1BB antibody (EU101) and an exemplary anti-PD-1 agent (Keytruda), tumor-bearing humanized mice were treated with the combination therapy of EU101 and Keytruda. Preparation of humanized mice was performed by the same method as described in Example 4.1

Eye bleeding was performed to identify humanized mice. Among the humanized mice, HT29, colon carcinoma were subcutaneously injected into HLA-A24 mice maintaining a normal condition at $1 \times 10^7$ cells/mice. When a tumor size was 300 to 450 mm$^3$, an experiment was performed as follows.

Figure 13:
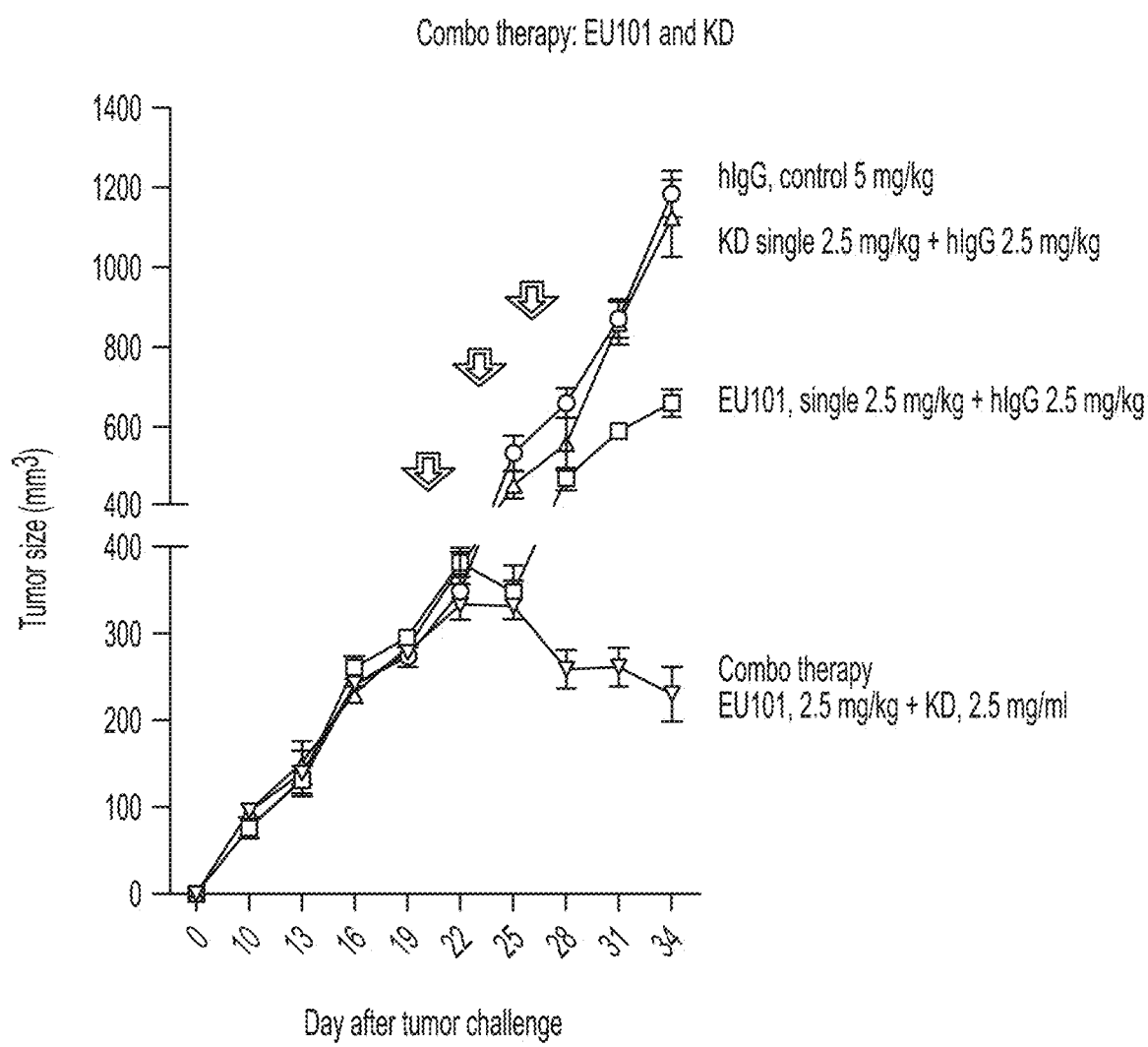
FIG. 13 shows comparative anticancer effects of individual treatment and combination therapy of an exemplary anti-human 4-1BB antibody (EU101) and an exemplary anti-PD-1 antibody (Keytruda). Anticancer effects were measured as tumor sizes after colon cancer tumor cells (HT29) were subcutaneously injected into humanized mice and antibody treatment. When tumor sizes reach 300 to 450 mm$^3$, an exemplary anti-human 4-1BB antibody (EU101) was administered at 2.5 mpk for individual treatment, an exemplary anti-PD-1 antibody (Keytruda) was administered at 2.5 mpk for individual treatment, and EU101, 2.5 mpk+ Keytruda, 2.5 mpk were administered for combination therapy. Administration was by intraperitoneal injection of mice, once every three days, for a total of three times.

As known from this example, although tumor growth was not delayed with individual injection at the minimum concentration or less (EU101: 2.5 mg/kg, Keytruda (manufactured from MSD, GER): 2.5 mg/kg), tumor was greatly regressed with combination therapy of EU101 and Keytruda. This is the result showing that exemplary anti-human 4-1BB antibodies provided herein (e.g., EU101) are good candidates for combination therapy with different anticancer agents, including in combination with one or more immune checkpoint inhibitors (FIG. 13).

Analyses of T Cell Infiltrating Lymphocytes (TILs) in Normal Tissue and Human Colorectal Adenocarcinoma Tissue after Individual and Combination Treatment of an Exemplary Anti-Human 4-1BB Antibody and an Exemplary Anti-PD-1 Agent After individual administration of an exemplary anti-human 4-1BB antibody (EU101) and an exemplary anti-PD-1 agent (Keytruda) (purchased from MSD, GER) and combination administration of EU101 and Keytruda to HT29-implanted humanized mice, on the day when the effect analysis is terminated, all groups were dissected to separate tumor and blood. After the separated tumor was treated with collagenase IV at 37° C. for 30 minutes, cells in the tumor tissue were dissociated by a mechanical method and then washed with 1×PBS. PBMCs were separated from the separated blood by Ficoll gradient centrifugation, and separated tumor cells and PBMCs were subjected to the following experiment. Red blood cells (RBCs) were removed from washed cells using RBC lysis buffer and then washed with 1×PBS. Tangled cell debris was removed from the washed cells using a 40-μm nylon cell strainer to create a single cell state, and the single cells were washed with 1×PBS, followed by counting T cells separated from each group using a cell counter.

Figure 14A:
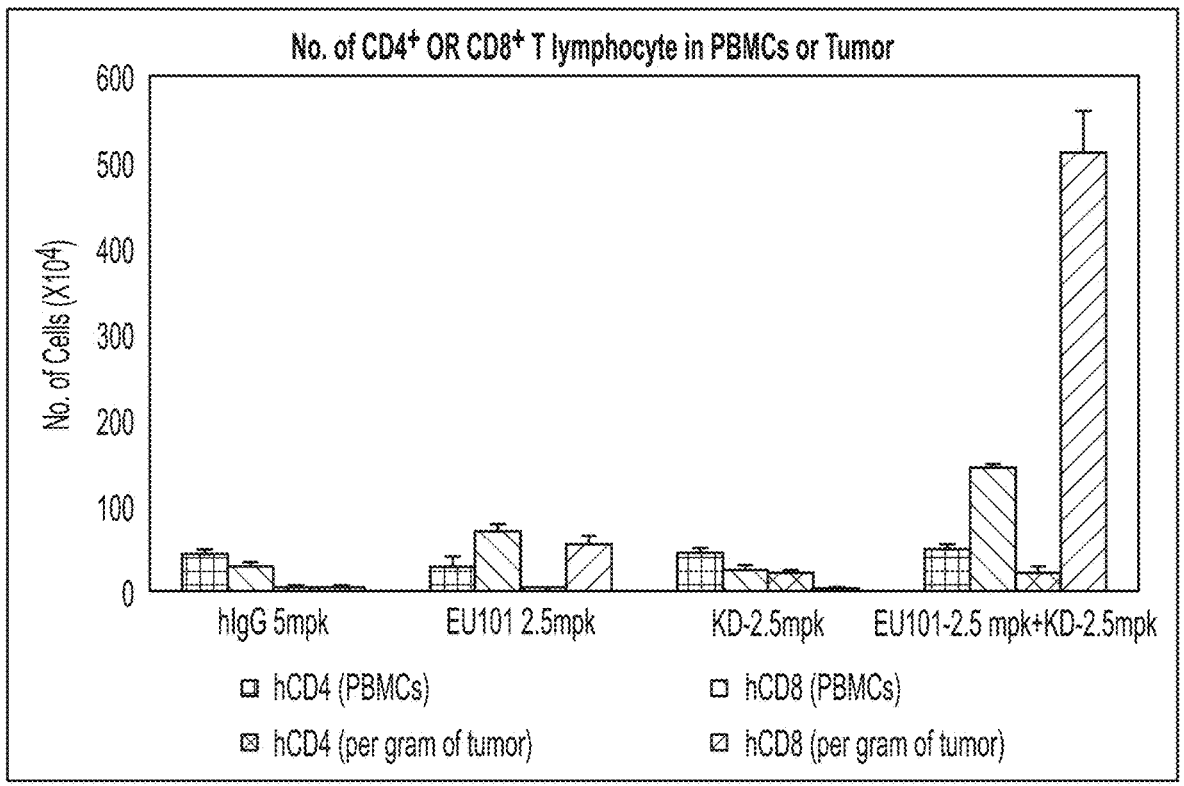
FIG. 14A shows the numbers of human CD4$^+$ T cells and CD8$^+$ T cells circulated in mouse blood or 1 gram of tumor tissue at 34 days after treatment with an exemplary anti-human 4-1BB antibody (EU101) and an exemplary anti-PD-1 antibody (Keytruda), individually and in combination, on tumor-implanted humanized mice, as described in FIG. 13. The number of T cell infiltrating lymphocytes (TILs) in tumor were measured by calculating proportional ratios of the total cell numbers by measuring ratios (%) of CD4$^+$ T cells and CD8$^+$ T cells using a flow cytometer. Flow cytometry was performed to measure the ratios (%) of the CD4$^+$ T cells and CD8$^+$ T cells after cells are stained with a FITC-labeled CD4 antibody, a fluorescent BV510-labeled CD8 antibody and a fluorescent APC-cy7-labeled CD45 antibody, and a human blood cell marker, CD45-positive cells were separated from a flow cytometry program (gating).

The separate T cells were stained with human blood cell markers such as a CD45 antibody (fluorescent APC-cy7 labeled), a fluorescent FITC-labeled human CD4 antibody and a fluorescent BV510-labeled human CD8 antibody, and then subjected to FACS assay. The FACS assay was carried out based on a ratio (%) of CD4 and CD8 cell groups, which were gated from the CD45 group (FIG. 14A).

Particularly, to identify a Treg group among the separated T cells, the surfaces of cells were stained with human blood cell markers such as a CD45 antibody (fluorescent APC-cy7 labeled), a human fluorescent FITC-labeled CD4 antibody and a human fluorescent PE-cy5-labeled CD25 antibody, and intracellular and intranuclear staining with a cell transcription factor Foxp3 (human fluorescent APC-labeled Foxp3 antibody) were performed using a Foxp3/Transcription Factor Staining Buffer Set kit (ebioscience). In the FACS assay, a CD45 group was separated to gating R1, a CD4$^+$CD25$^{high}$ group was separated to gating R2, and a ratio (%) of a Foxp3$^{high}$ group was measured in the R1 and R2 groups. To identify IFN-γ$^+$CD8$^+$ T cells in the separated cells, the cell surfaces were stained with the blood cell markers such as the fluorescent APC-cy7-labeled human CD45 antibody and the fluorescent BV510-labeled human CD8 antibody, fixed with 2% PFA, and reacted with a 0.5% saponin solution and a fluorescent PE-cy7-labeled human IFN-γ antibody. Afterward, cytokine IFN-γ$^+$ cells in the CD8 T cell group were measured by FACS assay. The cells were identified in a ratio by the same method as described above and a proportional ratio of the CD8$^+$IFN-γ$^+$ ratio and the Treg ratio was calculated, shown in FIG. 14B.

Figure 14B:
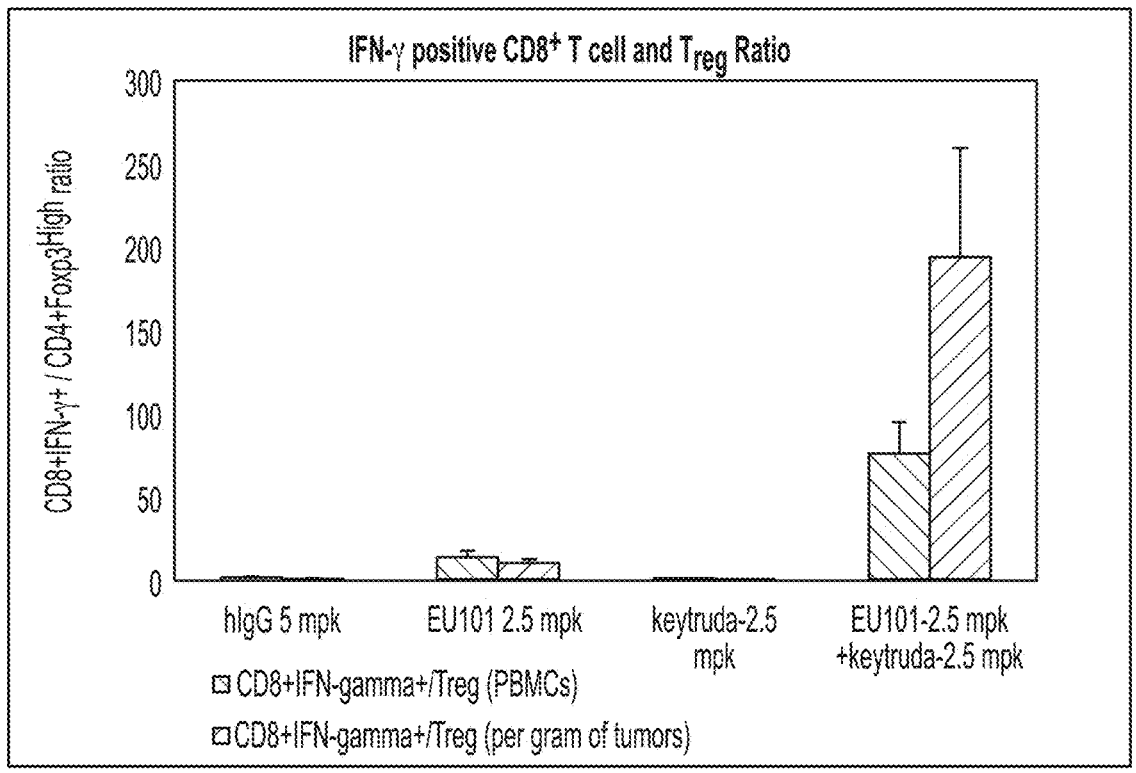
FIG. 14B shows a ratio of Treg (CD4$^+$Foxp3high T cells) per ratio of CD8$^+$IFN-γ$^+$ T cells measured by calculating a proportional ratio between the ratio of the CD8$^+$IFN-γ$^+$ T cells and the ratio of Treg (CD4$^+$Foxp3high T cells) using a flow cytometer after the cells were stained with fluorescent APC-cy7-labeled CD45, a fluorescent BV510-labeled CD8 antibody, a fluorescent FITC-labeled CD4 antibody, fluorescent PE-labeled INFγ, and fluorescent APC-labeled Foxp3 antibody.

According to the result of this embodiment, other than the individual administration, the combination administration of EU101 and Keytruda greatly increased infiltration of the combination of tumor tissue and a T lymphocyte. Further more specific results of the combination treatment are as follows. When the combination treatment was performed on PBMCs in the healthy humanized mouse as a control, the number of lymphocytes increased approximately 3 times, and the infiltrated lymphocytes per 1 g of tumor increased 76 times in tumor tissue. This means that most of tumor-specific lymphocytes were activated and recruited to tumor tissue to kill target cells. Particularly, when PBMCs in the combination therapy group were measured, as shown in FIG. 14A, the CD4$^+$ T cells do not highly increased, but cytotoxic CD8$^+$ T cells were increased approximately 5 times. Moreover, the combination therapy group showed a 100-fold increase in CD8$^+$ Tcell count per 1 g of tumor tissue. In addition, as a result, a ratio of CD8$^+$ T cells secreting IFN-γ and regulatory T cells was also greatly increased (FIG. 14B). That is, it can be said that the combination treatment of EU101 and anti-PD-1 agent gives a sharp increase of effector T cells and thus tumor inhibition is effectively performed.

Analyses of IFN-γ in Serum or Tumor Fluid Obtained from Human Colorectal Adenocarcinoma Tissue after Individual and Combination Treatment with an Exemplary Anti-Human 4-1BB Antibody (EU101) and an Exemplary Anti-PD-1 Agent (Keytruda)

After individual administration and combination administration of an exemplary anti-human 4-1BB antibody (EU101) and an exemplary anti-PD-1 agent (Keytruda) to HT29-implanted humanized mice. On the day when effect analyses were terminated, all groups were dissected to separate tumor and blood. In tumor dissection to separate a tumor fluid present in the separated tumor, 300 μl of 1×PBS was injected into the upper portion of a tumor membrane using a 1 cc-syringe, and a flowing solution is taken from the lower portion of the tumor membrane using an insulin syringe. In addition, in dissociation of the tumor tissue, the taken solution was added to dissociate the tumor tissue, and then stored. In addition, as a serum, the serum stored when PBMCs were separated from blood by Ficoll gradient centrifugation. The stored serum and a tumor fluid were dissolved and filtered using a 0.22 m filter unit (manufacturer: coming). 10 μl of serum was used for each group, and 100 μl of the tumor fluid was used to measure human IFN-γ and human TGF-ß using a human IFN-γ ELISA Ready-SET-Go kit (eBioscience) and a Human TGF beta 1 ELISA Ready-SET-Go kit (eBioscience). Results were analyzed by comparing the standard curve provided in each ELISA kit.

Figure 15A:
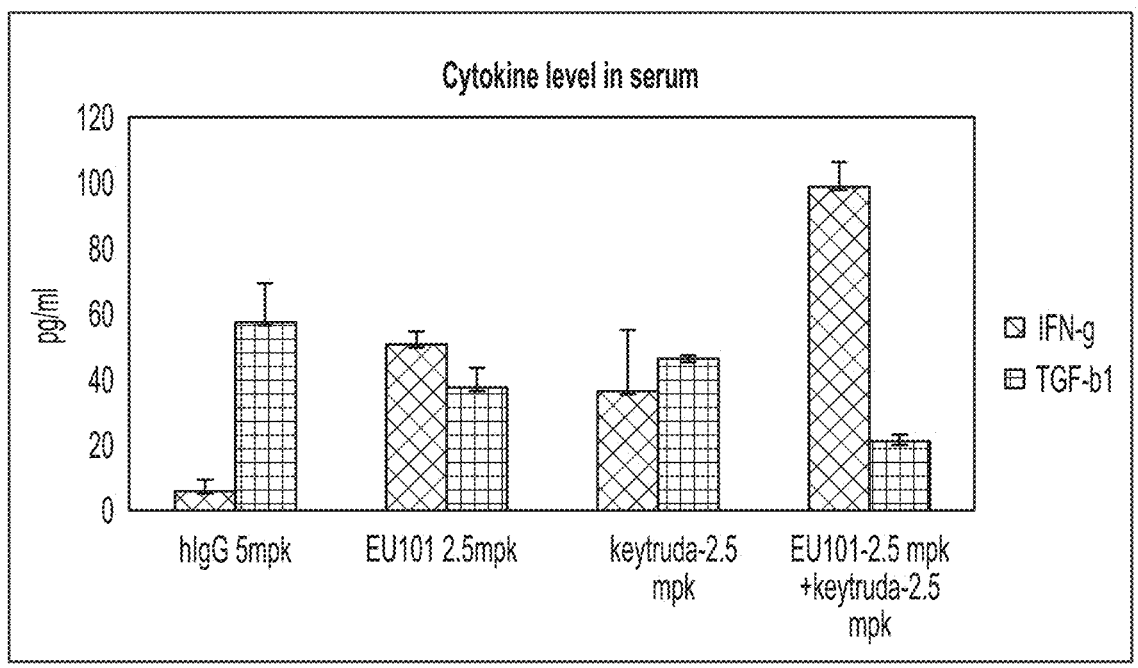
FIG. 15A and FIG. 15B show IFN-γ analysis results through serum and tumor fluid after individual and combination treatment of an exemplary anti-human 4-1BB antibody (EU101) and an exemplary anti-PD-1 antibody (Keytruda). After dissection performed on all of the treated groups shown in FIGS. 15A and 15B, 10 µl of serum and 100 µl of tumor fluid were analyzed with human IFN-γ and human TGF-ß ELISA kits.
Figure 15B:
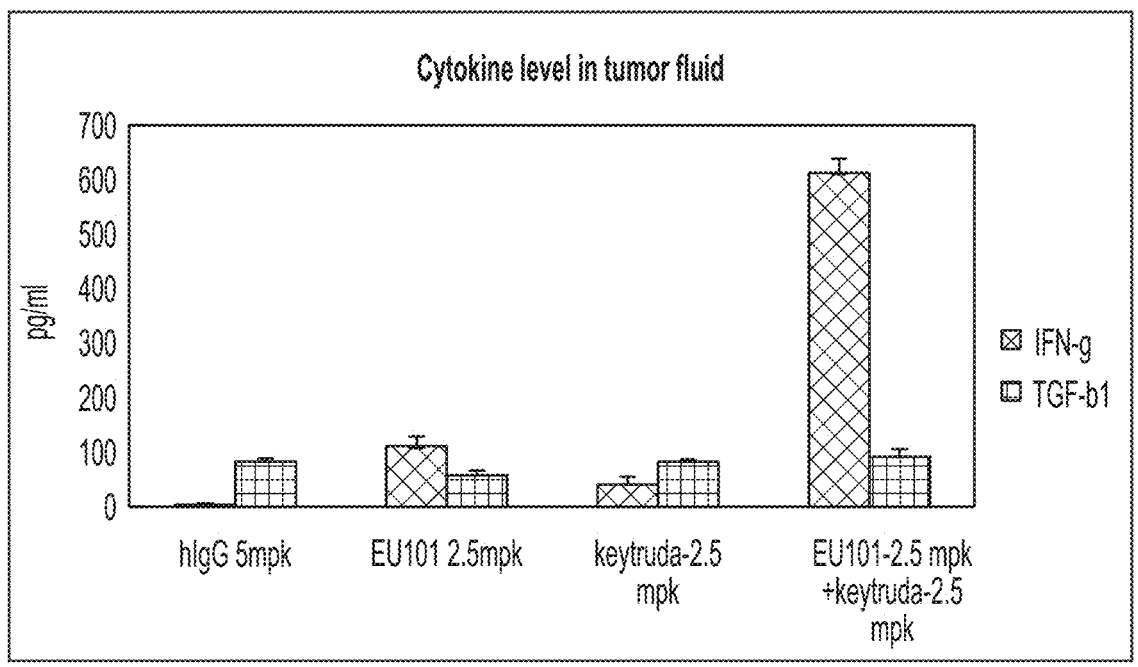

As a result, compared to the individual administration of EU101 and Keytruda, in the combination administration, the concentration of interferon in serum of the tumor group was the highest. Since a EU101 mechanism can be explained with a correlation between IFN-γ and an anti-tumor effect, expression levels of IFN-γ and TGF-β in serum of a healthy donor and serum of a tumor group, to which the combination therapy had been applied, were evaluated. According to the material of the example on the serum of the healthy donor, in the combination therapy group shown in FIG. 15A, IFN-γ was increased approximately 16 times, but a cytokine secreted from Treg cells, TGF-β, was decreased approximately 65%. In addition, in FIG. 15B, the IFN-γ concentration caused by the combination administration in the tumor fluid was considerably higher (approximately 213-fold) than that in the control. As a result of the examples, due to EU101, particularly, compared to the control group, the combination group showed sharp increases in IFN-γ secretion. Therefore, it can be confirmed that the anti-cancer effect caused by an improved anti-humanized 4-1BB antibody of the present disclosure gives effective tumor-infiltration of effector T cells directly related to apoptosis of cancer cells, and a considerably specific effect in the tumor tissue, compared to the non-treated group. In other words, in the present disclosure, it was confirmed that EU101, as an anti-cancer agent, has the optimal conditions for apoptosis of cancer cells. Conventionally, in cancer patients, anti-cancer cytokine and anti-cancer cellular immunity were considerably reduced, but it can be expected in the present disclosure that EU101 induces the increases in anti-cancer cytokine and anti-cancer cellular immunity, resulting in a considerable therapeutic effect.

Thus, an exemplary anti-human 4-1BB antibody EU101 exhibits an anti-tumor effect mediated by the high expression of IFN-γ, and such an effect is dose-dependently exhibited, as such, an IFN-γ concentration in a serum of a cancer patient can be used as a biomarker to diagnose and estimate tumor. Therefore, according to effective treatment of cancer or tumor through the combination treatment of EU101 and anti-PD-1 and prognosis through the measurement of an IFN-γ concentration, it is expected to perform more effective treatment with respect to each patient.

Example 5—Separation and Massive Proliferation of 4-1BB+CD8+ T Cells Ex Vivo Using an Exemplary Humanized Anti-Human 4-1BB Antibody The inventors used 4-1BB expression in antigen-specifically activated CD8+ T cells in isolation and purification of 4-1BB+CD8+ T cells specific to various antigens using an anti-4-1BB antibody (Korean Patent No. 10-1503341). A subsequent experiment was performed to examine if the EU101 antibody developed herein is also used for isolation and mass-proliferation of antigen-specific CD8+ T cells.

Figure 16A:
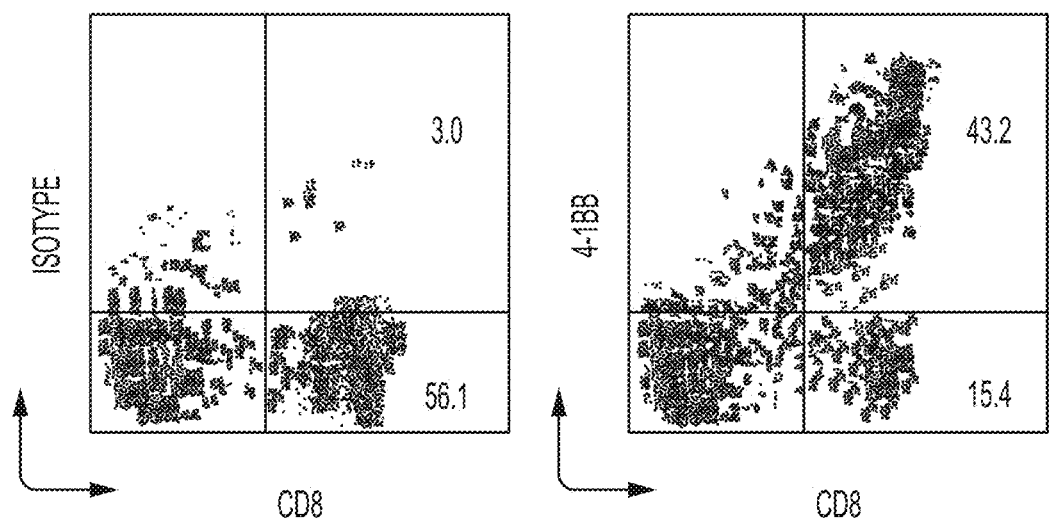
FIG. 16A shows antigen-specific CD8$^+$ T cell ratios (ratio of 4-1BB$^+$CD8$^+$ T cells: 43.2%, ratio of CD8$^+$ T cells: 58.6%) measured before panning with an exemplary anti-human 4-1BB antibody (EU101).
Figure 16B:
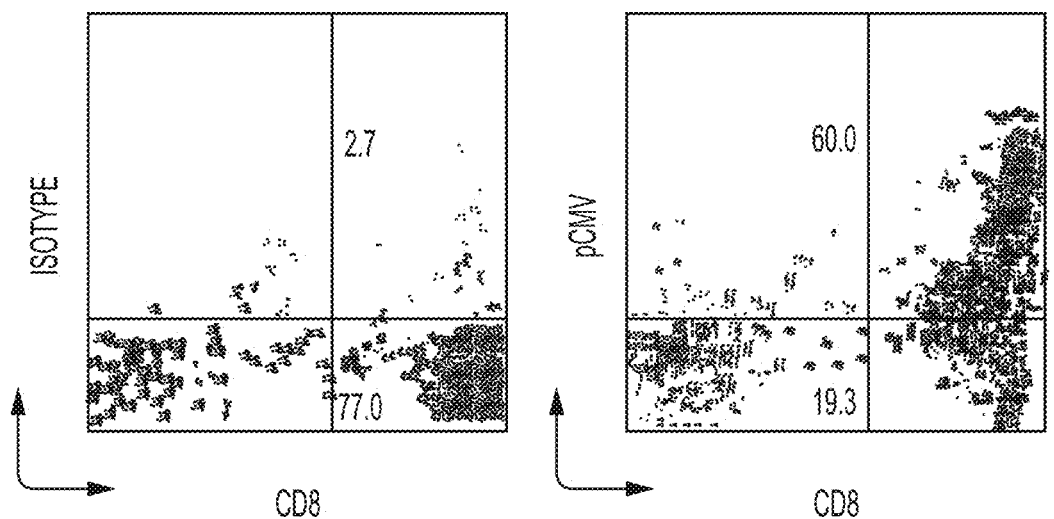
FIG. 16B shows antigen-specific CD8$^+$ T cell ratios (ratio of pCMV+CD8$^+$ T cells: 60.0%, ratio of CD8$^+$ T cells: 79.3%) measured after panning with an exemplary anti-human 4-1BB antibody (EU101).

Construction of PBMCs from peripheral blood of a cancer patient was performed as described in Example 4.1. However, in this example, cancer antigen-specific undifferentiated T cells may be obtained by the method described in Korean Patent Application No. 10-2016-0165224, filed by the inventors. In this example, for effective separation of 4-1BB+CD8+ T cells and mass-production of the 4-1BB+CD8+ T cells with high purity, a panning method using an anti-human 4-1BB antibody (EU101) was used. 10 μg/ml of the anti-human 4-1BB antibody (EU101) antibody diluted in PBS was added to a 10 ml flask, and then stored at 4° C. for 20 to 24 hours. After storage, a supernatant containing the antibody was removed, and without washing, a solution of BSA dissolved at 2.5% in PBS was added to cell pellets in the 10 ml flask and then stored at 4° C. for 20 to 24 hours. Afterward, the BSA solution was removed, and each flask was washed twice with 15 ml of PBS. The previously-prepared cells were suspended in an X-VIVO 10 medium, added to a EU101 antibody-coated flask, and then incubated at 37° C. in a $CO_2$ incubator for 1 hour. After incubation, a supernatant was removed, and cell pellets were washed twice with 10 ml of RPMI1640 medium to remove non-specifically binding cells. 1% of self serum and a 1000 IU/ml IL-2-containing X-VIVO 10 medium were added to the flask, followed by culturing for 14 days. In the example, some cells were harvested and then stained to measure the purity and phenotypes of the isolated cells. As shown in FIGS. 16A and 16B, it was confirmed that, before panning with the 94 kvt antibody, a ratio of antigen-specific 4-1BB+CD8+ T cells increased 43.2% (CD8+ T cell ratio: 58.6%), and after panning with the EU101 antibody, a ratio of antigen-specific pCMV+CD8+ T cells increased 60.0% (CD8+ T cell ratio: 79.3%). This means that the antigen-specific 4-1BB+CD8+ T cells can be isolated with high purity using a EU101. Antigen-specific 4-1BB+CD8+ T cells isolated as described above may be easily mass-produced by the method described in Korean Patent Application No. 10-2016-0165224 filed by the inventors.

From the above description, it will be understood by those of ordinary skill in the art that the present invention can be realized in different specific forms without changing the technical idea or essential characteristics of the present invention. However, there is no intention to limit the present invention to the specific exemplary embodiments, and it should be understood that all modifications or modified forms deduced from the meaning and range of the following claims and equivalents thereof are included in the scope of the present disclosure, rather than the detailed description.

Anti-human 4-1BB antibodies encompassed by the present disclosure demonstrated a number of beneficial properties, such as, for example, superior affinity to a reference antibody, and/or can be used alone or in combination with another anticancer agent to diagnose, prevent or treat cancer or tumor, or used to inhibit the growth of cancer.

Above, the present invention has been described with reference to examples, but it can be understood by those of ordinary skill in the art that the present invention may be changed and modified in various forms without departing from the spirit and scope of the present invention, which is described in the accompanying claims.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the claims.

What is claimed is:

1. A method for treating cancer in a subject in need thereof, comprising:
   administering to the subject a therapeutically effective amount of activated T cells produced by contacting a population of T cells with an anti-4-1BB antibody or antigen-binding fragment comprising:
   (i) a heavy chain CDR1 comprising a sequence of SEQ ID NO: 5, a heavy chain CDR2 comprising a sequence of SEQ ID NO: 6 and a heavy chain CDR3 comprising a sequence of SEQ ID NO: 7 or 8; and
   (ii) a light chain CDR1 comprising a sequence of SEQ ID NO: 1, a light chain CDR2 comprising a sequence of SEQ ID NO: 2 and a light chain CDR3 comprising a sequence of SEQ ID NO: 4.

2. A method for treating cancer in a subject in need thereof, comprising:
   administering to the subject a therapeutically effective amount of CD8+ T cells produced by contacting a population of CD8+ T cells with an anti-4-1BB antibody or antigen-binding fragment comprising:
   (i) a heavy chain CDR1 comprising a sequence of SEQ ID NO: 5, a heavy chain CDR2 comprising a sequence of SEQ ID NO: 6 and a heavy chain CDR3 comprising a sequence of SEQ ID NO: 7 or 8; and
   (ii) a light chain CDR1 comprising a sequence of SEQ ID NO: 1, a light chain CDR2 comprising a sequence of SEQ ID NO: 2 and a light chain CDR3 comprising a sequence of SEQ ID NO: 4.

* * * * *